(12) United States Patent
    Shaughnessy

(10) Patent No.: US 7,459,437 B2
(45) Date of Patent: *Dec. 2, 2008

(54) MOLECULAR DETERMINANTS OF MYELOMA BONE DISEASE AND USES THEREOF

(75) Inventor: John D. Shaughnessy, Little Rock, AR (US)

(73) Assignee: University of Arkansas for Medical Sciences, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/727,461

(22) Filed: Dec. 4, 2003

(65) Prior Publication Data

US 2004/0137489 A1    Jul. 15, 2004

Related U.S. Application Data

(60) Provisional application No. 60/431,040, filed on Dec. 5, 2002.

(51) Int. Cl.
    *G01N 33/574*    (2006.01)
(52) U.S. Cl. .................. 514/12; 435/7.1; 435/7.23
(58) Field of Classification Search .................. 435/7.1, 435/7.23
    See application file for complete search history.

(56) References Cited

FOREIGN PATENT DOCUMENTS

| GB | 20040038860 | | 2/2004 |
|---|---|---|---|
| WO | WO 0052047 A2 | * | 9/2000 |
| WO | WO 0052047 A3 | * | 9/2000 |

OTHER PUBLICATIONS

Chappuis et al. (Cancer Treat Res. 2002; 107: 29-59).*
McLaughlin et al. (Tannock, I.F. and Hill, R.P., The Basic Science of Oncology, Chapter 2, (3rd Ed., 1998)).*
Stevenson et al. (BMJ 1989; 298: 924-928).*
Soroko et al. (J. Bone Miner. Res. 1994; 9: 761-769).*
Tockman et al (Cancer Res., 1992, 52:2711s-2718s).*
Slamon et al. (Science vol. 235, Jan. 1987, pp. 177-182).*
Verma et al. (1997) Nature vol. 389, pp. 239-242.*
Marshall (1995) Science, vol. 269, Issue 5227, pp. 1050-1055.*
Eck et al. (Goodman & Gilman's The Pharmacological Basis of Therapeutics (1996), 9th Edition, Chapter 5, McGraw-Hill, NY).*
Juengst (British Medical Journal (2003) vol. 326, pp. 1410-1411).*
Rubanyi (Mol. Aspects Med. (2001) 22:113-142).*
Zhang, Y. et al. The LRP5 High-Bone-Mass G171 Mutation Disrupts LRP5 Interaction with Mesd: *Molecular and Cellular Biology*, Jun. 2004, vol. 24, No. 11, pp. 4677-4684.
Boyden, L. M. et al. High Bone Density Due to a Mutation in LDL-Receptor-Related Protein 5: *N Engl J Med*, May 16, 2002, vol. 346, No. 20, pp. 1513-1521.
Little, R.D. et al.; A Mutation in the LDL Receptor-Related Protein 5 Gene Results in the Autosomal Dominant High-Bone-Mass Trait: *Am. J. Hum. Genet.*, 2002 vol. 70, pp. 11-19.

* cited by examiner

*Primary Examiner*—Brandon J Fetterolf
(74) *Attorney, Agent, or Firm*—Benjamin Aaron Adler

(57) ABSTRACT

To identify molecular determinants of lytic bone disease in multiple myeloma, the expression profiles of ~12,000 genes in CD138-enriched plasma cells from newly diagnosed multiple myeloma patients exhibiting no radiological evidence of lytic lesions (n=28) were compared to those with ≧3 lytic lesions (n=47). Two secreted WNT signaling antagonists, soluble frizzled related protein 3 (SFRP-3/FRZB) and the human homologue of Dickkopf-1 (DKK1), were expressed in 40 of 47 with lytic bone lesions, but only 16 of 28 lacking bone lesions (P<0.05). DKK1 and FRZB were not expressed in plasma cells from 45 normal bone marrow donors or 10 Waldenstrom's macroglobulinemia, a related plasma cells malignancy that lacks bone disease. These data indicate that these factors are important mediators of multiple myeloma bone disease, and inhibitors of these proteins may be used to block bone disease.

4 Claims, 43 Drawing Sheets

Goat polyclonal anti-human DKK1 + Rhodamine-Donkey anti-goat IgG1

Goat IgG1 + Rhodamine-Donkey anti-goat IgG1

α-DKK1

α- Ig kappa

MOLECULAR DETERMINANTS OF MYELOMA BONE DISEASE AND USES THEREOF

CROSS-REFERENCE TO RELATED APPLICATION

This application claims benefit of provisional patent application U.S. Ser. No. 60/431,040, filed Dec. 5, 2002, now abandoned.

FEDERAL FUNDING LEGEND

This invention was created, in part, using funds from the federal government under National Cancer Institute grants CA55819 and CA97513. Consequently, the U.S. government has certain rights in this invention.

BACKGROUND OF THE INVENTION

1. Field of the Invention

The present invention relates generally to the study of multiple myeloma. More specifically, the present invention relates to the identification of molecular determinants of myeloma bone disease through comparative global gene expression profiling.

2. Description of the Related Art

Multiple myeloma (MM) is a rare, yet incurable malignancy of terminally differentiated plasma cells (PC) that affects approximately 15,000 persons per year in the United States, and represents the second most common hematopoietic malignancy. Multiple myeloma represents 13% of all lymphoid malignancies in the white population and 31% of lymphoid malignancies in the black population. The malignant plasma cells home to and expand in the bone marrow causing anemia and immunosuppression due to loss of normal hematopoiesis.

Multiple myeloma is also associated with systemic oteoporosis and local bone destruction leading to debilitating bone pain and susceptibility to fractures, spinal cord compression and hypercalcemia. Myeloma is the only hematological malignancy consistently associated with lytic bone disease and local bone destruction is limited to areas adjacent to plasma cells, suggesting that the malignant plasma cells secrete factors that enhance osteoclast function and/or osteoblast anergy. The prevalence of bone disease varies with the presentation of myeloma, from smoldering myeloma, often without bone involvement, to solitary plasmacytoma, to diffused or focal multiple myeloma where systemic losses of bone mineral density or focal lytic bone lesions are seen in approximately 80% of patients.

In recent years, it has become evident that lytic bone disease is not only a consequence of myeloma, but that it is intricately involved in promoting disease progression. Change in bone turnover rates predicts clinical progression from monoclonal gammopathy of undetermined significance (MGUS) to overt myeloma by up to 3 years. While initially osteoclast and osteoblast activity are coupled, the coupling is lost with disease progression. Osteoclast activity remains increased and osteoblast activity is diminished, with lytic bone disease as the consequence. Studies in the 5T2 murine myeloma and the SCID-hu model for primary human myeloma demonstrated that inhibition of osteoclast activity is associated with inhibition of myeloma growth and reduction of myeloma tumor burden. These studies support reports that inhibition of bone resorption with bisphosphonates had an anti-myeloma effect.

Whereas the biology of osteoclasts in myeloma-associated lytic bone disease has been investigated intensively, little is known about the disease-associated changes in osteoblast activity and their underlying mechanisms. It has been suggested that in myeloma, the ability of mesenchymal stem cells to differentiate into the osteogenic lineage is impaired. However, the mechanisms responsible for such impairment have not been elucidated.

It has been shown that comparative global gene expression profiling (GEP) of bone marrow plasma cells from normal healthy donors and malignant bone marrow plasma cells from newly diagnosed multiple myeloma represented a powerful technique for identifying candidate disease genes and disrupted pathways involved in malignant transformation of multiple myeloma (Zhan et al., 2002).

The prior art is deficient in a comparative analysis to identify genes expressed in the malignant plasma cells that may be contributory to multiple myeloma bone diseases as well as methods to diagnose and treat multiple myeloma bone diseases. The present invention fulfills this longstanding need and desire in the art.

SUMMARY OF THE INVENTION

To identify the molecular determinants of lytic bone disease, the expression profiles of ~12,000 genes in CD138-enriched plasma cells from newly diagnosed multiple myeloma exhibiting no radiological evidence of lytic lesions (n=28) were compared to those with $\geq 3$ lytic lesions (n=47). Consistent with a critical role of WNT signaling in osteoblast differentiation, two secreted WNT signaling antagonists, soluble frizzled related protein 3 (SFRP-3/FRZB) and the human homologue of Dickkopf-1 (DKK-1), were expressed in 40 of 47 with lytic bone lesions, but only 16 of 28 lacking bone lesions (P<0.05). Immunohistochemistry showed high levels of DKK-1 and FRZB in plasma cells from cases with high gene expression. Importantly, DKK-1 and FRZB were not expressed in plasma cells from 45 normal bone marrow donors or 10 Waldenstrom's macroglobulinemia, a related plasma cells malignancy that lacks bone disease.

Serum derived from multiple myeloma patients with high DKK-1 blocked both Wnt signaling and osteoblast differentiation in vitro. Importantly, pre-incubation of the serum with DKK-1 and FRZB antibodies inhibited this function. Consistent with a key role for JUN in controlling DKK-1 expression and in turn apoptosis, plasma cells derived from extramedullary disease as well as primary refractory disease had low expression of JUN and DKK-1.

Multiple myeloma plasma cells showed a massive up-regulation of DKK-1 and FRZB gene expression after in vivo treatment. DKK-1 and FRZB can be upregulated in multiple myeloma plasma cells after treatment of patients with genotoxic drugs used to treat the disease, thus furthering a role for DKK-1 in multiple myeloma cell apoptosis. Primary multiple myeloma cells co-cultured with in vitro derived osteoclasts (OC) lacked apoptosis and that this was tightly correlated with the down-regulation of JUN, FOS, FOSB, and DKK-1.

Results disclosed in the present invention indicate that blocking the production and/or secretion of DKK-1 and FRZB may prevent or reverse bone loss in multiple myeloma patients. Further applications may include using DKK-1 and FRZB inhibitors to prevent bone loss in the general population. Additionally, Wnt signaling has recently been shown to be critical for the self renewal capacity of hematopoietic stem cells. Futhermore, a bone marrow niche required for HSC proliferation is formed by mature osteoblasts. The block to Wnt signaling by DKK1 and FRZB could directly and indirectly impair hepatic stellate cell (HSC) proliferation and thus may partly account for the immunosuppression and anemia seen in multiple myeloma. Thus blocking DKK1 and/or FRZB may also prevent or reverse the defect in hematopoeisis seen in most patients with myeloma.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1A shows clusterview of normalized expression levels of 57 genes identified by logistic regression analysis as being significantly differentially expressed in malignant plasma cells from patients with no (n=36) and 1+MRI focal lesions (n=137) (P<0.0001). The 28 genes exhibiting elevated expression in plasma cells from patients with 1+MRI lesions are ordered from top to bottom based on rank of significance. Likewise the 30 genes showing significant elevation in patients with no MRI-lesions are ordered from bottom to top based on significance rank. Gene symbols (Affymetrix probe set identifiers when the gene is unnamed) are listed to the left. Normalized expression scales range from −30 (blue) to +30 (red) as indicated below the data display. The four genes remaining significant after permutation adjustment are underlined.

FIG. 1B shows a bar graph of DKK1 gene expression in plasma cells from normal bone marrow (BPC), patients with monoclonal gammopathy of undetermined significance (MGUS), Waldenström's macroglobulinemia (WM), and multiple myeloma (MM) presented on the x-axis. MM samples are broken down into three bone lesion groups: no MRI/no x-ray lesions, 1+MRI/no x-ray lesions, and 1+MRI/1+x-ray lesions. The Affymetrix Signal, a quantitative measure of gene expression derived from MAS 5.01, is indicated on the y-axis. DKK1 gene expression level in each sample is indicated by a bar, with the height of the bar proportional to gene expression intensity. Samples are ordered from the lowest to highest DKK1 gene expression from left to right on the x-axis. The number of samples in each group is indicated below each group designator. Statistics for comparisons between the MM subgroups are indicated in the text.

FIG. 40A shows the expression of DKK1 mRNA was detected by microarray and DKK1 protein by ELISA in a total of 107 cases of newly diagnosed myeloma. Results of both assays were transformed by the log base 2 and normalized to give a mean of 0 and variance of 1. Each bar indicates the relative relationship of gene expression and protein expression in each sample. There was a significant correlation between DKK1 mRNA in myeloma plasma cells and protein in bone marrow plasma (r=0.65, P<0.001). FIG. 40B shows bar view of DKK1 protein levels in bone marrow plasma plasma cells from normal donors (BPC), patients with monoclonal gammopathy of undetermined significance (MGUS), Waldenström's macroglobulinemia (WM), and multiple myeloma (MM) are presented on the x-axis. MM samples are broken down into three bone lesion groups: no MRI/no x-ray lesions, 1+MRI/no x-ray lesions, and 1+MRI/1+x-ray lesions. The DKK1 protein concentration (ng/ml) is indicated on the y-axis. To enable comparisons of DKK1 protein levels in the lower ranges, 200 ng/ml was made the maximum value. This resulted in the truncation of a single sample with DKK1 concentration of 476 ng/ml. DKK1 protein level in each sample is indicated by a bar, with the height of the bar proportional to DKK1 protein levels. Samples are ordered from the lowest to highest DKK1 protein levels from left to right on the x-axis. The number of samples in each group is indicated below each group.

FIG. 41A shows alkaline phosphatase levels, a marker of osteoblast differentiation (y-axis) were measured in C2C12 cells after 5 days of culture in the presence of 5 percent fetal calf serum alone or with BMP2, BMP2+DKK1, BMP2+DKK1+anti-DKK1, or BMP-2+DKK1+polyclonal IgG. Each bar represents the mean (±SEM) of triplicate experiments. Note that activity of alkaline phosphatase increased in the presence of BMP-2 and significant reduction of this protein by co-incubation with recombinant DKK1. Also note that anti-DKK1 antibody, but not polyclonal IgG can block the repressive activity of DKK1. FIG. 41B shows alkaline phosphatase levels (y-axis) were tested in C2C12 cells after culturing these cells for 5 days in 5 percent fetal calf serum alone or 50 ng/ml BMP-2+10 percent normal bone marrow plasma (NS) or BMP-2+10 percent myeloma bone marrow plasma from 10 patients with newly diagnosed myeloma (sample identified provided), or BMP2+10 percent myeloma patient plasma +anti-DKK1 or goat polyclonal IgG. Each bar represents the mean (±SEM) of triplicate experiments. DKK1 concentration from each bone marrow plasma samples was determined by ELISA and final concentrations in culture after 1:10 dilution are indicated on the x-axis. Note that samples with >12 ng/ml DKK1 had an effect on alkaline phosphatase production. A star indicates P<0.05 in comparison to alkaline phosphatase in BMP2+10 percent normal human bone marrow plasma.

DETAILED DESCRIPTION OF THE INVENTION

Figure 1A:
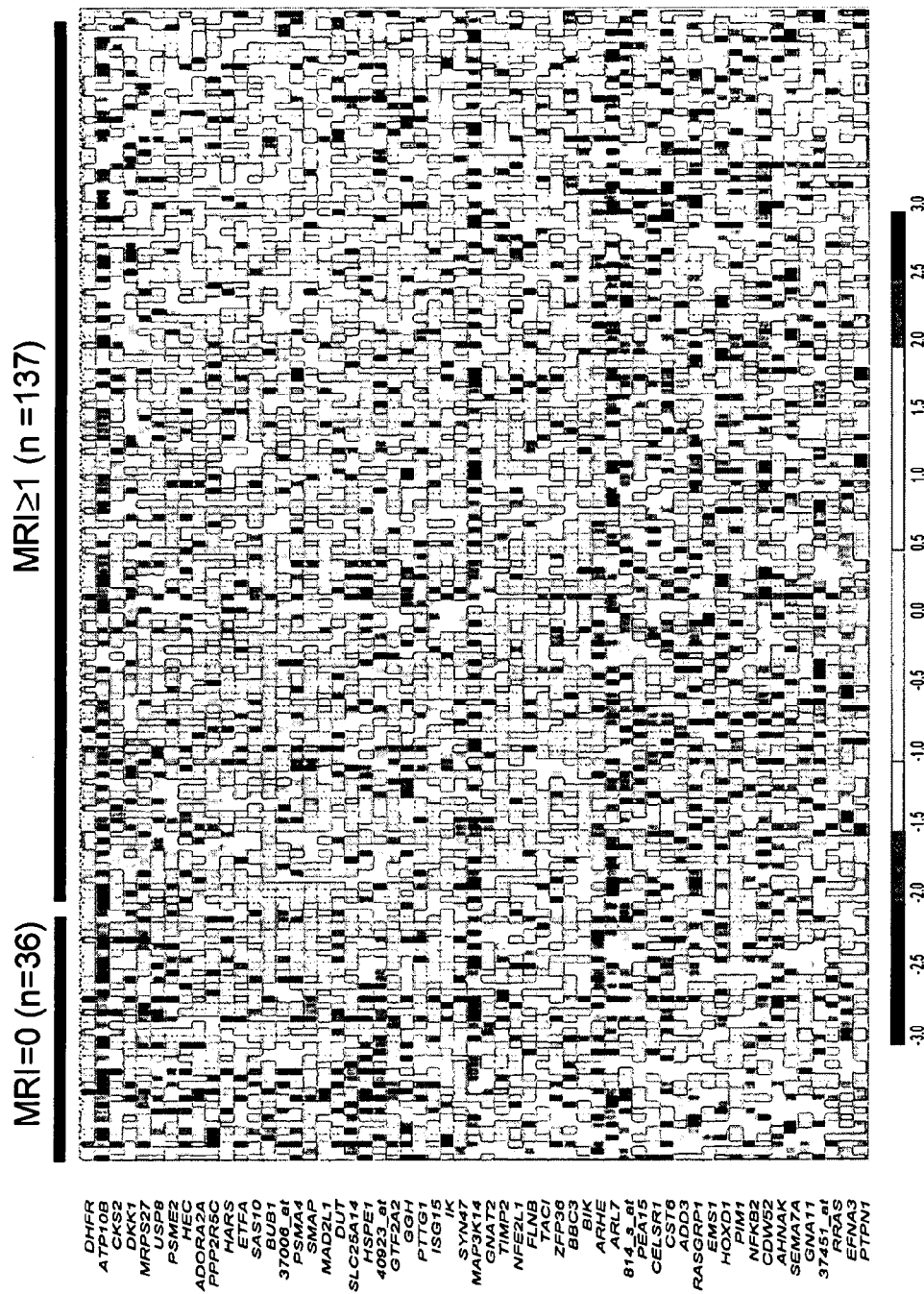
FIGS. 1A and 1B show global gene expression patterns reflecting bone lesions in myeloma.

The present invention demonstrates that the secreted WNT signaling antagonists DKK-1 and FRZB mediate bone destruction seen in multiple myeloma. Together with emerging evidence of an absolute requirement of Wnt signaling in osteoblast growth and differentiation, these data strongly implicate these factors in causing osteoblast anergy and contributing to multiple myeloma bone disease by suppressing the normal compensatory bone production that follows bone loss.

The role of multiple myeloma plasma cells in stimulating osteoclast activity has been intensely investigated and several key links established. Data presented herein provide for the first time evidence of a possible mechanistic explanation of osteoblast dysfunction in multiple myeloma. These are significant observations in that recent studies have shown that inhibition of WNT signaling causes defects in osteoblast function. The secreted DKK-1 and FRZB could account for both the systemic osteoporosis seen in multiple myeloma as well as the exaggerated local bone destruction proximal to plasma cells foci.

Importantly, DKK-1 and FRZB act to inhibit WNT signaling through independent mechanisms, indicating that their co-expression may have synergistic effects. Thus, these genes could be used to predict extent of bone disease and future risk of developing bone disease. Moreover, inhibitors of these proteins could be used to block bone disease. It is also possible that these factors play a role in osteoporosis in the general population.

WNT Signaling Pathway

Wnt genes comprise a large family of secreted polypeptides that are expressed in spatially and tissue-restricted patterns during vertebrate embryonic development. Mutational analysis in mice has shown the importance of Wnts in controlling diverse developmental processes such as patterning of the body axis, central nervous system and limbs, and the regulation of inductive events during organogenesis. The Wnt family of secreted growth factors initiates signaling via the Frizzled (Fz) receptor and its coreceptor, LDL receptor-related protein 5 or 6 (LPR5 or LRP6), presumably through Fz-LPR5/LRP6 complex formation induced by Wnt.

Secreted antagonists of Wnt include Frizzled (Fz)-related proteins (FRPs), Cerberus, Wnt inhibitory factor (WIF) and Dickkopf (DKK). Frizzled (Fz)-related proteins, Cerberus and Wnt inhibitory factor have all been shown to act by binding and sequestering Wnt. Unlike Wnt antagonists which exert their effects by molecular mimicry of Fz or Wnt sequestration through other mechanisms, Dickkopf-1 (DKK-1) specifically inhibits canonical Wnt signalling by binding to the LPR5/LRP6 component of the receptor complex.

DKK-1 is a head inducer secreted from the vertebrate head organizer and induces anterior development by antagonizing Wnt signaling. DKK-1 is a high-affinity ligand for LRP6 and inhibits Wnt signaling by preventing Fz-LRP6 complex formation induced by Wnt. DKK-1 binds neither Wnt nor Fz, nor does it affect Wnt-Fz interaction. DKK-1 function in head induction and Wnt signaling inhibition strictly correlates with its ability to bind LPR5/LRP6 and to disrupt the Fz-LPR5/LRP6 association. LPR5/LRP6 function and DKK-1 inhibition appear to be specific for the Wnt/Fz beta-catenin pathway. These findings thus reveal a novel mechanism for Wnt signal modulation.

WNT Signaling and Osteoblast Differentiation

Recent studies have shown that the Wnt signaling pathway is critical for osteoblast differentiation and function. Mice with a targeted disruption in the gene for low-density lipoprotein receptor-related protein 5 (LRP5) developed a low bone mass phenotype. LRP5 is expressed in osteoblasts and is required for optimal Wnt signaling in osteoblasts. In vivo and in vitro analyses indicated that this phenotype becomes evident postnatally, and it was secondary to decreased osteoblast proliferation and function in a Cbfa1-independent manner.

In human, mutations in LRP5 cause the autosomal recessive disorder osteoporosis-pseudoglioma syndrome (OPPG). Osteoporosis-pseudoglioma syndrome carriers have reduced bone mass when compared to age- and gender-matched controls.

Importantly, separate and distinct mutations in LRP result in a high bone mass phenotype. In contrast to the osteoporosis-psuedoglioma mutations, the high bone mass traits are gain of function mutations. Markers of bone resorption were normal in the affected subjects, whereas markers of bone formation such as osteocalcin were markedly elevated. Levels of fibronectin, a known target of signaling by Wnt, were also elevated. In vitro studies showed that the normal inhibition of Wnt signaling by Dickkopf-1 (DKK-1) was defective in the presence of the mutation and that this resulted in increased signaling due to unopposed Wnt activity. These findings demonstrated the role of altered LRP5 function in high bone mass and point to DKK as a potential target for the prevention or treatment of osteoporosis.

WNT Signaling and Bone Disease in Multiple Myeloma

Indirect evidence of a role of DKK-1 in osteoblast function has been provided by identification of gain of function mutations in LRP-5 being linked to a high bone mass phenotype. In addition, targeted disruption of secreted firzzled-related protein (SFRP-1), a homologue of FRZB (SFRP-3), leads to decreased osteoblast and osteocyte apoptosis and increased trabecular bone formation.

A quantitative trait loci (QTL) influencing bone mass has been localized to the LRP-5 region, suggesting that the population at large have different risk of developing osteoporosis. It is conceivable that multiple myeloma bone disease may be influenced by the combined effects of DKK-1/FRZB expression with an inherited predisposition to low bone mass conferred by inherited LRP-5 alleles. Multiple myeloma cases may be genotyped for LRP-5 allele variations and correlate this information with bone disease, and DKK-1 and FRZB expression.

Monoclonal gammopathy of undetermined significance (MGUS), a plasma cell dyscrasia that is predisposed to develop into multiple myeloma, is differentiated from multiple myeloma by the lack of obvious bone disease. The significance of discovering DKK-1 and/or FRZB expression in a third of monoclonal gammopathy of undetermined significance is unclear but could suggest that these cases may be at higher risk for developing multiple myeloma. As with multiple myeloma, this predisposition may also be related to inherited LRP5 alleles. Alternatively, these monoclonal gammopathy of undetermined significance cases could have underlying preclinical bone disease that is not yet apparent by radiological scans.

Data presented herein suggests a model for how DKK-1 expression by multiple myeloma plasma cells can be linked to multiple myeloma disease growth control and bone destruction and how these two phenomena can be integrated by one molecule. In the model, primary multiple myeloma express high levels of DKK and these levels can be increased with drug therapies used to treat the disease. High levels of DKK-1 likely induce apoptosis of multiple myeloma cells and could explain the relatively slow progression of the disease in its early phase as cell growth is tempered by high rate of DKK-1 induced apoptosis. However, as the disease progresses there is an osteoclast-induced reduction in JUN and DKK-1 that eventually develops into a constitutive loss of JUN and DKK-1 expression as seen in extramedullary disease.

Thus, if one were to view DKK-1 expression from the perspective of the multiple myeloma plasma cells, high levels of DKK-1 expression could be seen as positive feature of the disease. However, with the mesenchymal cell lineage being exquisitely sensitive to DKK-1 induced apoptosis, the high levels of this secreted product likely has a double edge to it in that it also induces massive programmed cell death of osteoblast precursors and possibly even mesenchymal stem cells. It is expected that high levels of DKK-1 early in the disease could lead to a permanent loss of mesenchymal stem cells, a notion supported by the observed lack of bone repair after remission induction or during disease progression when osteoclasts likely suppress DKK-1 secretion by multiple myeloma plasma cells. Thus, exploitation of this knowledge might lead to the development of new therapies for multiple myeloma that accentuate DKK-1's effects on multiple myeloma plasma cells, but at the same time prevent DKK's bone damaging effects on osteoblast or their precursors.

In one embodiment of the present invention, there is provided a method of determining the potential of developing a bone disease in a multiple myeloma patient by examining the expression level of WNT siganling antagonist. Increased expression of the antagonist compared to that in normal individual would indicate that the patient has the potential of developing bone disease. Preferably, the WNT signaling antagonist is soluble frizzled related protein 3 (SFRP-3/FRZB) or the human homologue of Dickkopf-1 (DKK1). In general, the expression levels of these proteins can be determined at the nucleic acid or protein level.

In another embodiment, there is provided a method of treating bone disease in a multiple myeloma patient by inhibiting the expression of WNT signaling antagonist. Preferably, the WNT signaling antagonist is soluble frizzled related protein 3 (SFRP-3/FRZB) or the human homologue of Dickkopf-1 (DKK1). In general, the expression of these antagonists can be inhibited at the nucleic acid or protein level.

In yet another embodiment, there is provided a method of preventing bone loss in an individual by inhibiting the expression of WNT signaling antagonist. Preferably, the WNT signaling antagonist is soluble frizzled related protein 3 (SFRP-3/FRZB) or the human homologue of Dickkopf-1 (DKK1). In general, the expression of these antagonists can be inhibited at the nucleic acid or protein level.

In yet another embodiment, there is provided a method of controlling bone loss in an individual, comprising the step of inhibiting the expression of the DKK1 gene (accession number NM012242) or the activity of the protein expressed by the DKK1 gene. The DKK1 gene expression is inhibited by any method known to a person having ordinary skill in this art including, e.g., anti-sense oligonucleotides or by anti-DKK1 antibodies or soluble LRP receptors.

In yet another embodiment, there is provided a method of controlling bone loss in an individual, comprising the step of administering to said individual a pharmacological inhibitor of DKK1 protein. Generally, this method would be useful where the individual has a disease such as multiple myeloma, osteoporosis, post-menopausal osteoporosis or malignancy-related bone loss. Generally, the malignancy-related bone loss is caused by breast cancer metastasis to the bone or prostate cancer metastasis to the bone.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Patients 174 patients with newly diagnosed multiple myeloma, 16 patients with monoclonal gammopathy of undetermined significance, 9 with Waldenström's macroglobulinemia, and 45 normal persons were studied. The Institutional Review Board of the University of Arkansas for Medical Sciences approved the research studies and all subjects provided written informed consent. Table 1 shows the characteristics of the patients with multiple myeloma.

TABLE 1

Myeloma patient characteristics and their relationship to MRI lesions

| Variable | n/N | % | MRI = 1+ | MRI = 0 | P value |
|---|---|---|---|---|---|
| Age ≧ 65 yr | 23/169 | 14 | 17/132 (12.9%) | 6/36 (16.7%) | 0.59* |
| Caucasian | 147/169 | 87 | 113/132 (85.6%) | 33/36 (91.7%) | 0.42* |
| Female | 68/169 | 40 | 55/132 (41.7%) | 13/36 (36.1%) | 0.55 |
| Kappa light chain | 104/165 | 63 | 79/128 (61.7%) | 24/36 (66.7%) | 0.59 |
| Lambda light chain | 61/165 | 37 | 49/128 (38.3%) | 12/36 (33.3%) | 0.59 |
| IgA subtype | 39/169 | 23 | 25/132 (18.9%) | 14/36 (38.9%) | 0.012 |
| B2M ≧ 4 mg/L | 60/169 | 36 | 47/132 (35.6%) | 13/36 (36.1%) | 0.96 |
| CRP ≧ 4 mg/L | 12/166 | 7 | 11/129 (8.5%) | 1/36 (2.8%) | 0.47* |
| Creatinine ≧ 2 mg/dL | 19/169 | 11 | 16/132 (12.1%) | 3/36 (8.3%) | 0.77* |
| LDH ≧ 190 UI/L | 52/169 | 31 | 44/132 (33.3%) | 8/36 (22.2%) | 0.20 |
| Albumin < 3.5 g/dL | 23/169 | 14 | 19/132 (14.4%) | 4/36 (11.1%) | 0.79* |
| Hgb < 10 g/dL | 40/169 | 24 | 31/132 (23.5%) | 8/36 (22.2%) | 0.87 |

TABLE 1-continued

Myeloma patient characteristics and their relationship to MRI lesions

| Variable | n/N | % | MRI = 1+ | MRI = 0 | P value |
|---|---|---|---|---|---|
| PCLI ≧ 1% | 23/150 | 15 | 18/119 (15.1%) | 4/30 (13.3%) | 1.00* |
| ASPC ≧ 33% | 109/166 | 66 | 82/129 (63.6%) | 26/36 (72.2%) | 0.33 |
| BMPC ≧ 33% | 104/166 | 63 | 79/129 (61.2%) | 24/36 (66.7%) | 0.55 |
| Cytogenetic abnormalities | 52/156 | 33 | 45/121 (37.2%) | 6/34 (17.6%) | 0.032 |
| CA13 or hypodiploid | 33/52 | 63 | 31/121 (25.6%) | 3/34 (8.8%) | 0.037 |
| Other CA | 19/52 | 37 | 53/103 (51.5%) | 16/32 (50.0%) | 0.89 |
| FISH13 | 69/136 | 51 | 103/136 (75.7%) | 28/36 (77.8%) | 0.80 |
| Osteopenia | 131/173 | 76 | | | |
| 1+ Lesions by MRI | 137/173 | 79 | | | |
| 3+ Lesions by MRI | 108/173 | 62 | | | |
| 1+ Lesions by X-ray | 105/174 | 60 | | | |
| 3+ Lesions by X-ray | 69/174 | 40 | | | |

*Fisher's Exact test, otherwise Chi-square test

EXAMPLE 2

Bone Imaging

Images were reviewed, without prior knowledge of gene expression data, using a Canon PACS (Picture Archiving and Cataloging System). MRI scans were performed on 1.5 Tesla GE Signa™ scanners. X-rays were digitized from film in accordance with American College of Radiology standards. MRI scans and x-rays were linked to the Canon PACS system using the ACR's DICOM (Digital Imaging and Communications in Medicine) standard. Imaging was done in accordance with manufacturers' specifications. MRI images were created with pre- and post-gadolinium T1-weighting and STIR (short-tau inversion recovery) weighting.

EXAMPLE 3

Plasma Cell Isolation and Gene Expression Profiling

Following Ficoll-Hypaque gradient centrifugation, plasma cells obtained from the bone marrow were isolated from the mononuclear cell fraction by immunomagnetic bead selection using a monoclonal mouse anti-human CD138 antibody (Miltenyi-Biotec, Auburn, Calif.). More than 90 percent of the cells used for gene expression profiling were plasma cells, as shown by two-color flow cytometry using $CD138^+/CD45^-$ and $CD38^+/CD45^-$ markers, the presence of cytoplasmic immunoglobulin light chains by immunocytochemistry, and morphology by Wright-Giemsa staining. Total RNA was isolated with RNeasy Mini Kit (Qiagen, Valencia, Calif.). Preparation of labeled cRNA and hybridization to U95Av2 microarrays containing approximately 10,000 genes (Affymetrix, Santa Clara, Calif.) was performed as previously described (Zhan et al., 2002; Zhan et al., 2003). RNA amplification was not required.

EXAMPLE 4

Immunohistochemistry

An antibody from a goat that was immunized against the entire human DKK1 protein (R&D Systems, Minneapolis, Minn.) was diluted 1:200 in Tris-buffer and added to formalin-fixed, paraffin-embedded bone marrow biopsy sections for 2 hours at room temperature. Adjacent sections were stained with H & E. Antigen-antibody reactions were developed with DAB (after biotinylated anti-goat antibody [Vector Laboratories, Burlingame, Calif.] [1:400 dilution] and streptavidin-horse radish peroxidase [Dako] staining), and counterstained with Hematoxylin-2.

EXAMPLE 5

Enzyme Linked Immunosorbent Assay (ELISA)

Nunc-Immuno MaxiSorp surface microtiter plates were coated with 50 ml of anti-DKK1 antibody at 1 mg/ml in 1× phosphate buffered saline, pH 7.2 at 4° C. overnight, and blocked with 4 percent bovine serum albumin. Bone marrow plasma was diluted 1:50 in dilution buffer (1× phosphate buffered saline +0.1 Tween-20+1 percent bovine serum albumin). A total of 50 µl was loaded per well and incubated overnight at 4° C., washed and incubated with biotinylated goat anti-human DKK1 IgG (R&D Systems) diluted to 0.2 mg/ml in dilution buffer, followed by addition of 50 µl of 1:10,000 dilution of streptavidin-horse radish peroxidase (Vector Laboratories), all according to manufacturer's recommendations. Color development was achieved with the OPD substrate system (Dako) based on manufacturer's instructions. Serial dilutions of recombinant human DKK1 (R&D Systems) were used to establish a standard curve. The cell line T293, which does not express endogenous DKK1 and T293 with stably transfected DKK1 (Fedi, et al., 1999) were used to validate the ELISA assay.

EXAMPLE 6

Osteoblast Differentiation Assays

C2C12 mesenchymal precursor cells (American Type Tissue Culture, Reston, Va.) were cultured in DMEM (Invitrogen, Carlsbad, Calif.) supplemented with 10 percent heat-inactivated fetal calf serum. Alkaline phosphatase activity in C2C12 cells was measured as described (Gallea, et al., 2001; Spinella-Jaegle, et al., 2001). Cell lysates were analyzed for protein content using the micro-BCA assay kit (Pierce, Rockford, Ill.). Each experiment was done in triplicate.

EXAMPLE 7

Statistical Analyses

Bone disease in multiple myeloma patients was modeled using logistic regression. Independent variables considered were gene expression intensity values (average difference calls) from ~10,000 genes (12,625 probe sets) measured using version 5.01 MAS (Affymetrix, Santa Clara, Calif.) from 174 cases of newly diagnosed multiple myeloma. The "Signal", a quantitative measure of gene expression, for each probe set was transformed to $\log_2$ before entry into the logistic regression model and permutation-adjustment analysis. There was no prior hypothesis with regard to genes that might be associated with bone disease in myeloma. As a result a univariate model of bone disease for each of the 12,625 probe sets was used. Candidate genes were refined using t-tests with permutation-adjusted significance levels (Westfall and Young, 1993). The Westfall and Young analysis was used to adjust for the multiple univariate hypothesis tests. Group differences in DKK1 signal and DKK1 protein levels were tested using the Wilcoxon rank sum test. Significant differences in patient characteristics by status of bone disease were tested using either the Fisher's exact test or the chi-square test. Expression intensities of genes identified by logistic regression were visualized with Clusterview (Golub, et. al., 1999). Spearman's correlation coefficient was used to measure correlation of gene expression and protein levels. Significant differences, in osteoblast differentiation, between the control and each experimental condition were tested using the Wilcoxon rank sum test; separate comparisons were made for each unique C2C12 experiment. Two-sided p-values less than 0.05 were considered significant and two-sided p-values less than 0.10 were considered marginally significant.

EXAMPLE 8

Gene Expression Profiling of Myeloma Cells

Figure 1B:
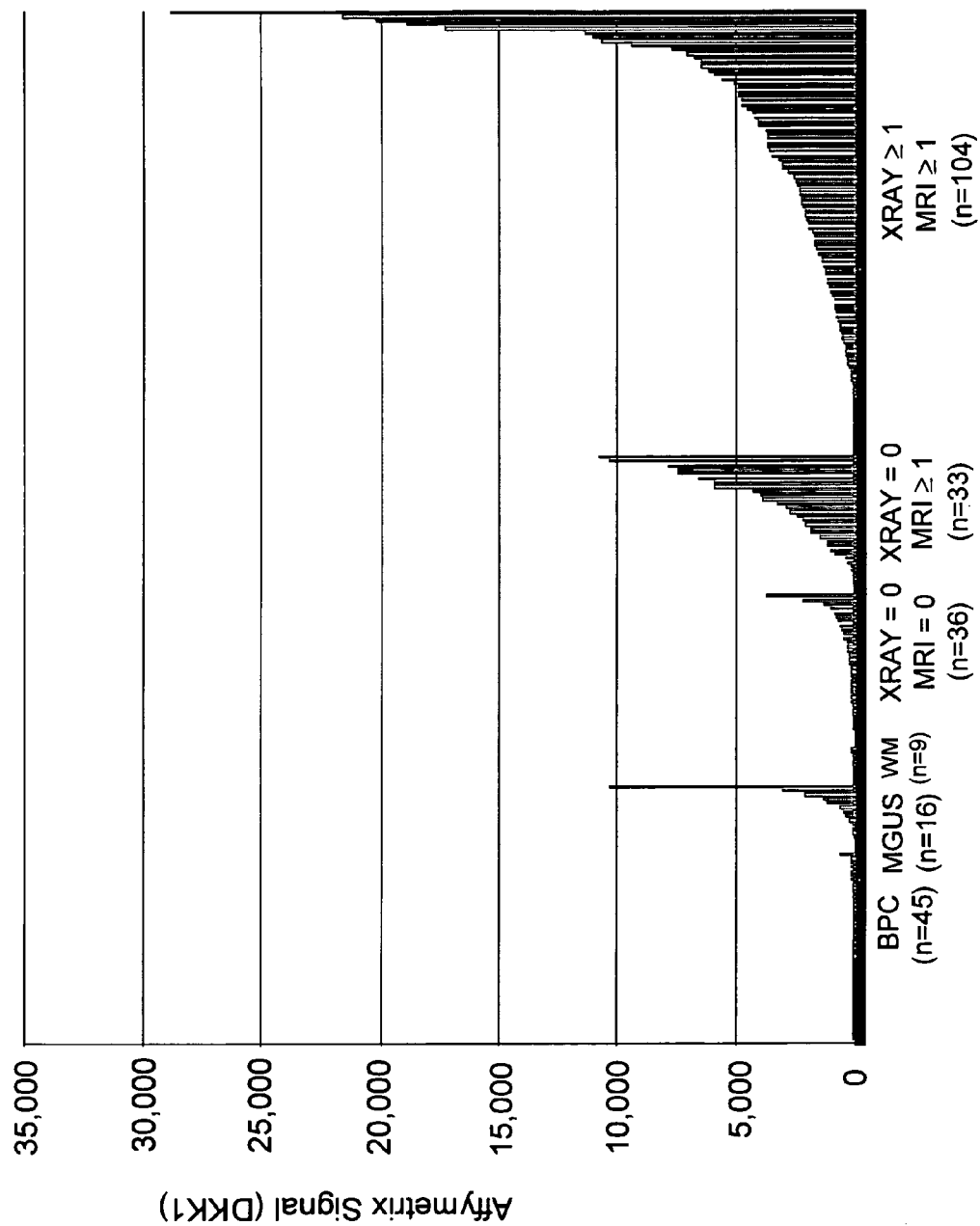

To identify genes that were overexpressed and associated with the presence of bone lesions, comparing microarray data from patients with or without bone lesions were performed. As MRI-defined focal lesions of bone can occur before radiologically identifiable lytic lesions, T1-weighted and STIR-weighted imaging to evaluate bone lesions were used. The gene expression patterns of approximately 10,000 genes in purified plasma cells from the marrow of patients with no bone lesions (n=36) and those with 1 or more (1+) MRI-defined focal lesions (n=137) were modeled by logistic regression analysis. The model identified 57 genes that were expressed differently (P<0.0001) in the two groups of patients (FIG. 1A). These 57 genes were further analyzed by t-tests with permutation-adjusted significance (Westfall and Young, 1993). These statistical tests showed that 4 of the 57 genes were overexpressed in patients with 1+MRI lesions: dihydrofolate reductase (DHFR), proteasome activator subunit (PSME2), CDC28 protein kinase 2 (CKS2), and dickkopf homolog 1 (DKK1). Given that the gene for the Wnt/β-catenin signaling antagonist DKK1 is the only one of the four that codes for a secreted factor and that Wnt/β-catenin signaling is implicated in bone biology, further tests on DKK1 were carried out. An analysis of the results from the 173 patients with myeloma showed that DKK1 signal for patients with 1+MRI and no x-ray lesions differ significantly compared to patients with no MRI and no x-ray lesions (median signal: 2,220 vs. 285; p<0.001) but does not differ significantly compared to patients with 1+MRI and 1+x-ray (median signal: 2,220 vs. 1,865; p=0.63) (FIG. 1B, Table 2).

Monoclonal gammopathy of undetermined significance (MGUS) is a plasma cell dyscrasia without lytic bone lesions and can precede multiple myeloma. In 15 of 16 cases of MGUS, DKK1 was expressed by bone marrow plasma cells at levels comparable to those in multiple myeloma with no MRI or x-ray lesions of bone (FIG. 1B). DKK1 was undetectable in plasma cells from 45 normal donors, and 9 patients with Waldenström's macroglobulinemia a plasma cell malignancy of the bone lacking bone lesions (FIG. 1B).

TABLE 2

DKK1 mRNA and protein levels in MRI/X-ray-lesion defined subgroups of MM

|  |  | No MRI/<br>No X-ray | 1 + MRI/<br>No X-ray | 1 + MRI/<br>1 + X-ray |
|---|---|---|---|---|
|  | N | 36 | 33 | 104 |
| DKK1<br>(Signal)<br>(mRNA) | Mean<br>(Std) | 536.1<br>(720.7) | 3146.5<br>(3079.9) | 3415.1<br>(4870.8) |
| DKK1<br>(Signal)<br>(protein) | Min,<br>Median,<br>Max | 19.2,<br>284.9,<br>3810.2 | 16.4,<br>2220.2,<br>10828.4 | 9.4, 1864.7,<br>28859.1 |

TABLE 2-continued

DKK1 mRNA and protein levels in MRI/X-ray-lesion defined subgroups of MM

|  |  | N | 18 | 9 | 41 |
|---|---|---|---|---|---|
| DKK1 (ng/ml) (mRNA) | Mean (Std) |  | 9.0 (4.7) | 24.0 (17.7) | 34.3 (75.3) |
| DKK1 (ng/ml) (protein) | Min, Median, Max |  | 1.8, 8.7, 19.7 | 7.4, 20.4, 61.8 | 2.5, 13.5, 475.8 |

EXAMPLE 9

Global Gene Expression Reveals DKK-1 and FRZB Linked to Lytic Bone Lesion in Multiple Myeloma In order to further identify the molecular determinants of lytic bone disease, the expression profiles of ~12,000 genes in CD138-enriched plasma cells from newly diagnosed multiple myeloma patients exhibiting no radiological evidence of lytic lesions on bone surveys (n=28) were compared to those with $\geq$3 lytic lesions (n=47). The Chi-square test of absolute calls (a qualitative measure of gene expression) was used to identify 30 genes that distinguished the two forms of disease (P<0.05). The Wilcoxon Rank Sum (WRS) test of the signal call (a quantitative measure of gene expression) revealed that 104 genes (49 up- and 55 down-regulated) differentiated the two disease subtypes (P<0.001).

Figure 2:
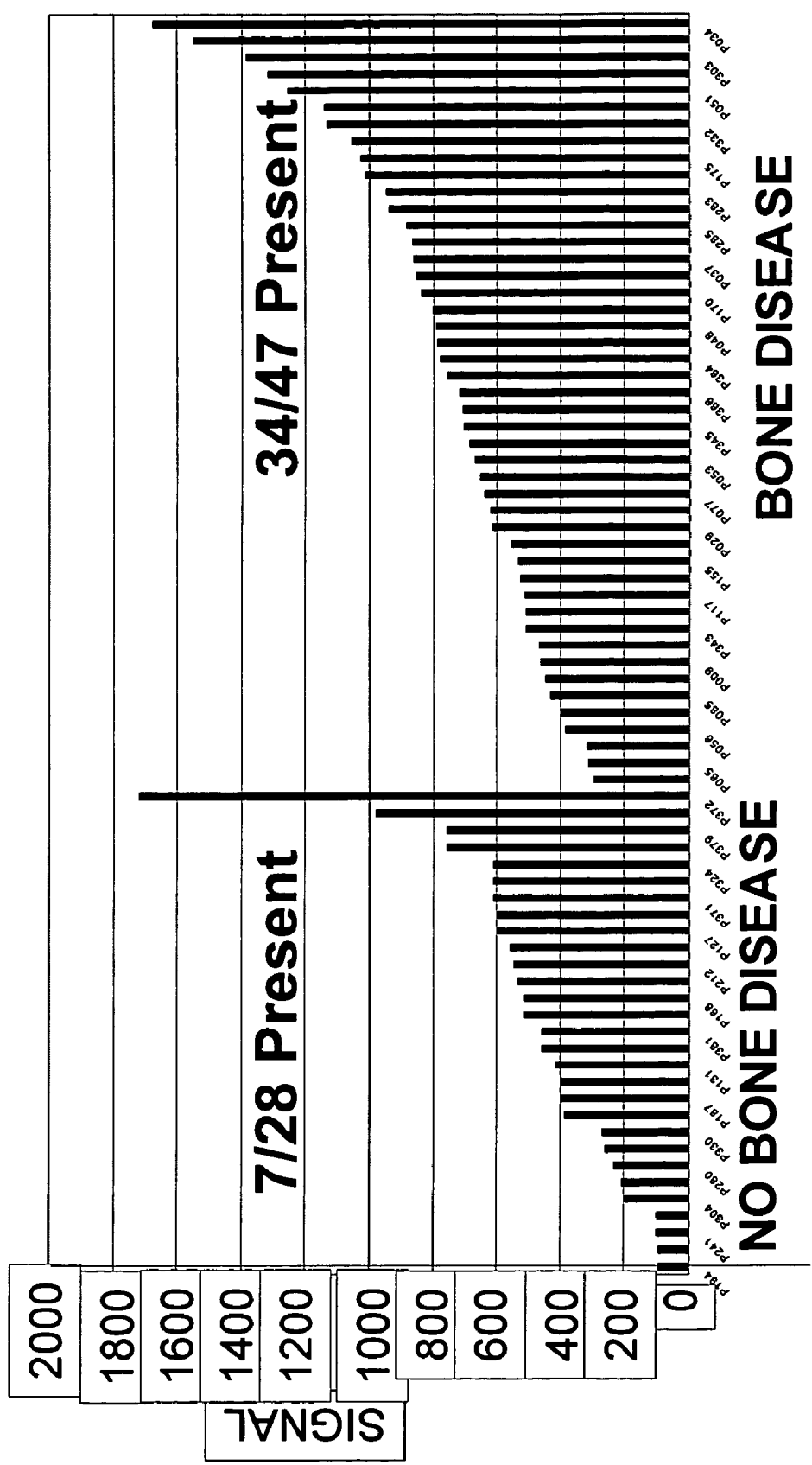
FIG. 2 shows RHAMM was up-regulated in multiple myeloma patients with bone lesions.
Figure 3:
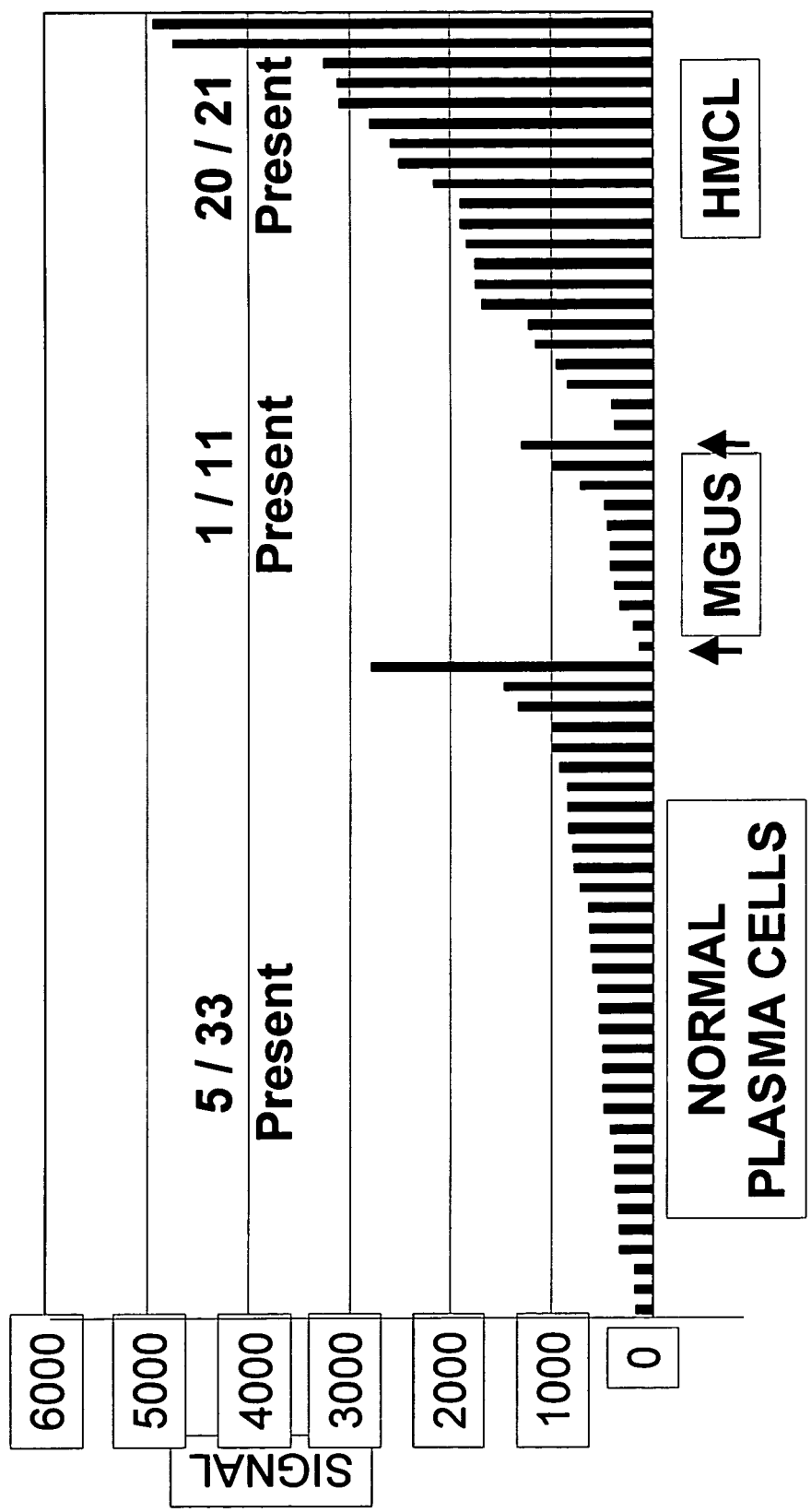
FIG. 3 shows RHAMM rarely present in normal plasma cells and monoclonal gammopathy of undetermined significance (MGUS), but it was present in virtually all human myeloma cell lines.

The Chi-square test identified the RHAMM proto-oncogene as the most significant discriminator between the two groups. It was expressed in only 7 of 28 patients with no bone disease compared with 34 of 47 patients with bone disease (FIG. 2). As expected, plasma cells from only 1 of 11 monoclonal gammopathy of undetermined significance expressed RHAMM (FIG. 3). WRS ranked RHAMM as the $14^{th}$ most significant discriminator between the lytic lesion group and no lytic lesion group. NCALD, a calcium binding protein involved in neuronal signal transduction, was present in 11/28 (40%) of no lytic lesion group but only in 2/47 (4%) lytic lesion group. Other notable genes identified by Chi-square analysis included FRZB, an antagonist of Wnt signaling, that was present in 40/47 (85%) of lytic lesion group and 15/28 (53%) of no lytic lesion group. CBFA2/AML1B has been linked to MIP1α expression and was present in 50% of the no lytic lesion group and in 79% of the lytic lesion group.

Figure 4:
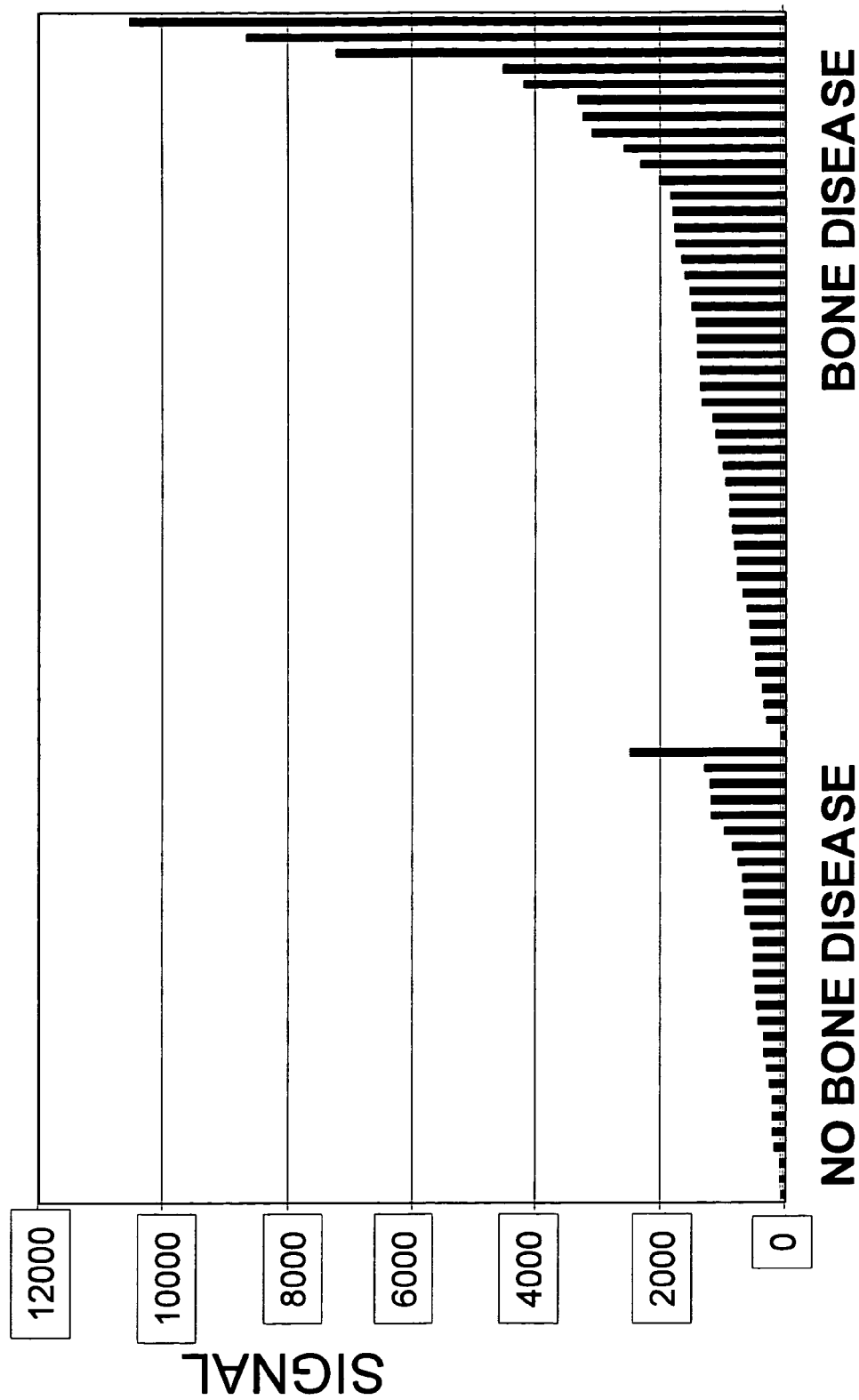
FIG. 4 shows securin was up-regulated in multiple myeloma patients with bone disease.
Figure 5:
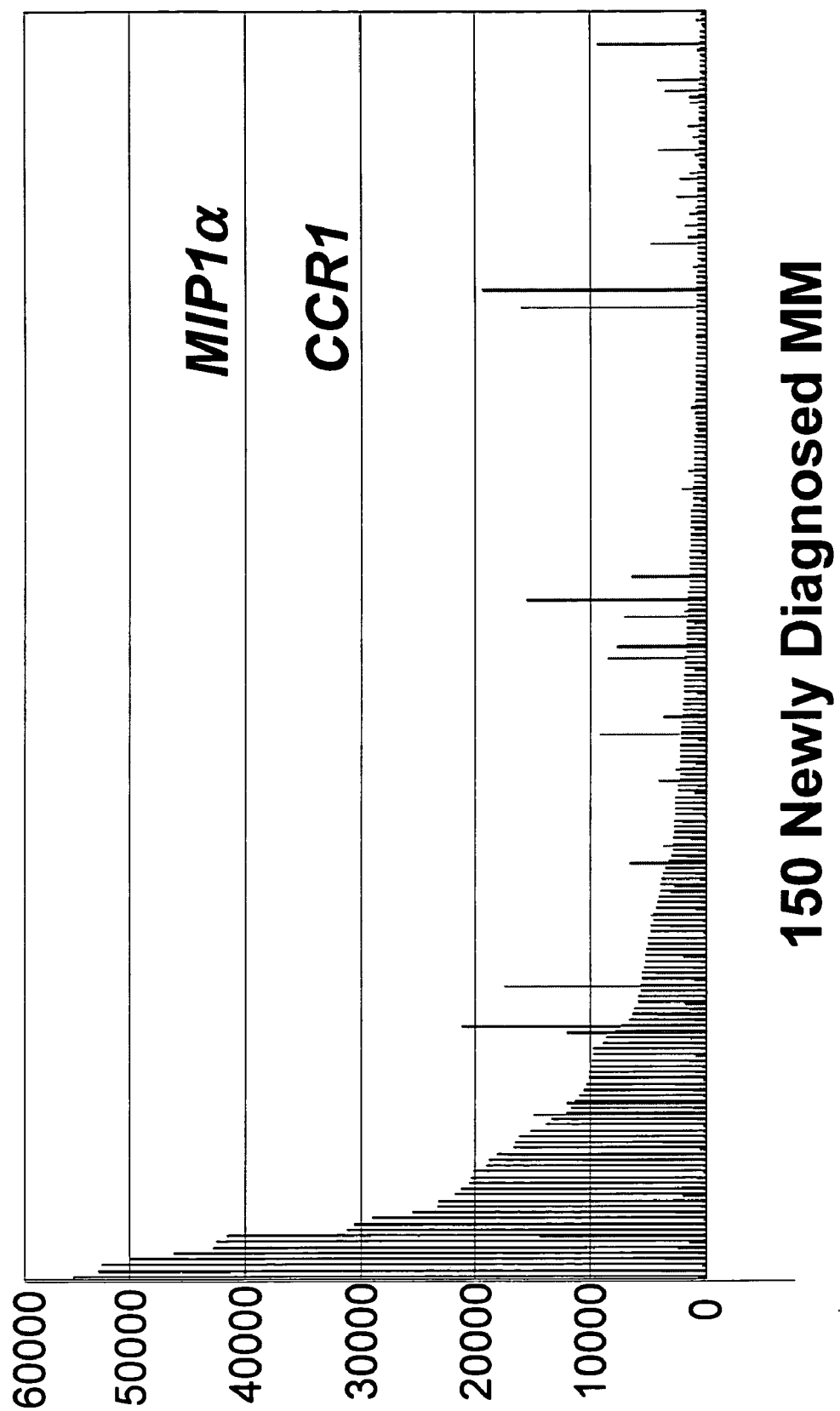
FIG. 5 shows MIP-1α and CCR1 were "spike" genes in multiple myeloma, but they were not correlated with lytic lesions. Black bar: CCR1; gray bar: MIP-1α.
Figure 6:
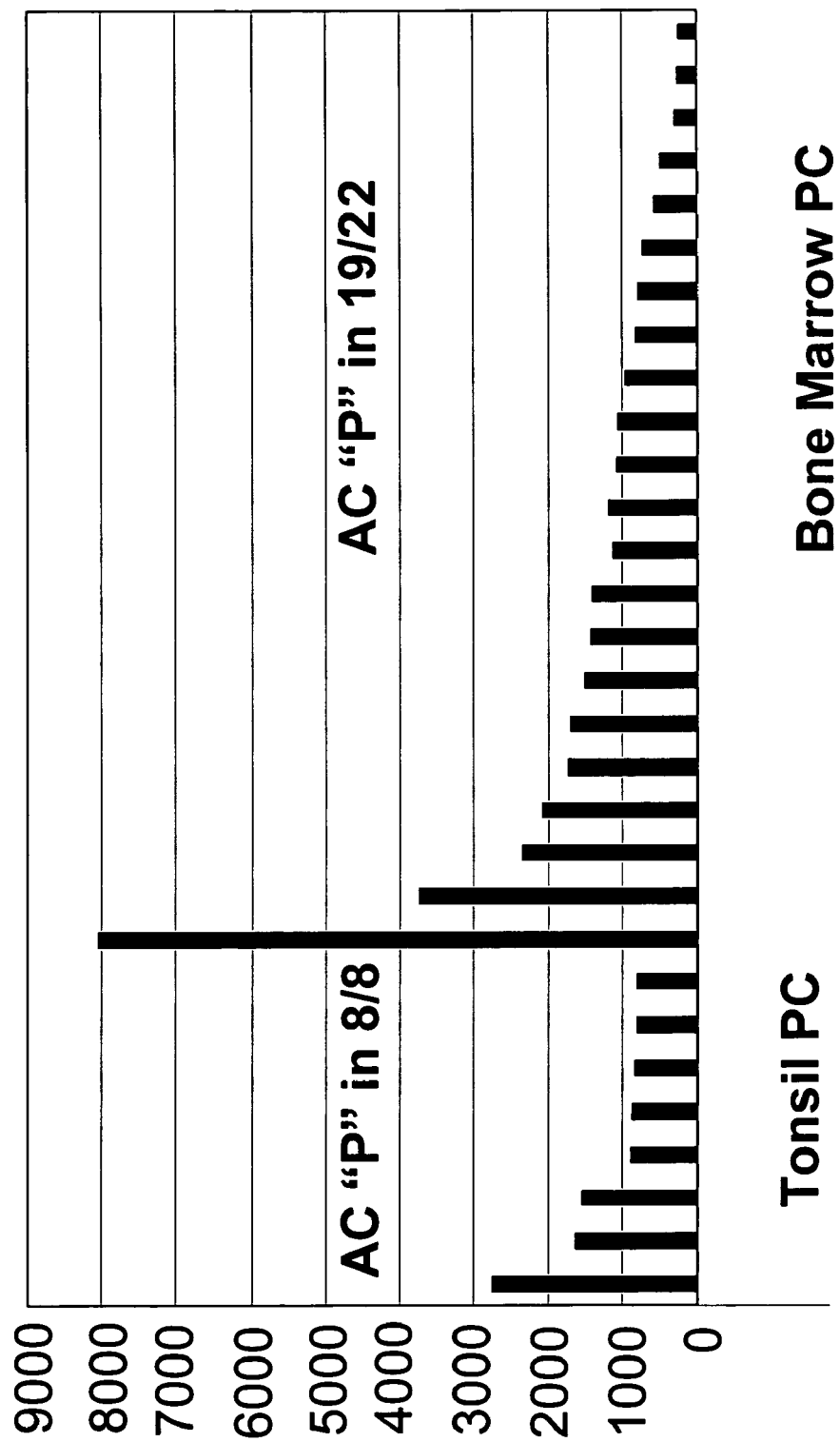
FIG. 6 shows MIP-1α was expressed at low level in normal plasma cells (PC).
Figure 7:
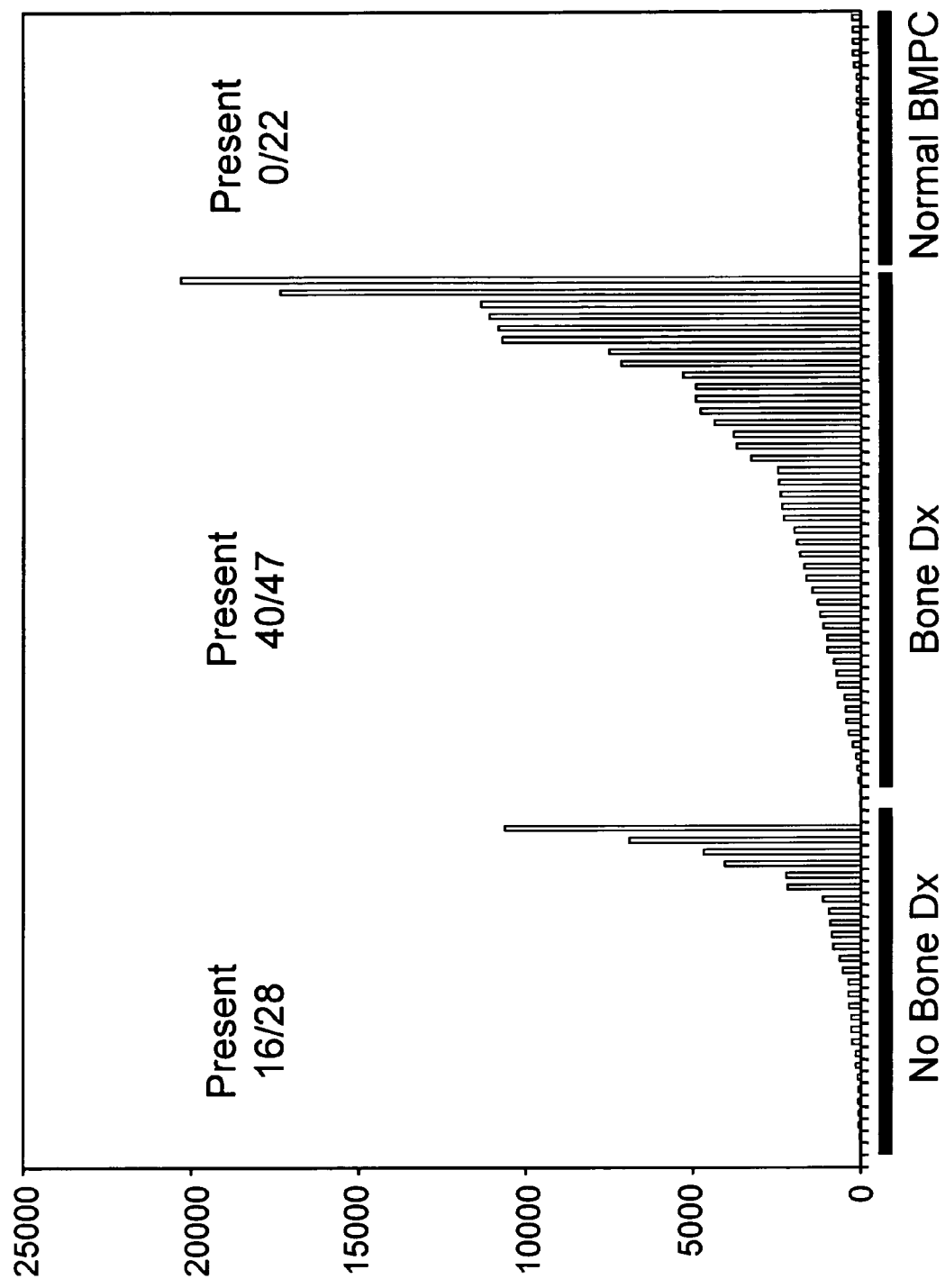
FIG. 7 shows the expression of WNT antagonist DKK-1 in multiple myeloma with bone lesions.
Figure 8:
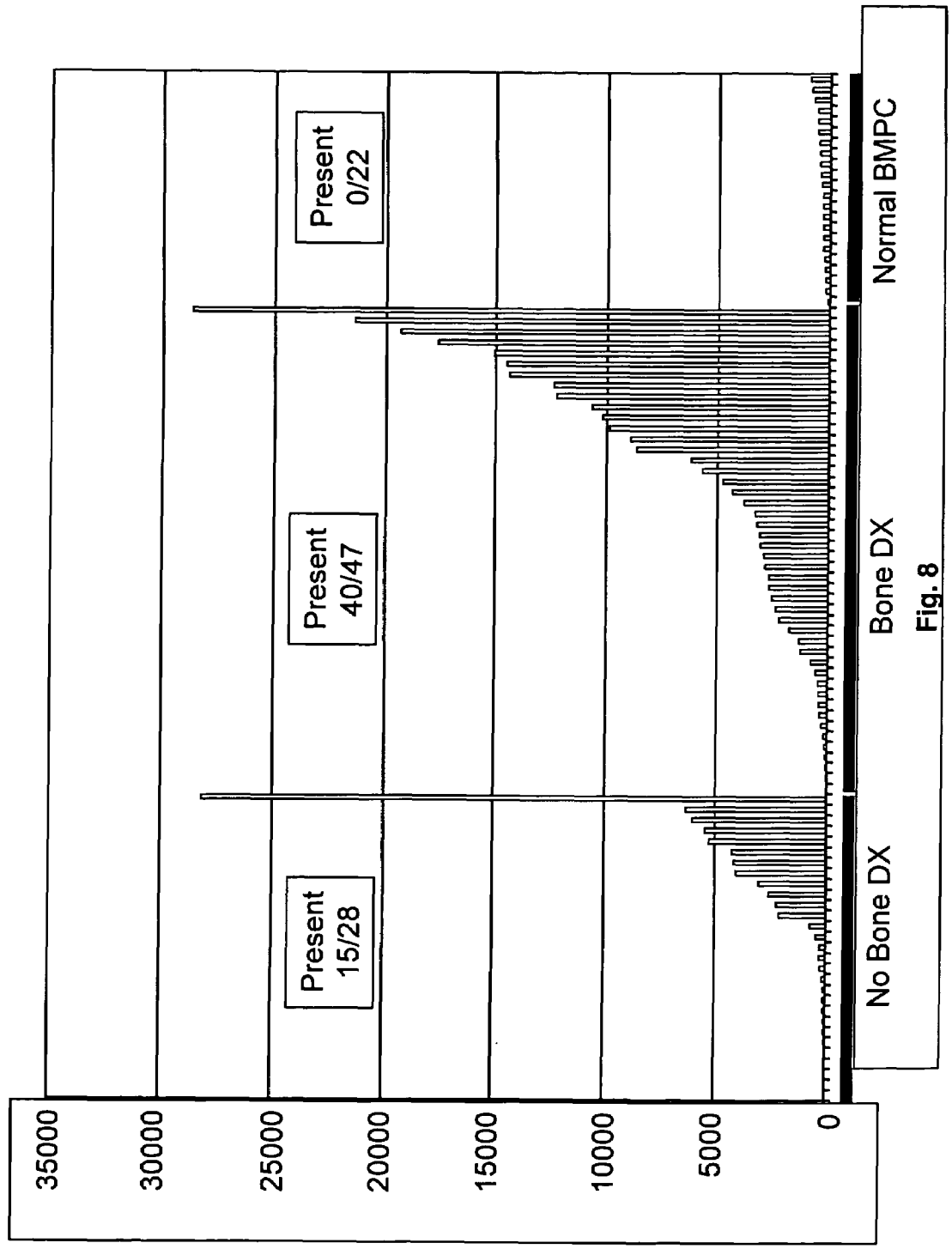
FIG. 8 shows the expression of WNT decoy receptor FRZB in multiple myeloma with lytic bone lesions.
Figure 9:
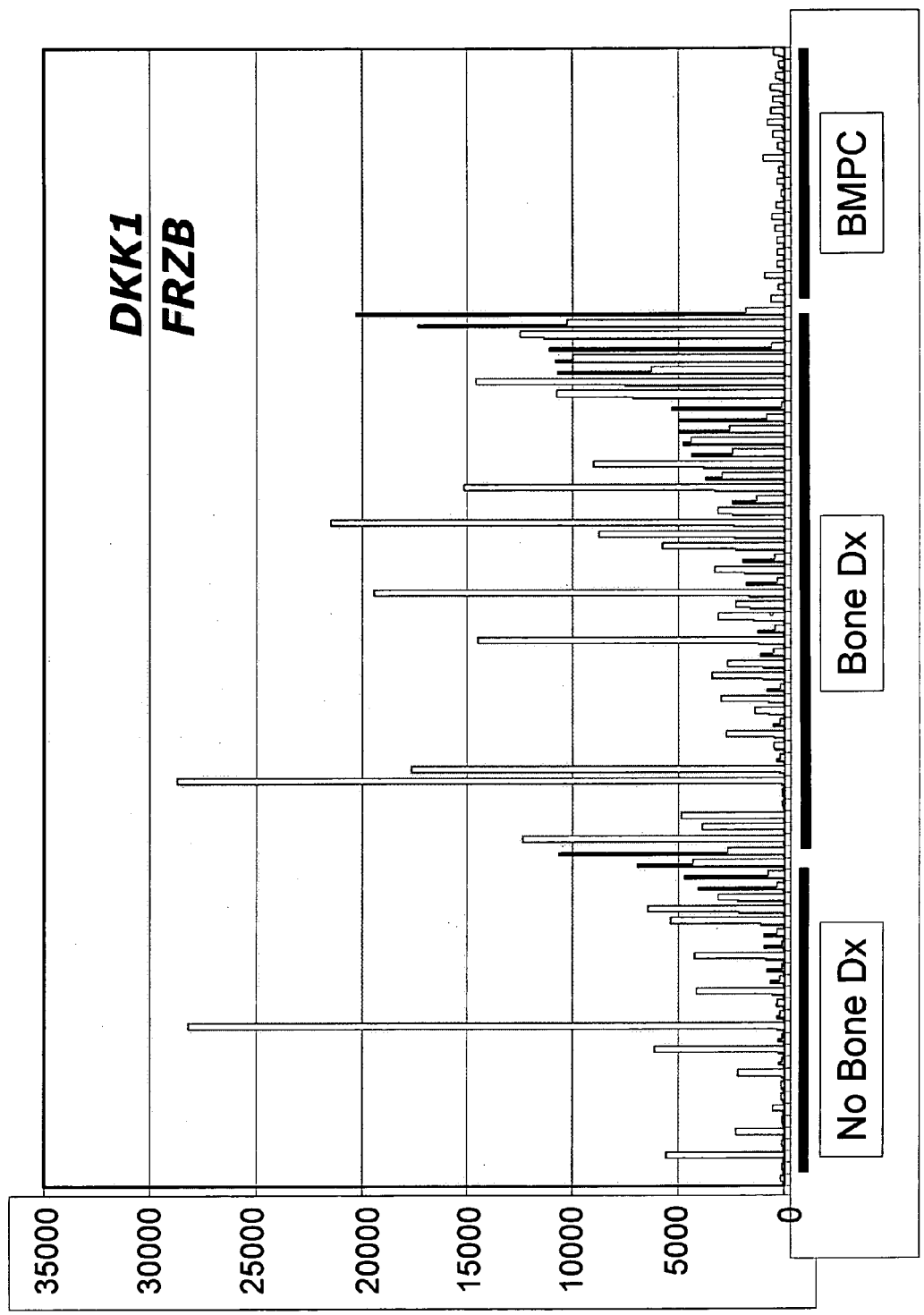
FIG. 9 shows the expression of DKK-1 and FRZB in multiple myeloma with lytic bone lesions. Black bar: DKK-1; gray bar: FRZB.
Figure 10:
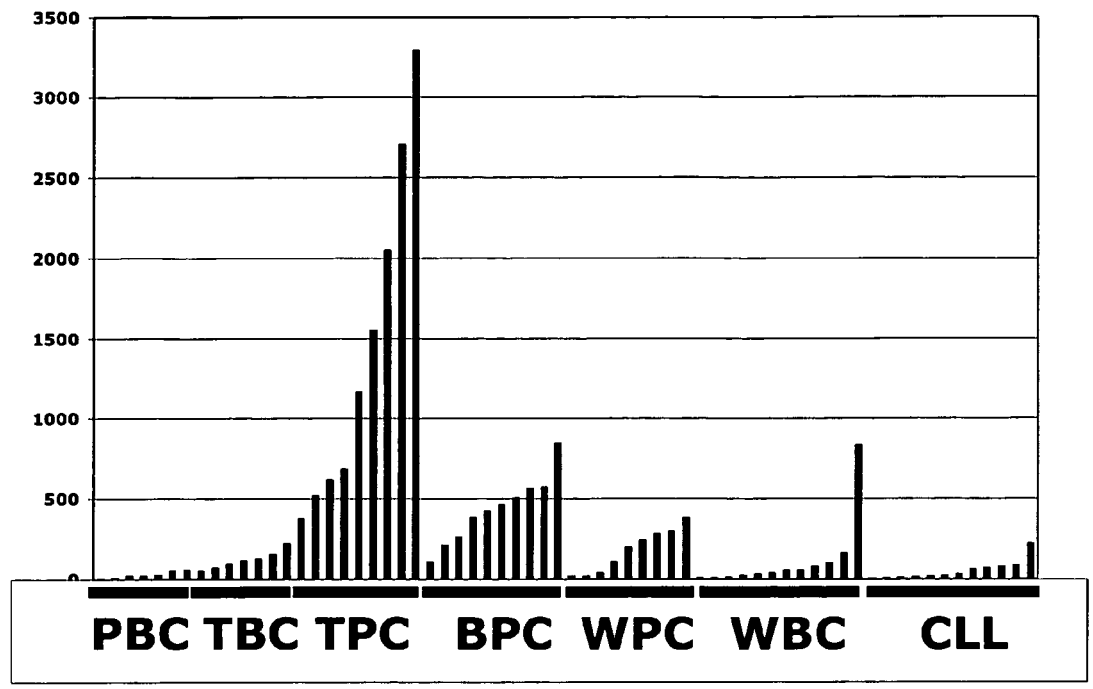
FIG. 10 shows FRZB was expressed in tonsil plasma cells. PBC, TBC, tonsil B cells; TPC, tonsil plasma cells; BPC, bone marrow plasma cells; WPC, WBC, CLL.
Figure 11:
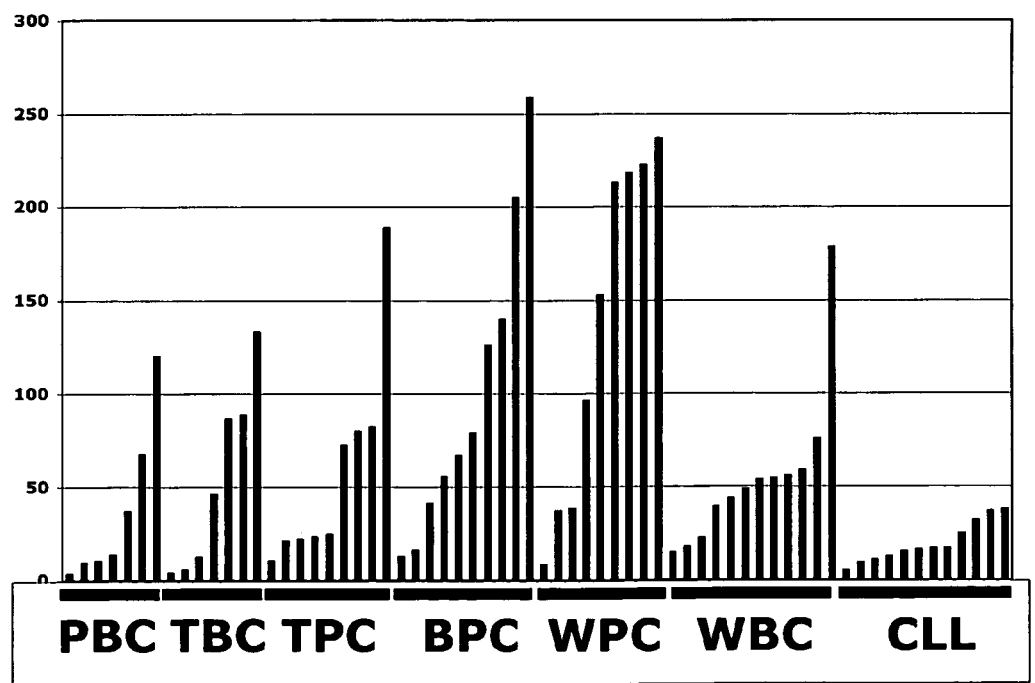
FIG. 11 shows DKK-1 was not expressed in normal B cells or plasma cells. PBC, TBC, tonsil B cells; TPC, tonsil plasma cells; BPC, bone marrow plasma cells; WPC, WBC, CLL.
Figure 12:
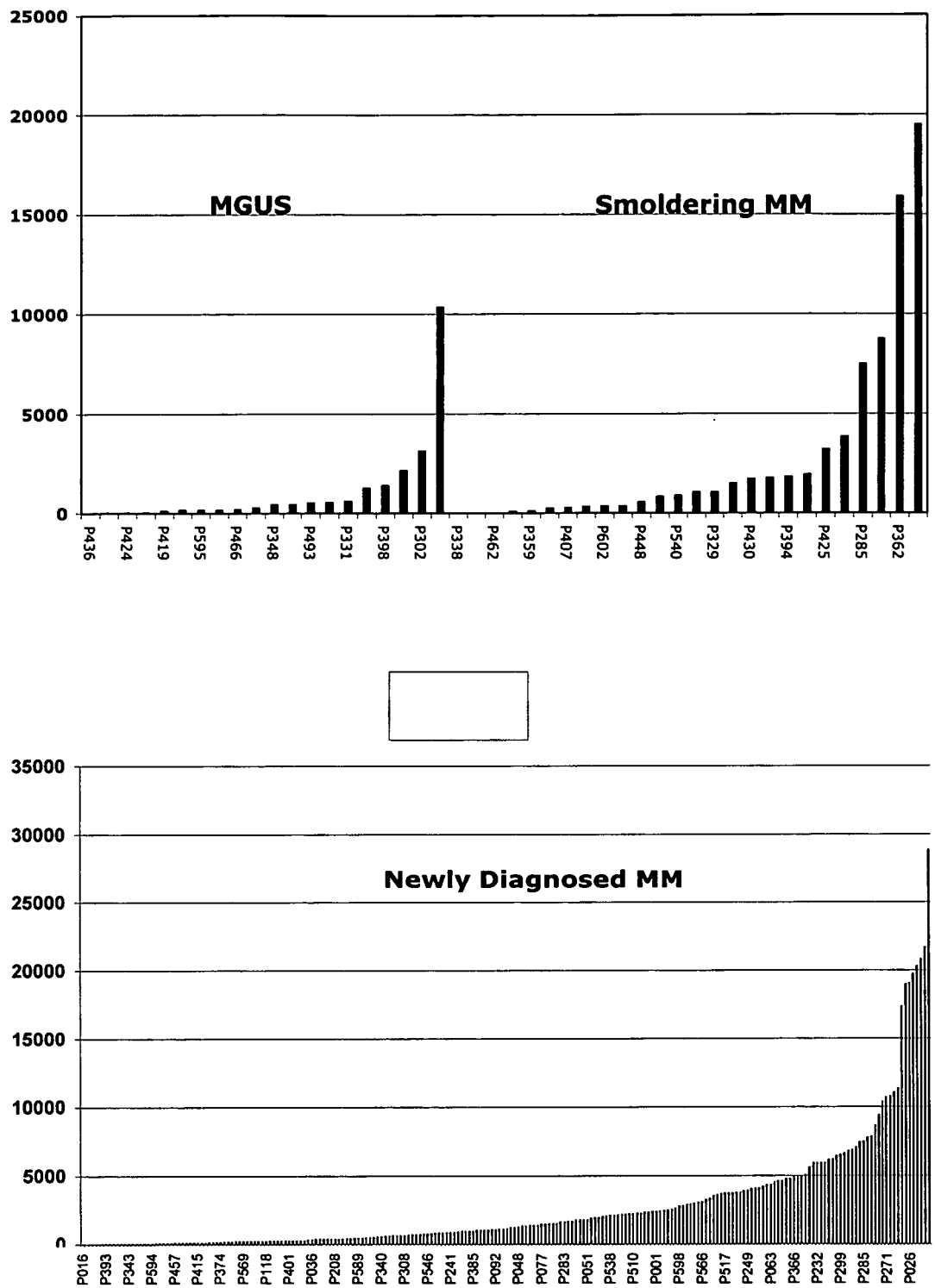
FIG. 12 shows DKK-1 expression in monoclonal gammopathy of undetermined significance (MGUS) was low relative to smoldering multiple myeloma (SMM) and newly diagnosed multiple myeloma (MM).
Figure 13:
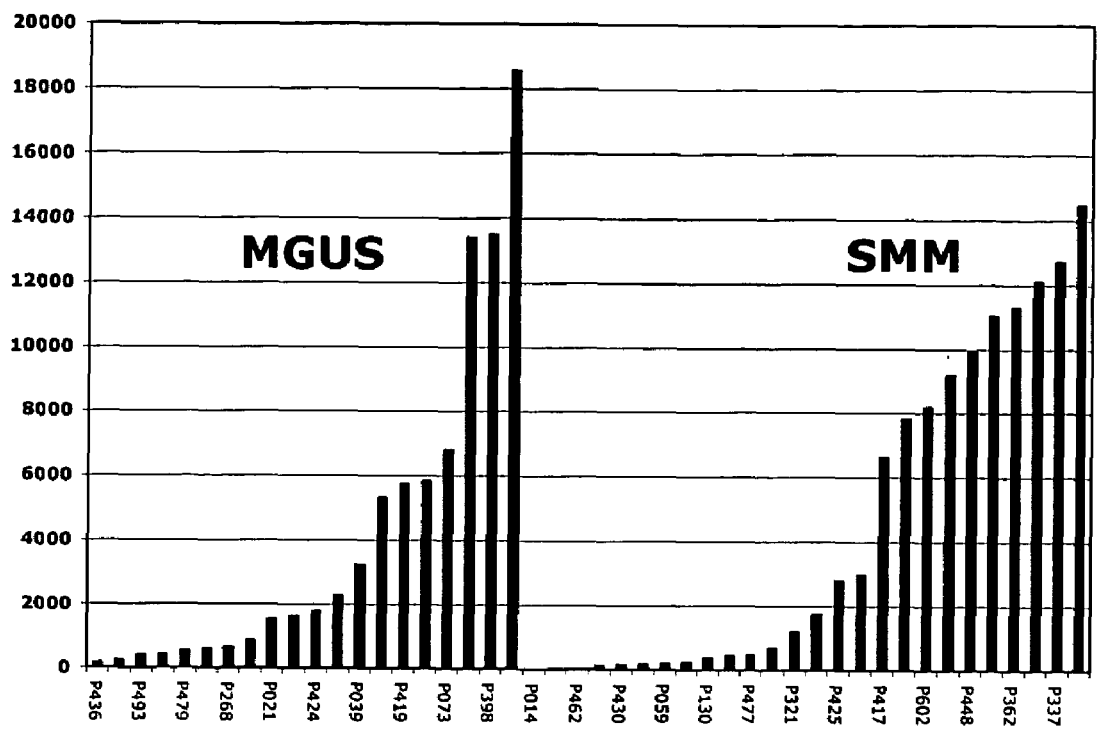
FIG. 13 shows FRZB was elevated in monoclonal gammopathy of undetermined significance (MGUS), and had higher expression in smoldering multiple myeloma (SMM) and newly diagnosed multiple myeloma (MM).
Figure 13:
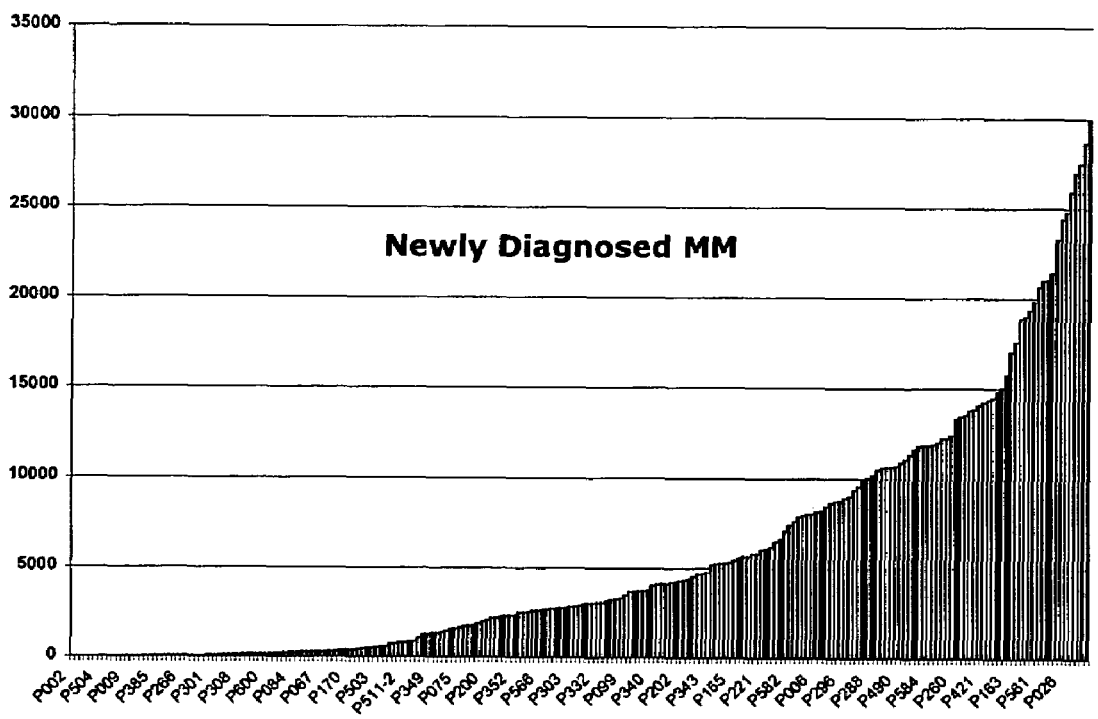
Figure 14:
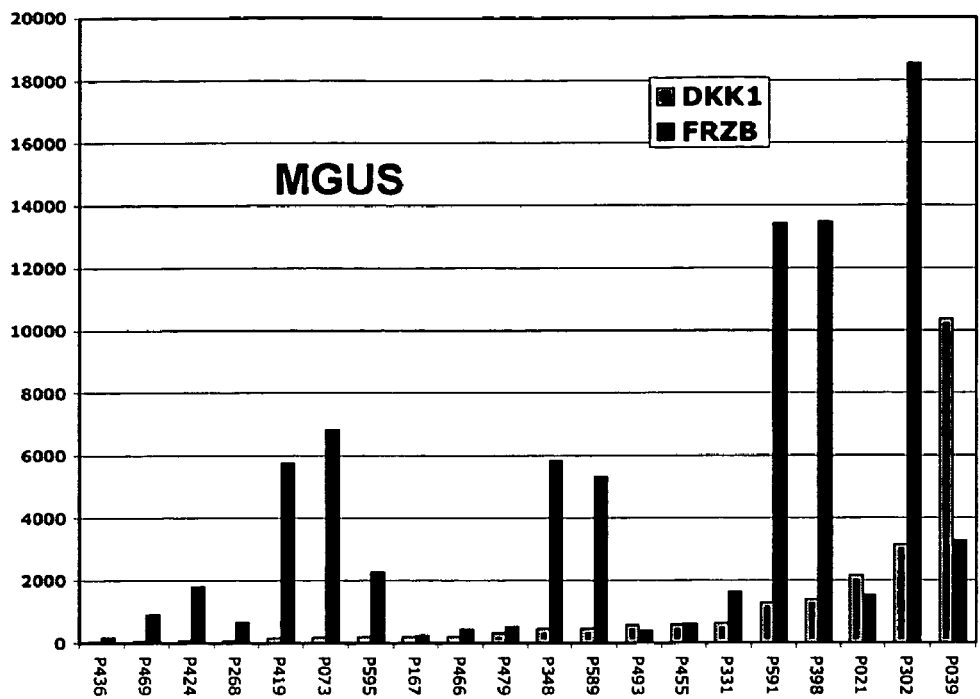
FIG. 14 shows the expression of DKK-1 and FRZB in monoclonal gammopathy of undetermined significance (MGUS) and smoldering multiple myeloma (SMM).
Figure 14:
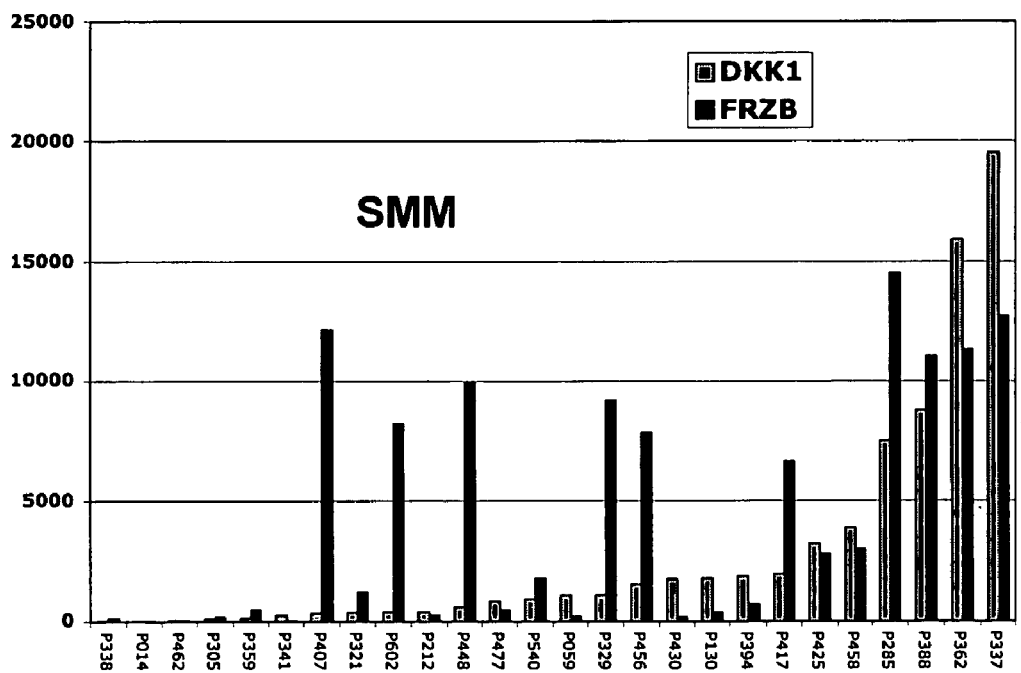

PTTG1 (securin) involved in chromosome segregation was identified by WRS as the most significant discriminating gene (P=$4 \times 10^{-6}$). It was called present in 11% of no lytic lesion group but present in 50% of the lytic lesion group (FIG. 4). Other notable genes in the WRS test included the TSC-22 homologue DSIPI which was expressed at lower levels in lytic lesion group (P=$3 \times 10^{-5}$). DSIPI is also down-regulated in 12 of 12 multiple myeloma plasma cells after ex-vivo co-culture with osteoclasts.

In addition, 4 so called "spike genes" were identified that were more frequently found in lytic lesion group versus no lytic lesion group (p<0.05): IL6, showing spikes in 0/28 no lytic lesion group and 7/47 lytic lesion group (p=0.032); Osteonidogen (NID2) showing spikes in 0/28 no lytic lesion group and 7/47 lytic lesion group (p=0.032); Regulator of G protein signaling (RGS13) showing spikes in 1/28 no lytic lesion group and 11/47 lytic lesion group (p=0.023); and pyromidinergic receptor P2Y (P2RY6) showing spikes in 1/28 no lytic lesion group and 1/47 lytic lesion group (p=0.023).

Thus, these data suggest that gene expression patterns may be linked to bone disease. In addition to being potentially useful as predictors of the emergence of lytic bone disease and conversion from monoclonal gammopathy of undetermined significance to overt multiple myeloma, they may also identify targets for potential intervention.

EXAMPLE 10

DDK1 and FRZB Tend to be Expressed at Higher Levels in Plasma Cells from Focal Lesions than from Random Marrow Given the relationship of DKK-1 and FRZB to lytic lesions, DKK-1 and FRZB expressions were compared in plasma cells derived from random bone marrow aspirates of the iliac crest with those derived by CT-guided fine needle aspiration of focal lesions of the spine. These results showed significantly higher levels of expression in plasma cells from focal lesions.

EXAMPLE 11

Figure 20:
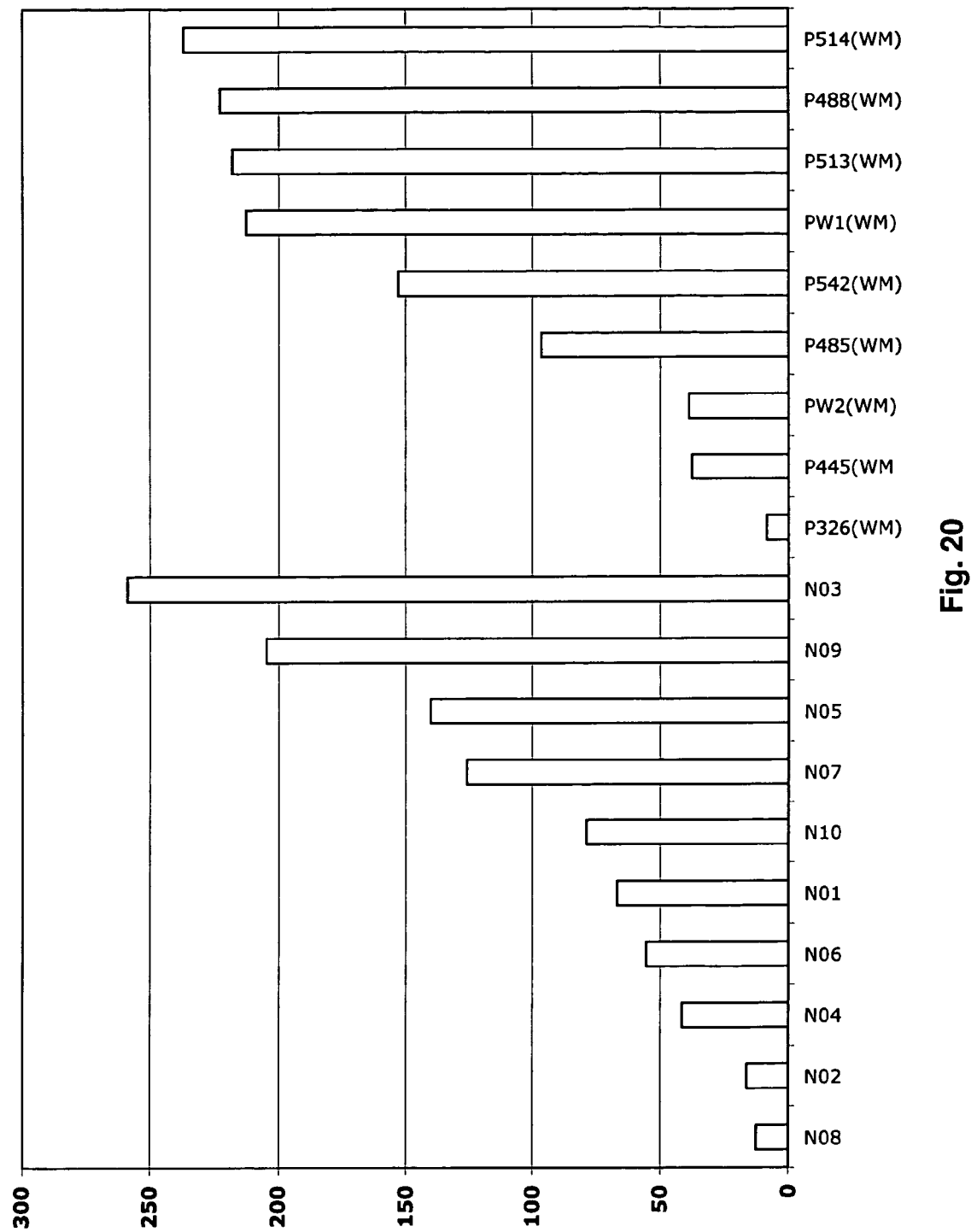
FIG. 20 shows DKK-1 was not expressed in plasma cells from Waldenstrom's macroglobulinemia.
Figure 21:
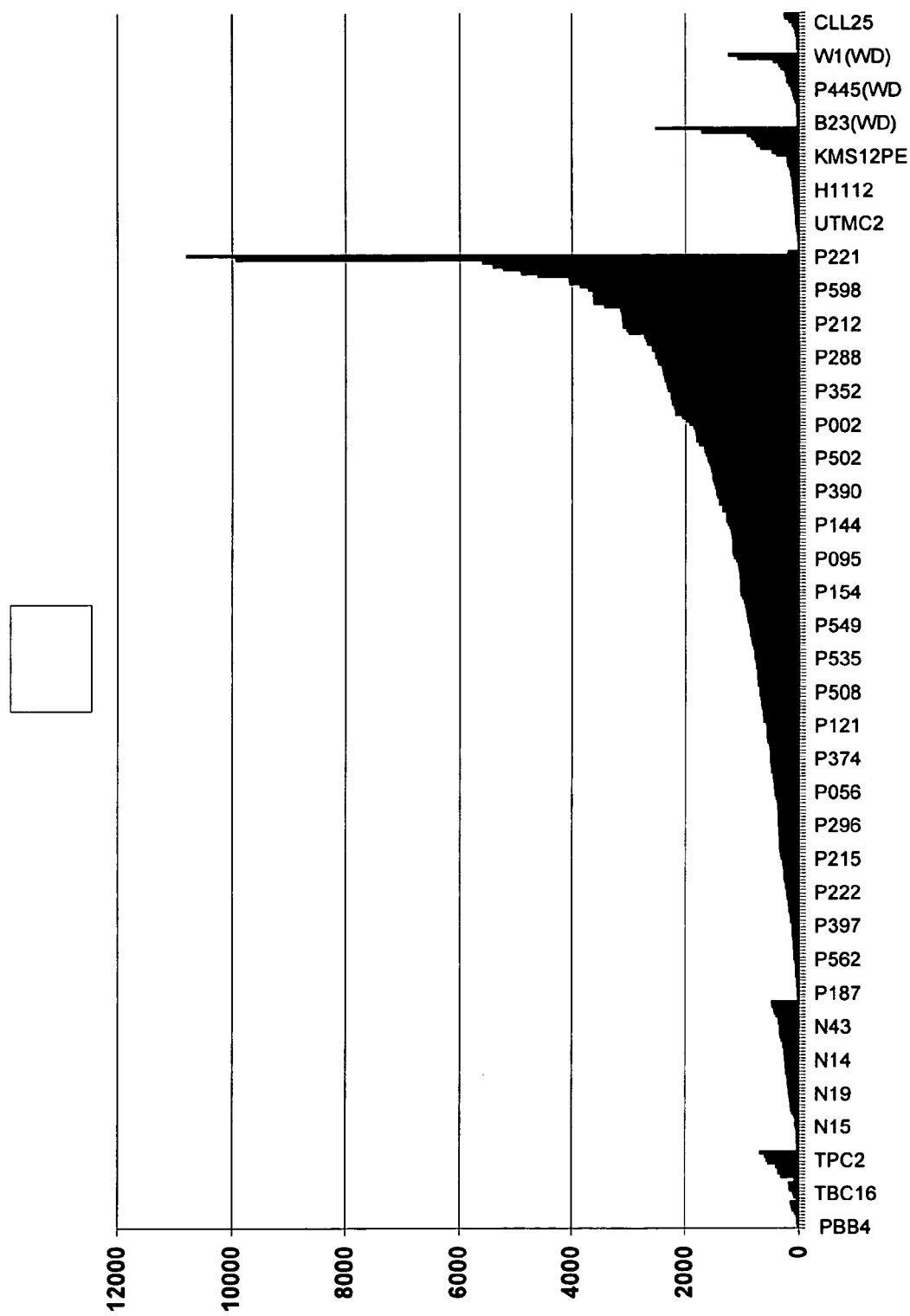
FIG. 21 shows WNT5A was elevated in newly diagnosed multiple myeloma.
Figure 22:
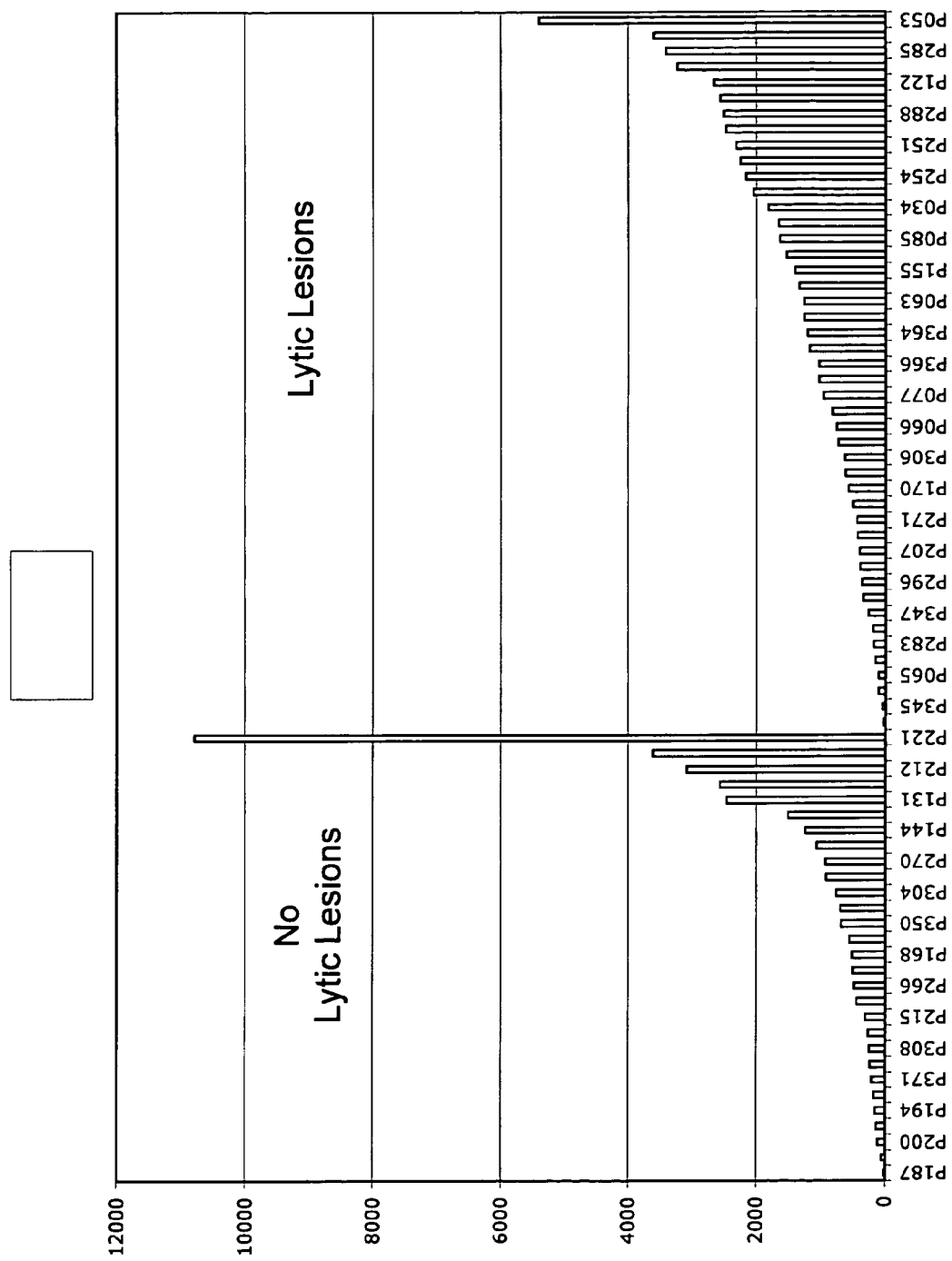
FIG. 22 shows WNT5A tends to be higher in multiple myeloma with lytic lesions.
Figure 23:
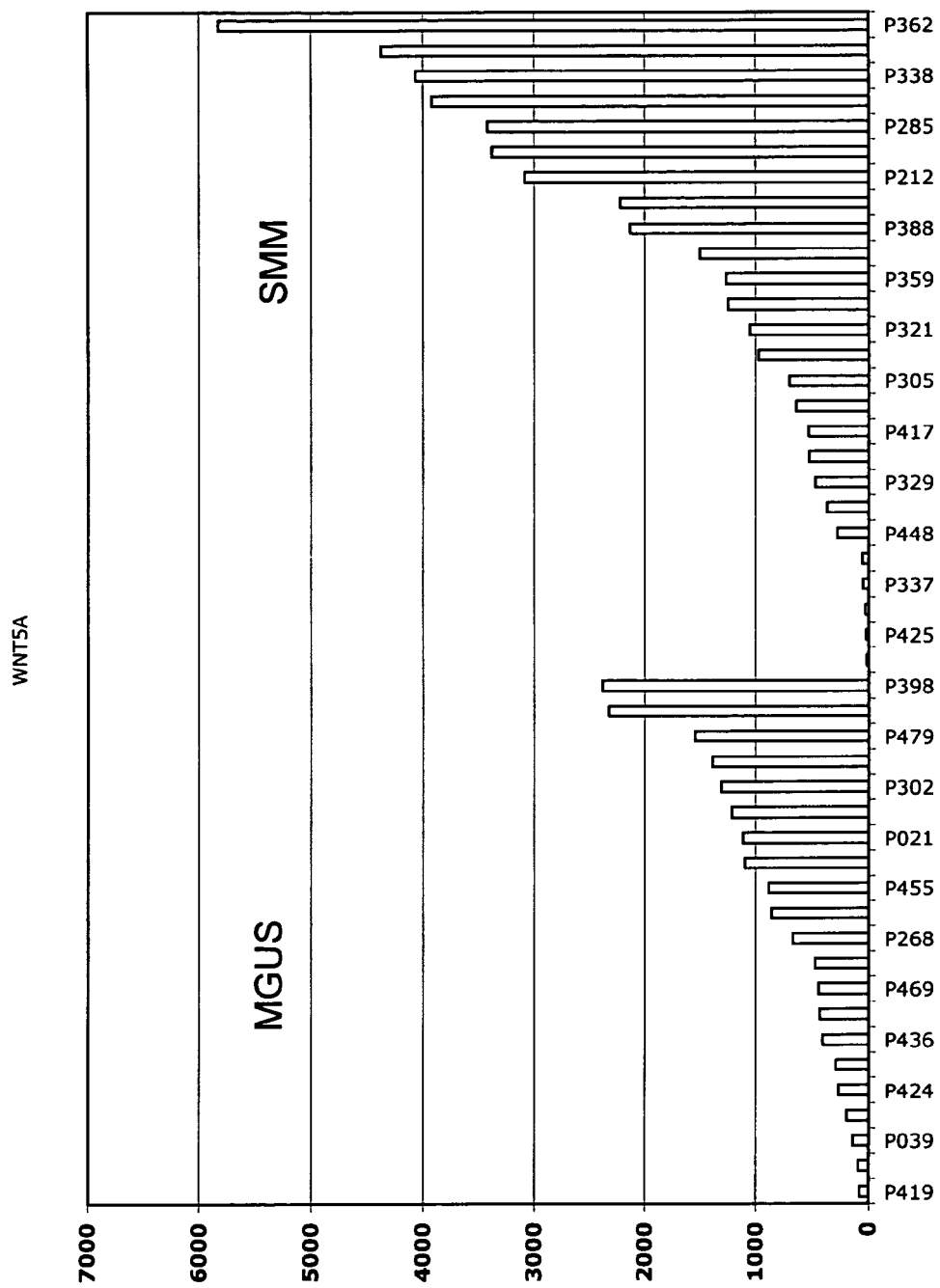
FIG. 23 shows WNT5A was also elevated in monoclonal gammopathy of undetermined significance (MGUS) and smoldering multiple myeloma (SMM).
Figure 24:
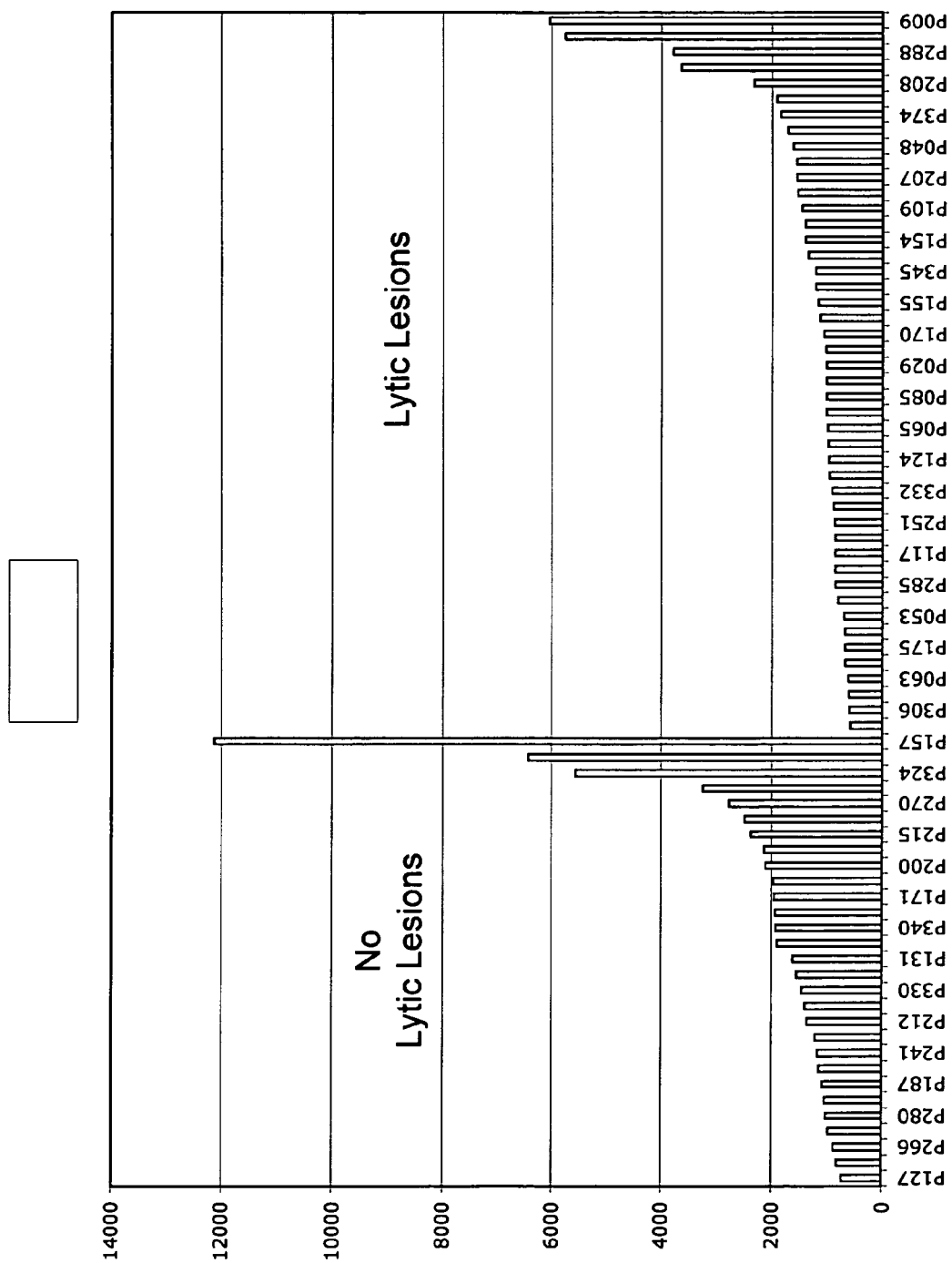
FIG. 24 shows WNT10B tends to be lower in multiple myeloma with lytic lesions.
Figure 25:
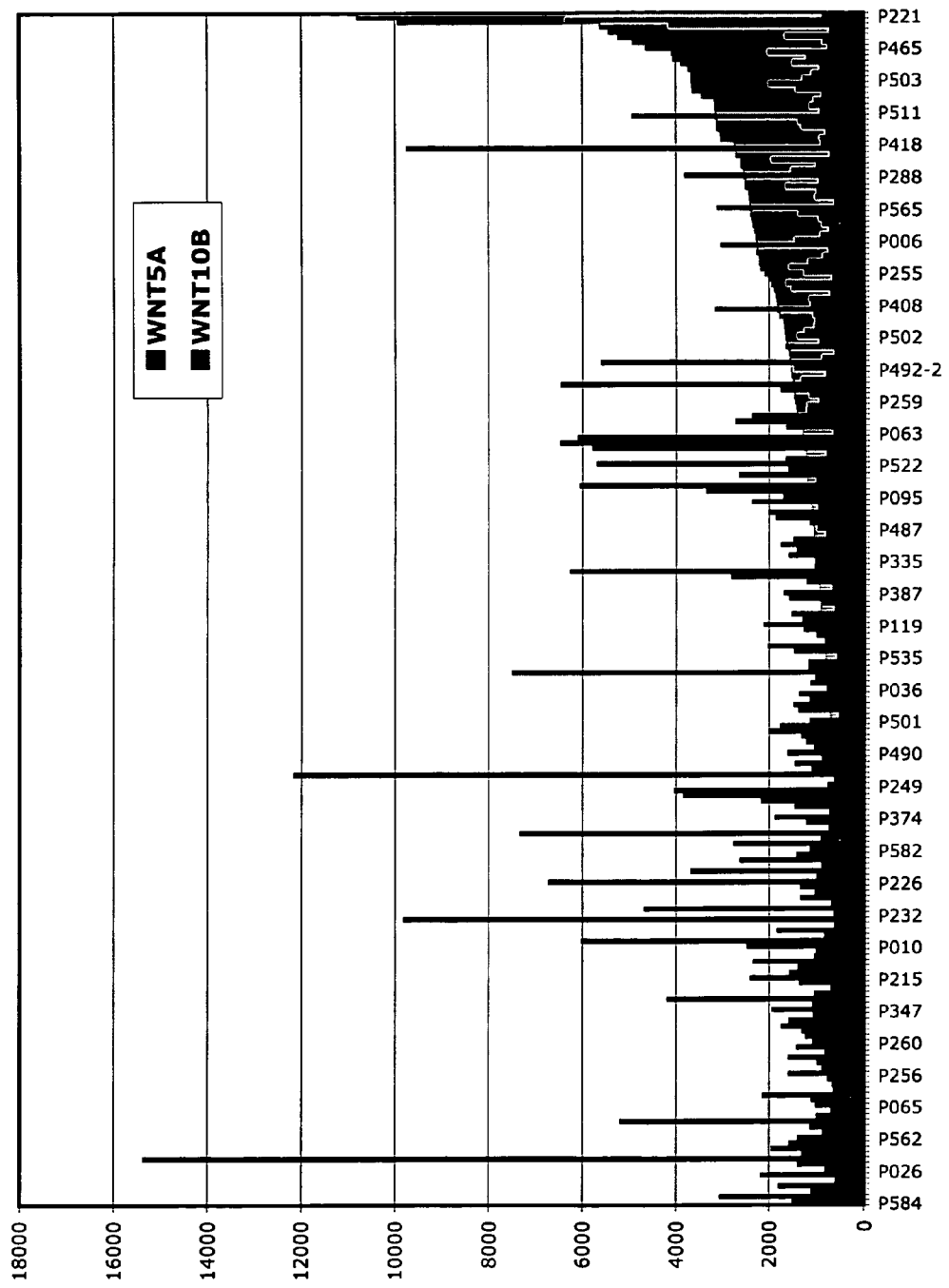
FIG. 25 shows WNT5A and WNT10B tend to be inversely correlated. Black bar: WNT10B; gray bar: WNT5A.
Figure 26:
FIG. 26 shows DKK-1 was present in an SK-LMS cell line.
Figure 26:
Figure 27:
FIG. 27 shows primary multiple myeloma synthesized DKK-1 protein.
Figure 27:
Figure 28:
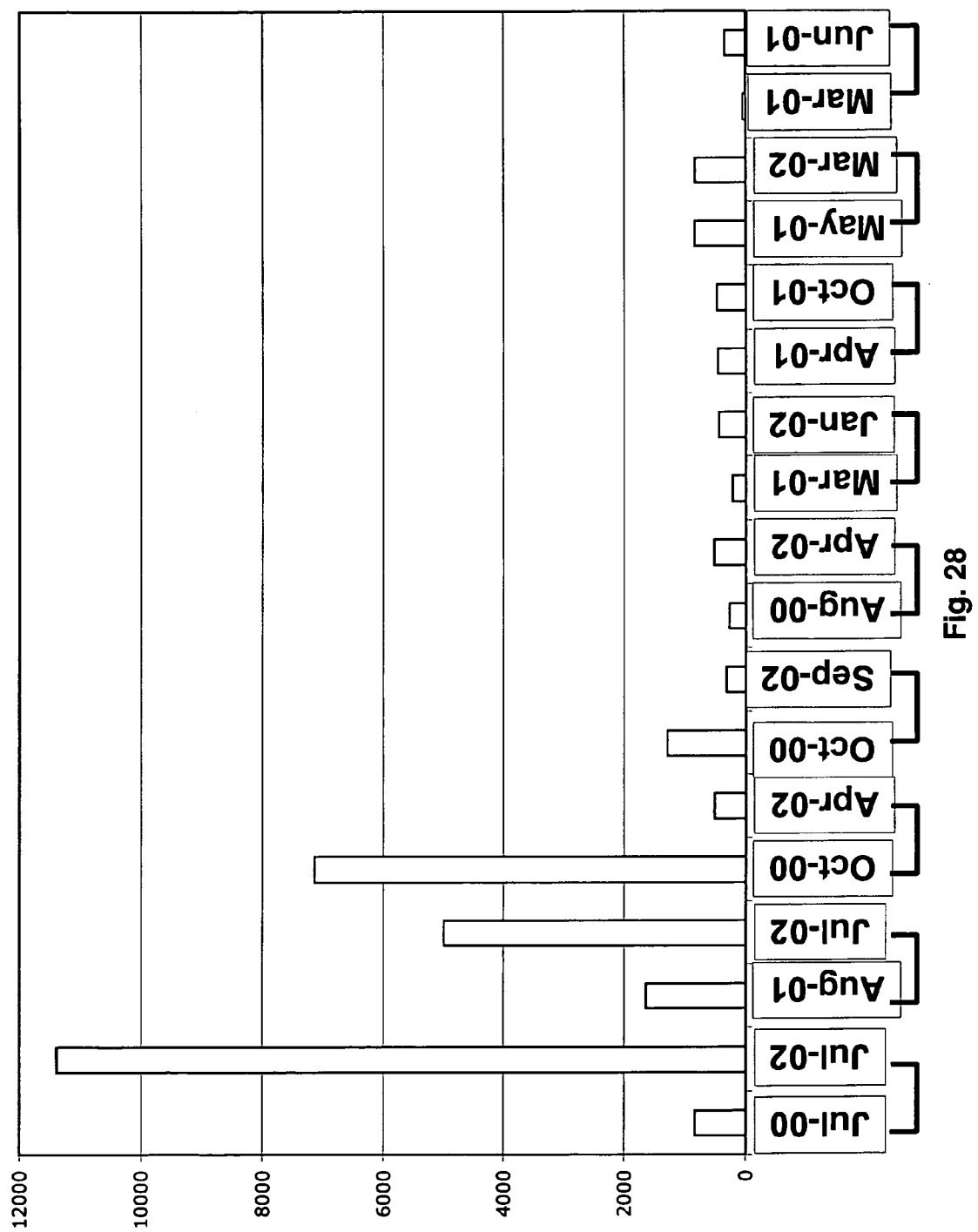
FIG. 28 shows low DKK-1 expression in relapsed and primary refractory multiple myeloma.

DKK-1 and FRZB are Not Expressed in Plasma Cells from Waldenstrom's Macroglobulinemia Waldenstrom's macroglobulinemia is a rare plasma cell dyscrasia characterized by a monoclonal IgM paraproteinemia and lymphoplasmacytic infiltration of bone marrow, lymph nodes and spleen. Its clinical presentation is quite variable as is the clinical course, yet unlike multiple myeloma, bone lesions are rare. Although global gene expression profiling of CD138-enriched bone marrow plasma cells from 10 cases of Waldenstrom's Macroglobulinemia reveled gross abnormalities (Zhan et al., 2002), these cells, like normal bone marrow plasma cells, lack expression of FRZB and DKK (FIG. 20).

EXAMPLE 12

FRZB and Endothelin Receptor B are Correlated with DKK-1

Figure 31:
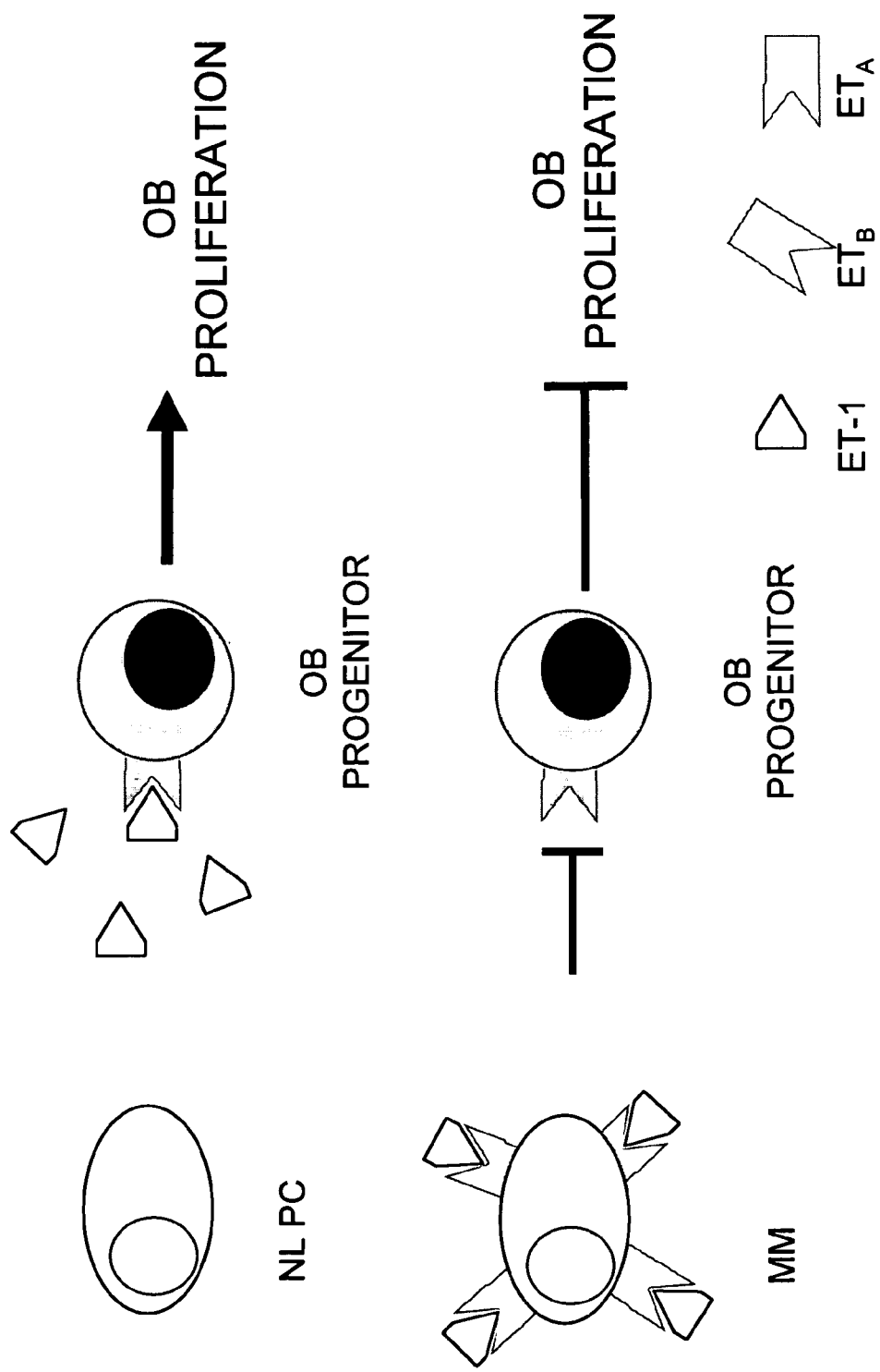
FIG. 31 shows the involvement of endothelin receptor B in bone formation.

Endothelin 1 is a 21 amino acids vasoconstrictor. Two receptors for endothelin, receptors A and B, have been identified. Breast and prostate cancer cells can produce endothelin 1, and increased concentrations of endothelin 1 and endothelin receptor A have been found in advanced prostate cancer with bone metastases. Breast cancer cells that produced endothelin 1 caused osteoblastic metastases in female mice. Conditioned media and exogenous endothelin 1 stimulated osteoblasts proliferation and new bone formation in mouse calvariae cultures (FIG. 31). These results suggest that endothelin is linked to bone formation.

Figure 29:
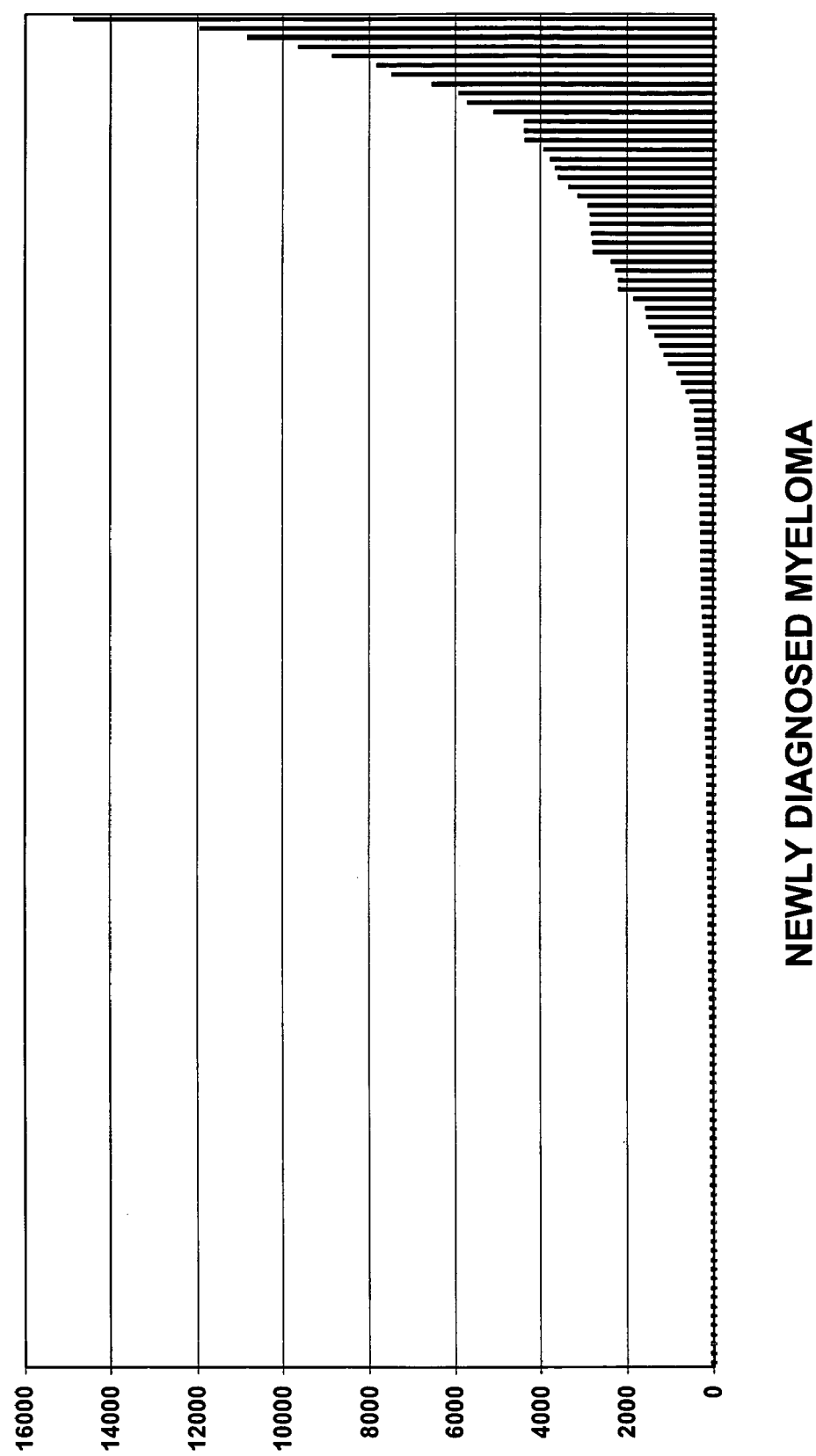
FIG. 29 shows endothelin receptor B was a "spike" gene in one third of newly diagnosed multiple myeloma.
Figure 30:
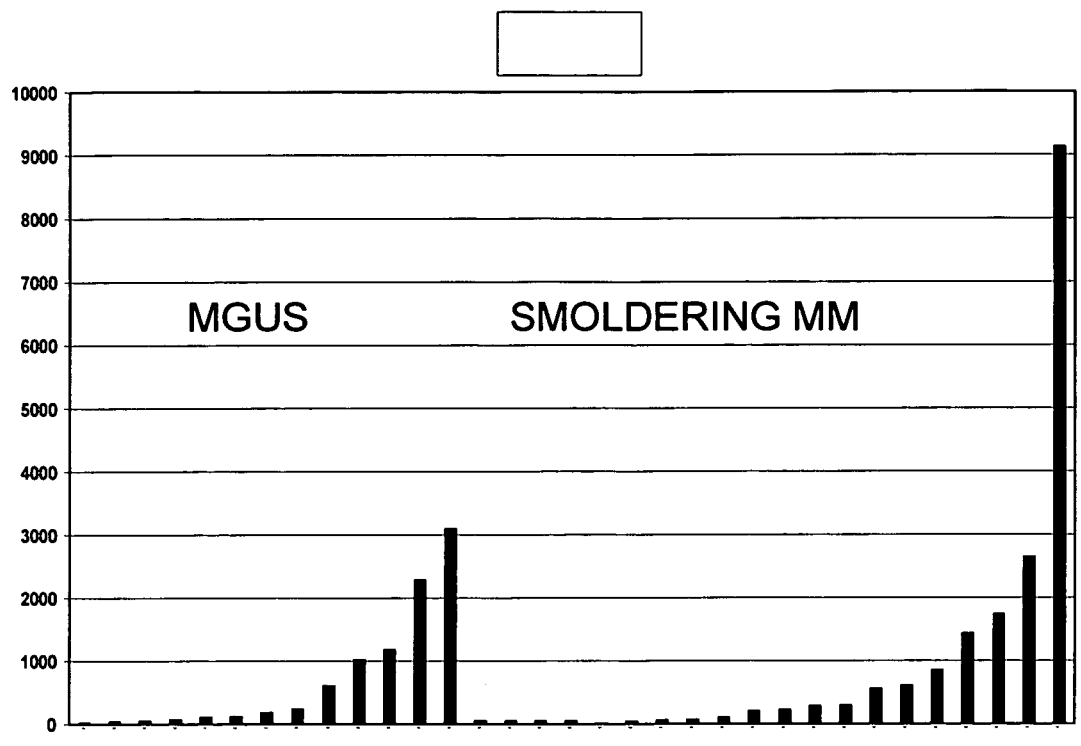
FIG. 30 shows the expression of endothelin receptor B in monoclonal gammopathy of undetermined significance (MGUS) and smoldering multiple myeloma. Normal plasma cells do not express endothelin receptor B.
Figure 30:
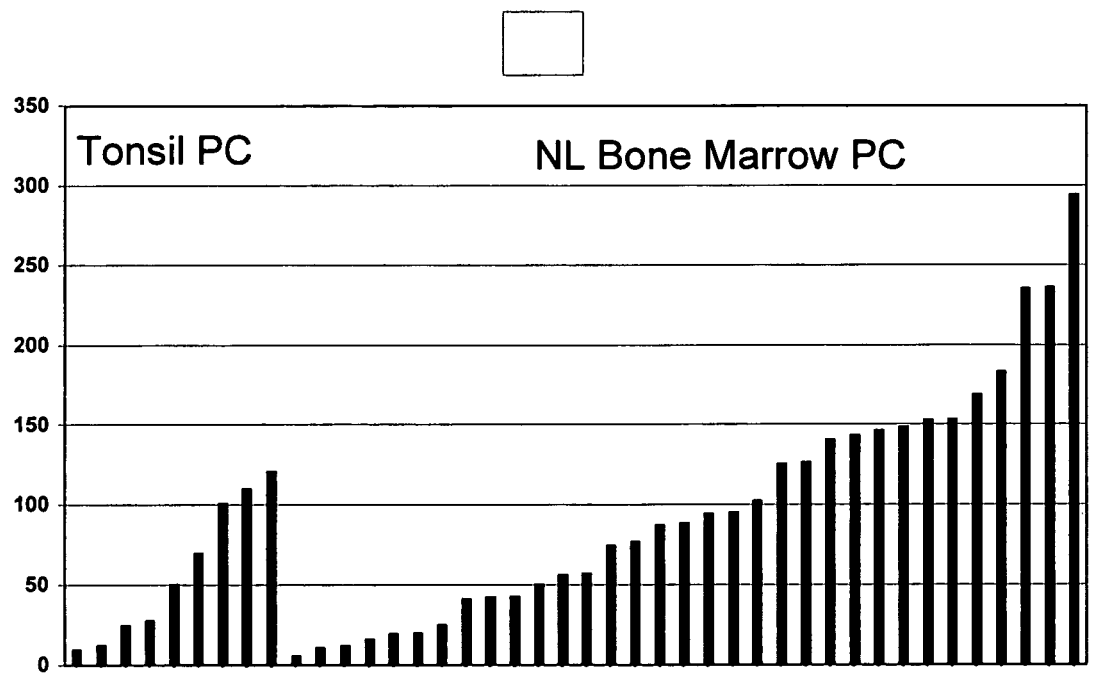

Table 3 shows that the expression of endothelin receptor B (ENDRB) was correlated with that of DKK-1. Endothelin receptor B was a 'spike' gene in one third of newly diagnosed multiple myeloma (FIG. 29). Endothelin receptor B was also expressed in subsets of monoclonal gammopathy of undetermined significance (MGUS) and smoldering multiple myeloma but not in normal plasma cells (FIG. 30).

TABLE 3

Correlation Between Endothelin Receptor B (EDNRB) and DKK-1

| Gene Symbol | Asymp. Significance (two-tailed) |
|---|---|
| DKK-1 | $6.35 \times 10^{-14}$ |
| FRZB | $6.59 \times 10^{-8}$ |
| EDNRB | 0.00014 |
| DKFZP564G202 | $4.83 \times 10^{-11}$ |

TABLE 3-continued

Correlation Between Endothelin
Receptor B (EDNRB) and DKK-1

| Gene Symbol | Asymp. Significance (two-tailed) |
|---|---|
| IFI27 | $1.43 \times 10^{-6}$ |
| SLC13A3 | 0.00011 |
| CCND1 | 0.00010 |
| SYN47 | $4.27 \times 10^{-10}$ |
| PCDH9 | 0.00029 |

EXAMPLE 13

In Vivo Drug Treatment Upregulates DKK-1

Figure 15:
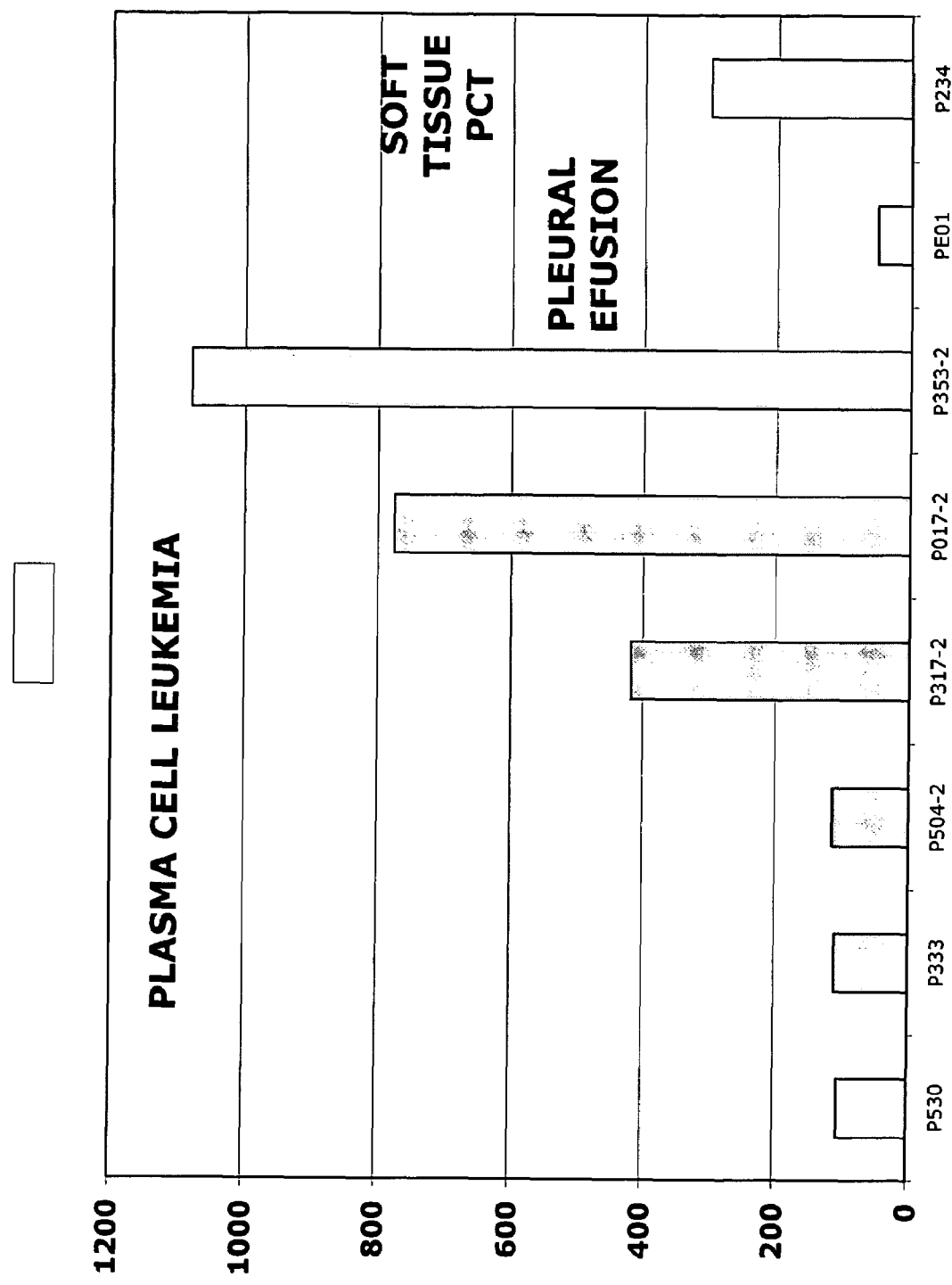
FIG. 15 shows low expression of DKK-1 in extramedullary disease.
Figure 16:
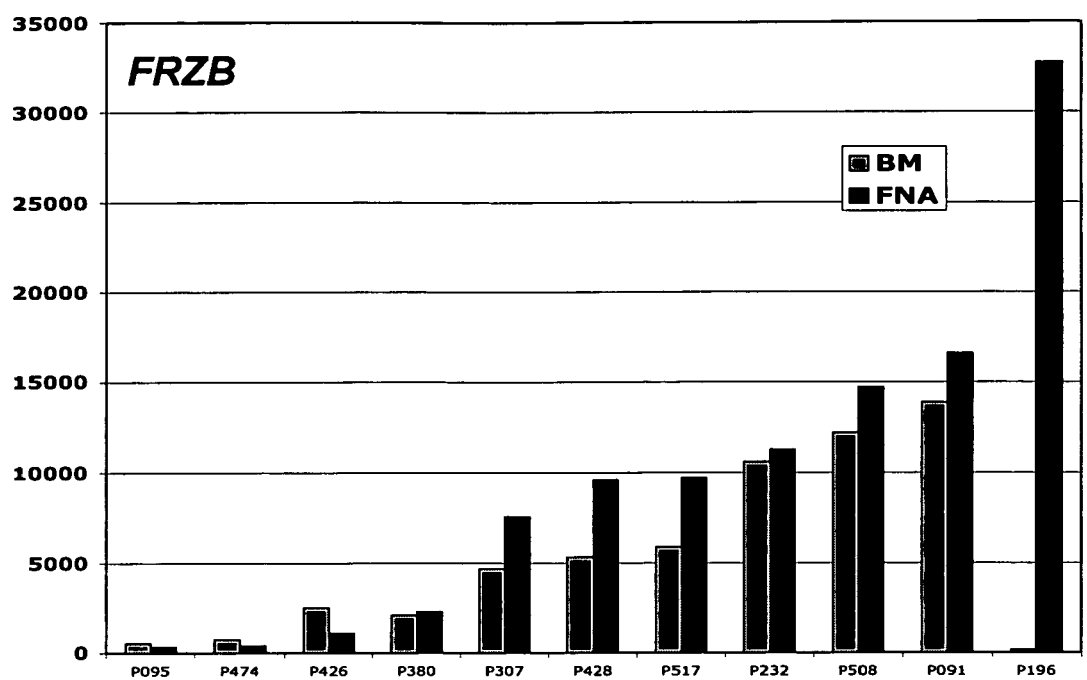
FIG. 16 shows the expression of DKK-1 and FRZB tend to be higher in plasma cells from medullary PCT than those from iliac crest. PCT, FNA.
Figure 16:
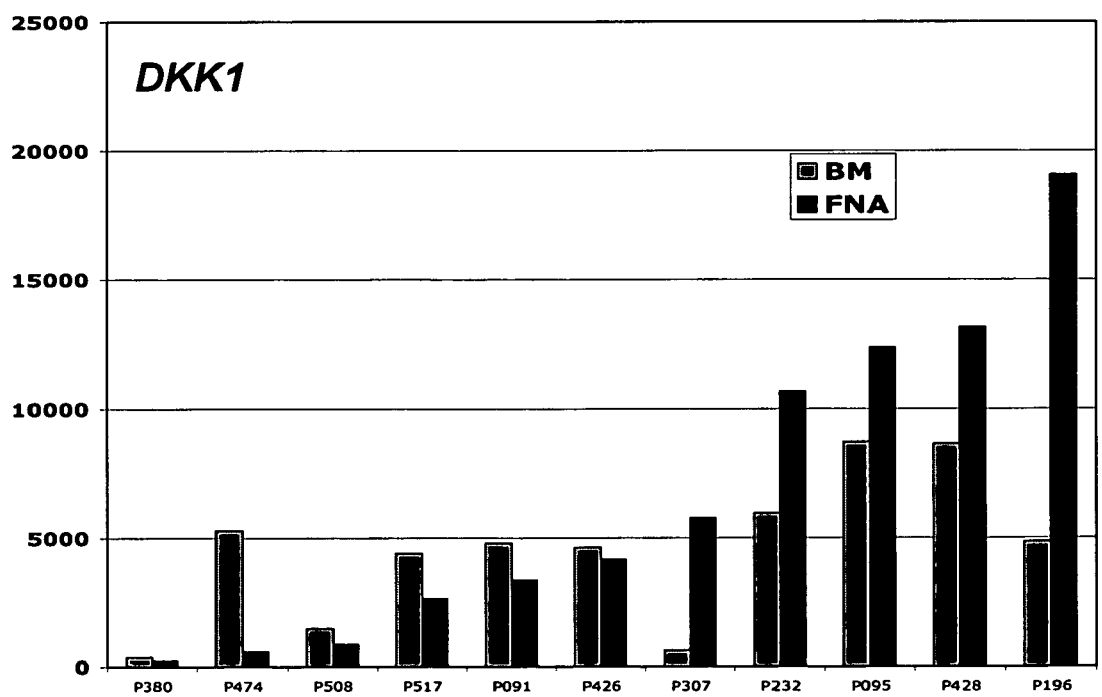
Figure 17:
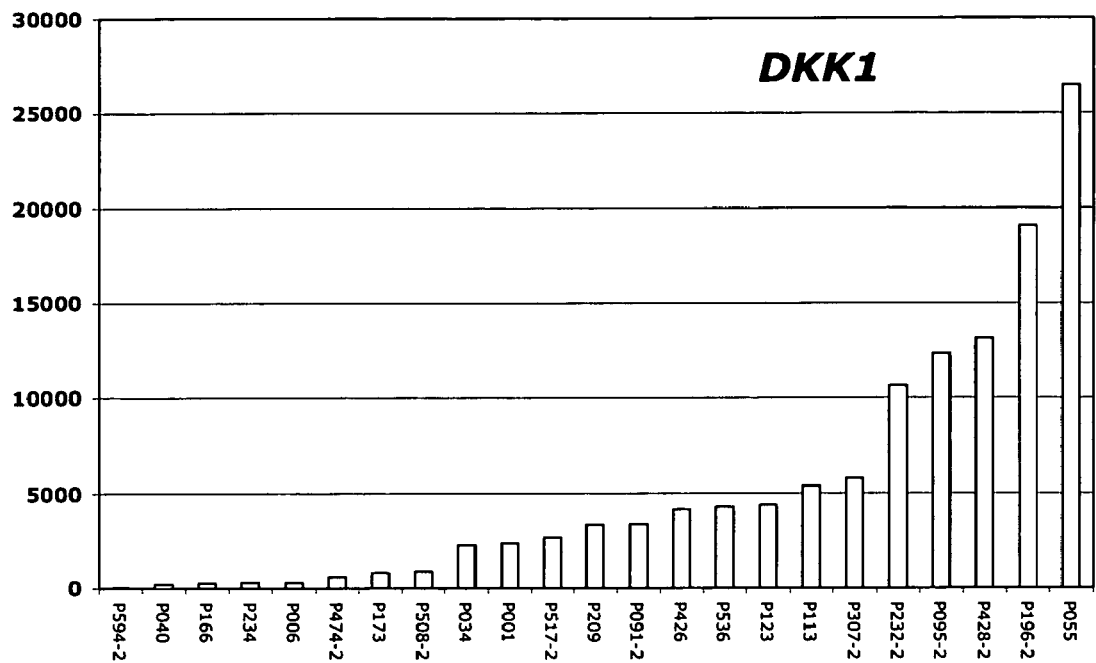
FIG. 17 shows the expression of DKK-1 and FRZB in fine needle aspirates of medullary PCT.
Figure 17:
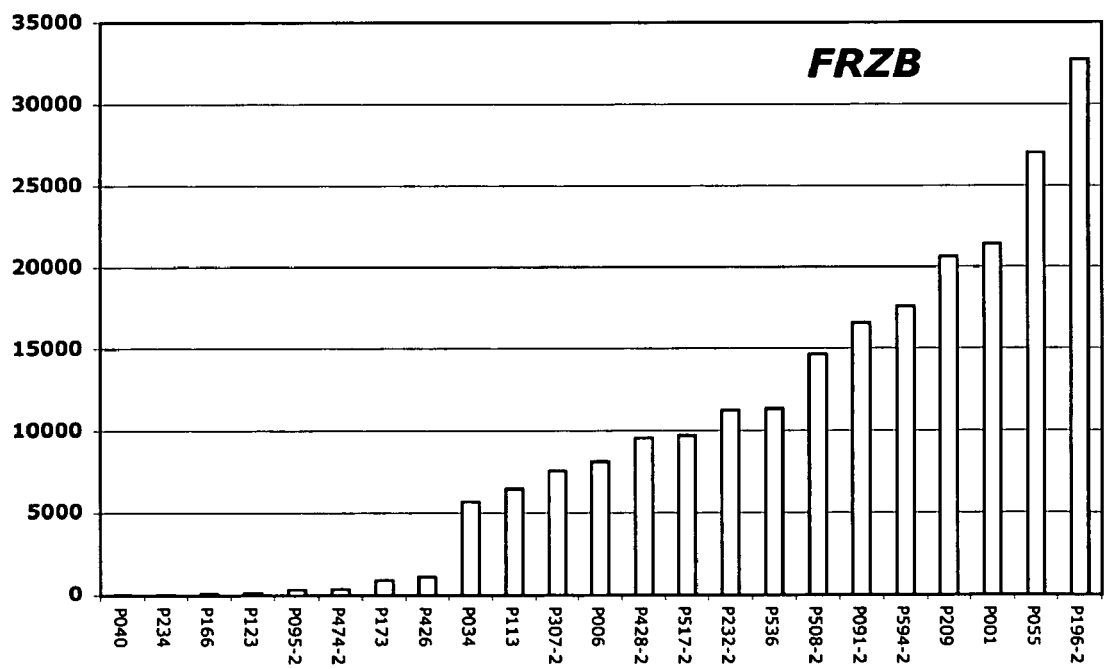
Figure 18:
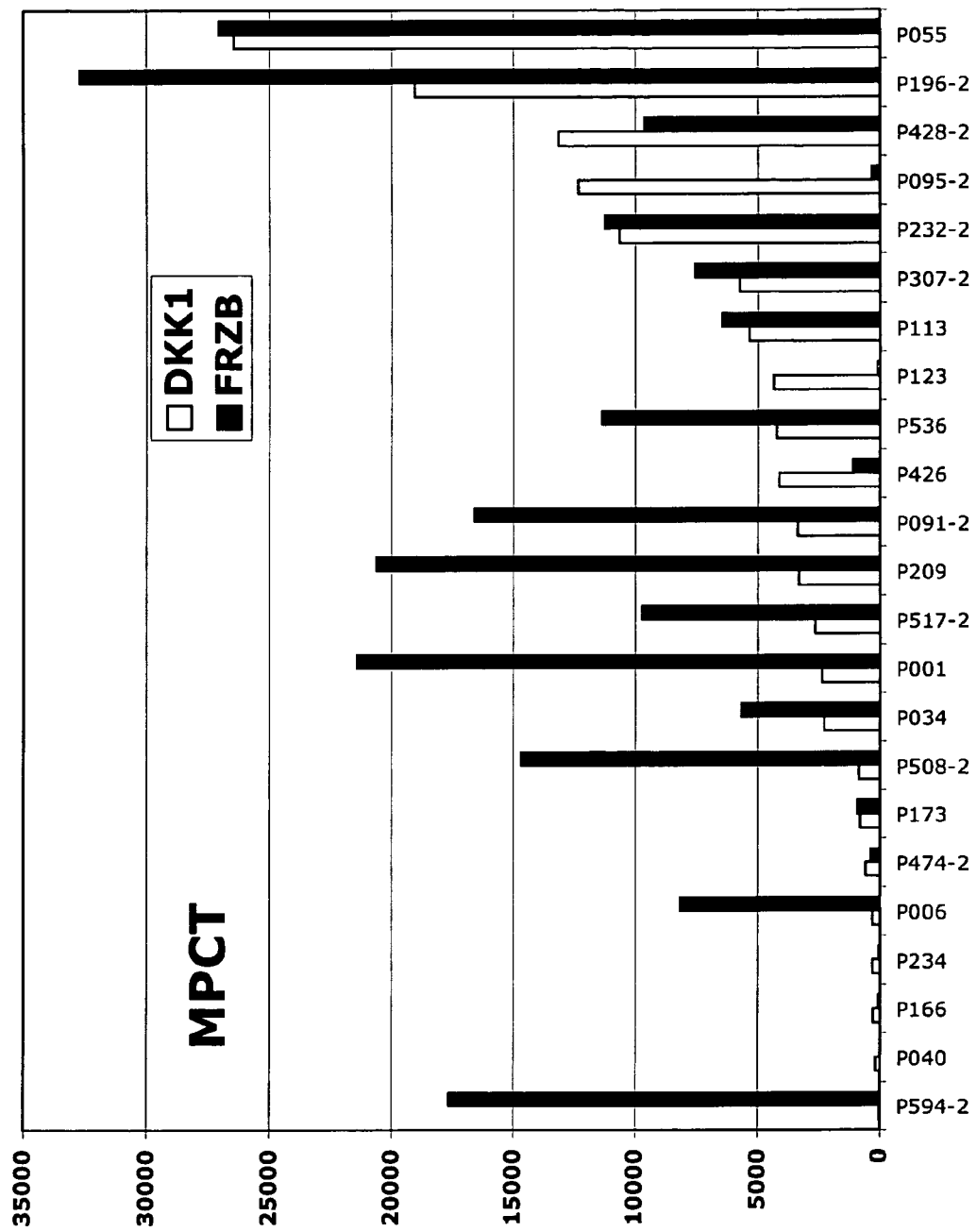
FIG. 18 shows high expression of DKK-1 and FRZB in medullary plasmacytoma.
Figure 19:
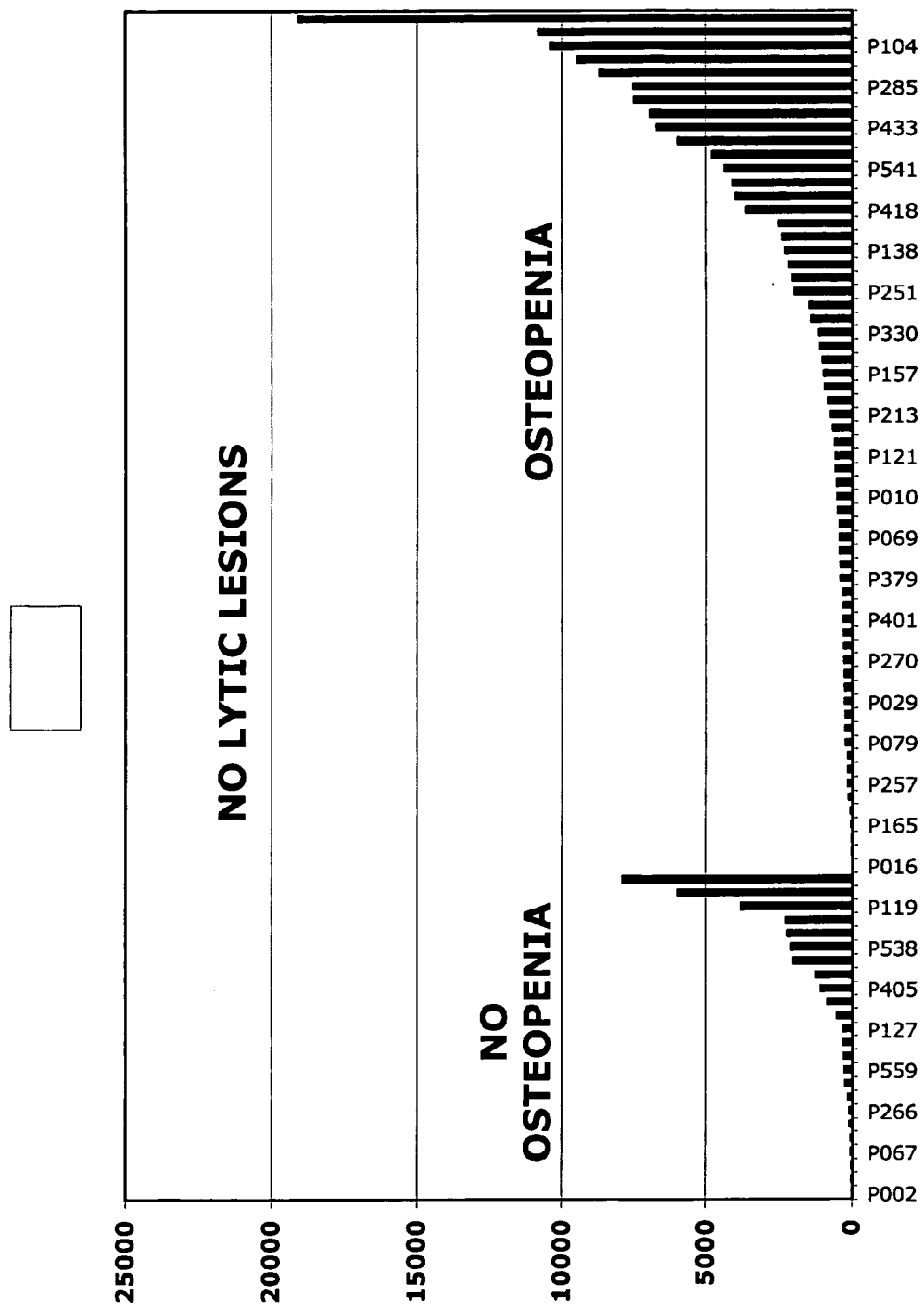
FIG. 19 shows higher expression of DKK-1 in multiple myeloma with osteopenia.
Figure 32:
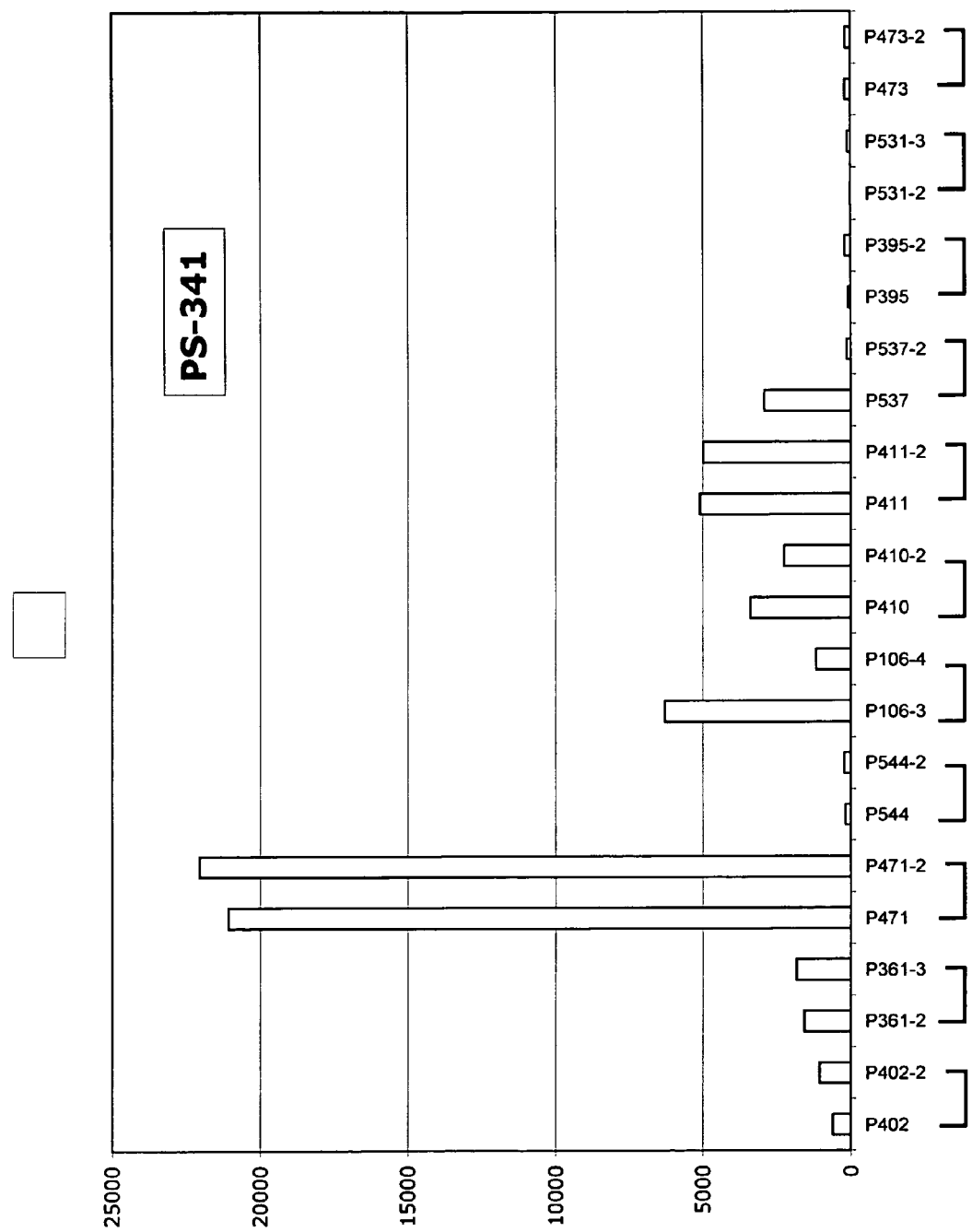
FIG. 32 shows DKK-1 expression after treatment with PS-341.
Figure 33:
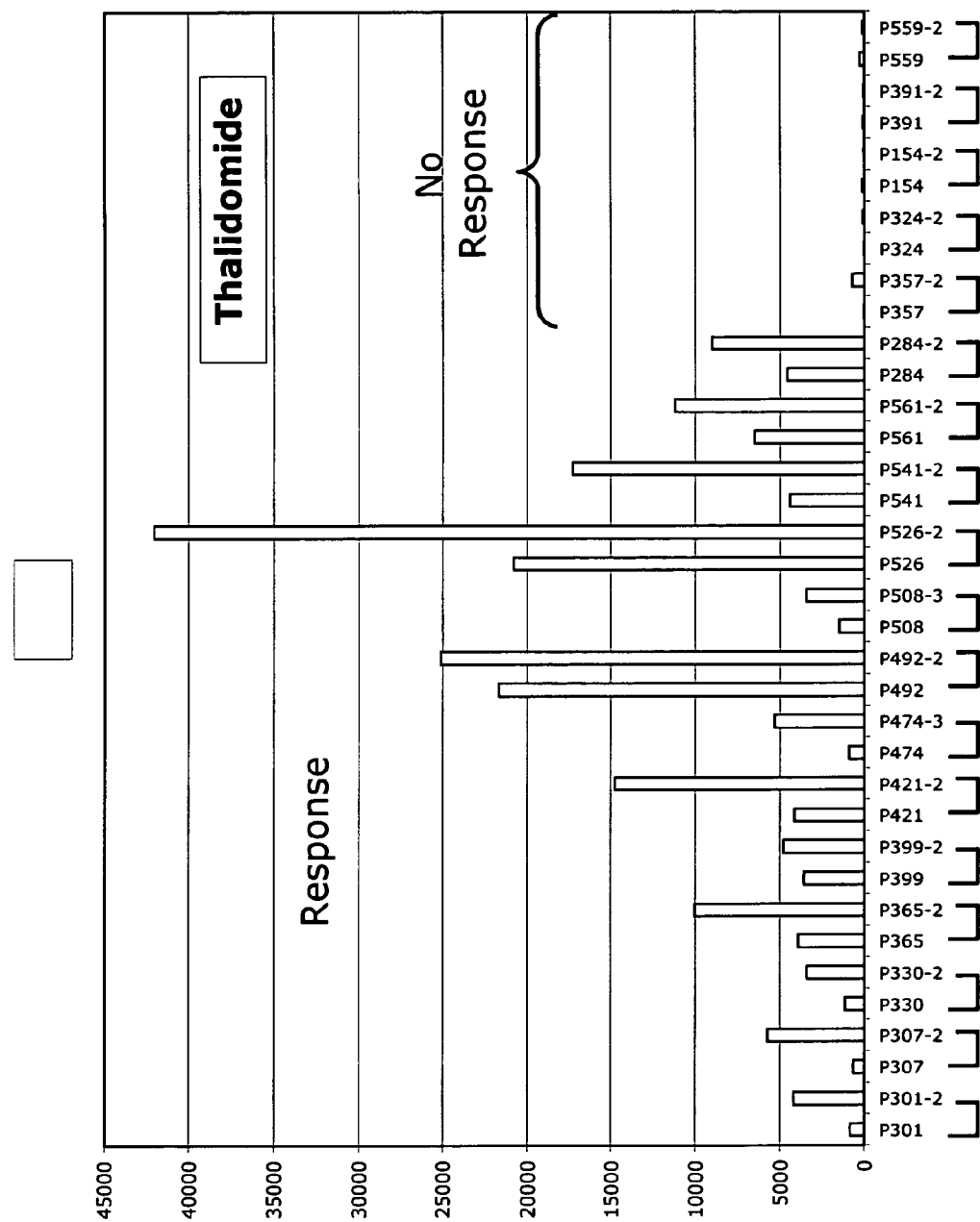
FIG. 33 shows DKK-1 expression after treatment with thalomid in newly diagnosed multiple myeloma.
Figure 34:
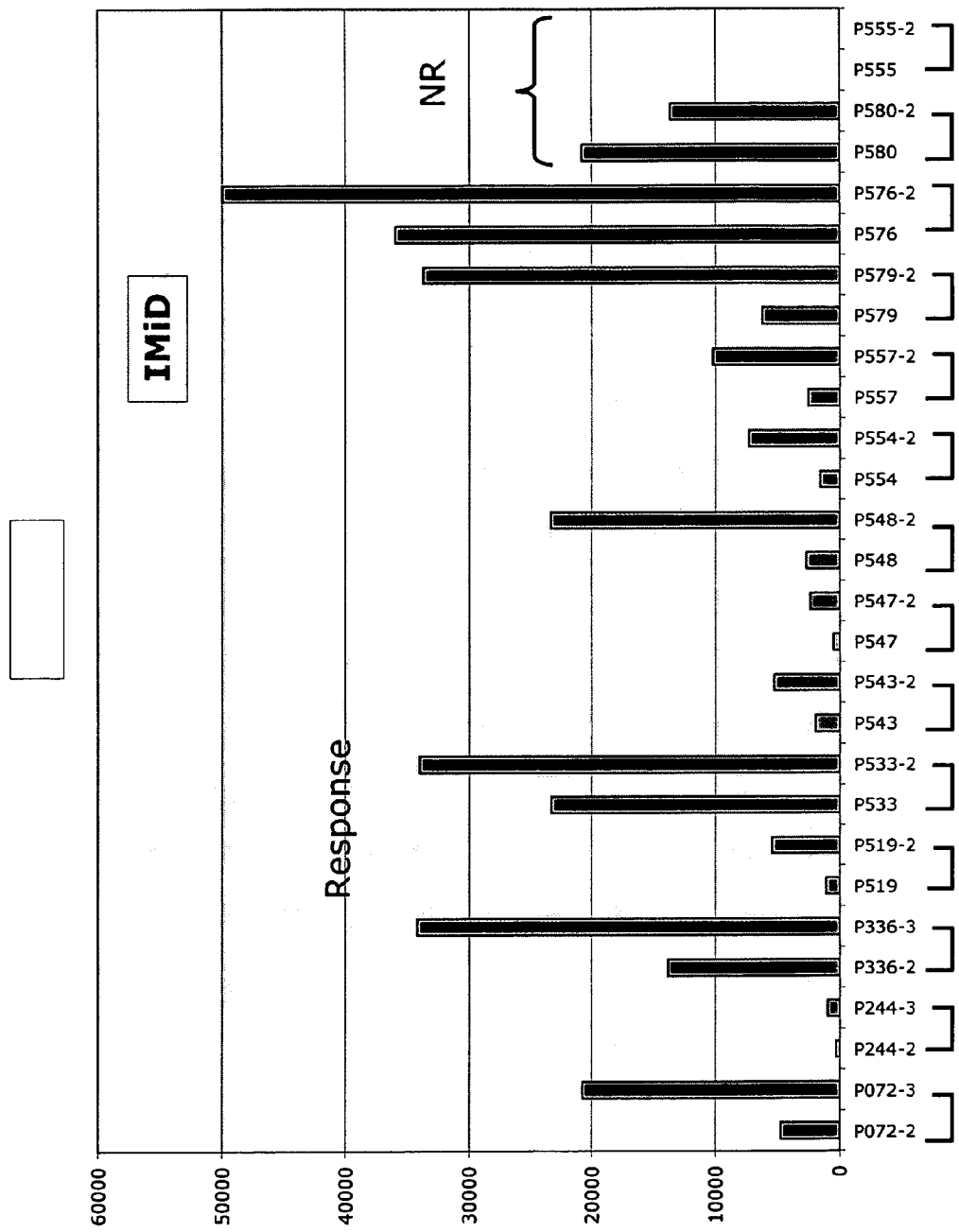
FIG. 34 shows DKK-1 expression after treatment with IMiD.
Figure 35:
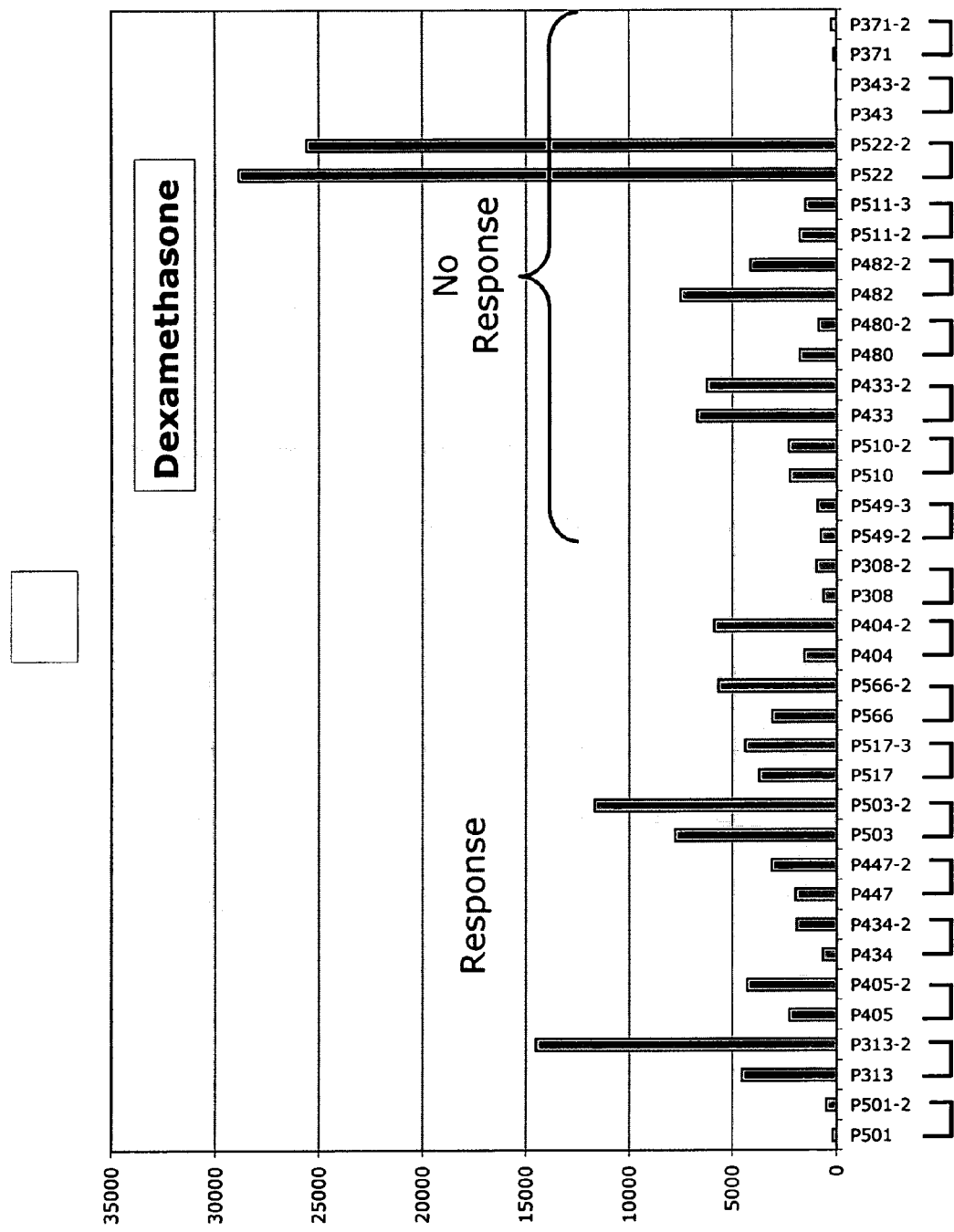
FIG. 35 shows DKK-1 expression after treatment with dexamethsone in newly diagnosed multiple myeloma.
Figure 36:
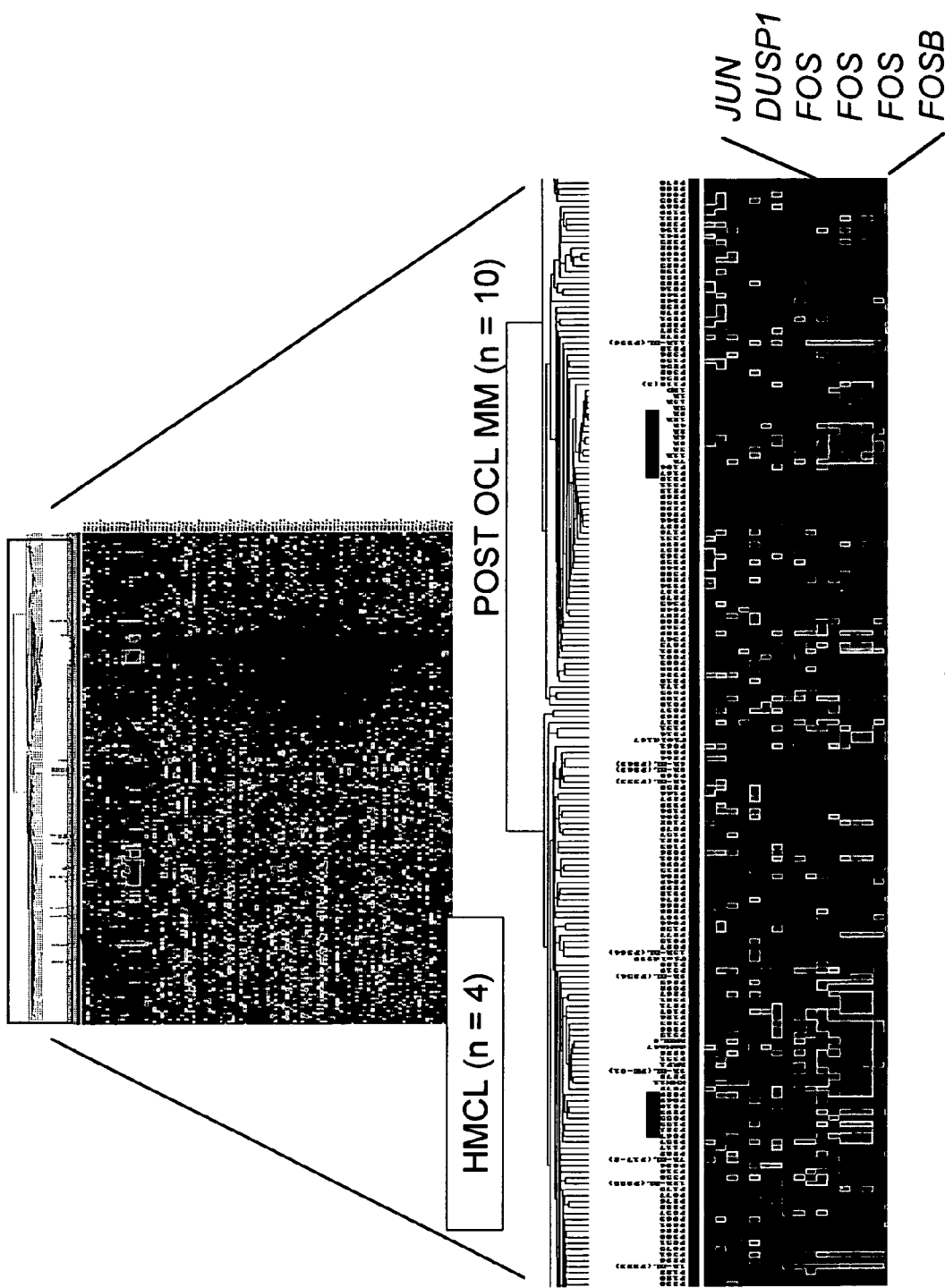
FIG. 36 shows downregulation of JUN and FOS in multiple myeloma cells after co-culture with osteoclasts.
Figure 37:
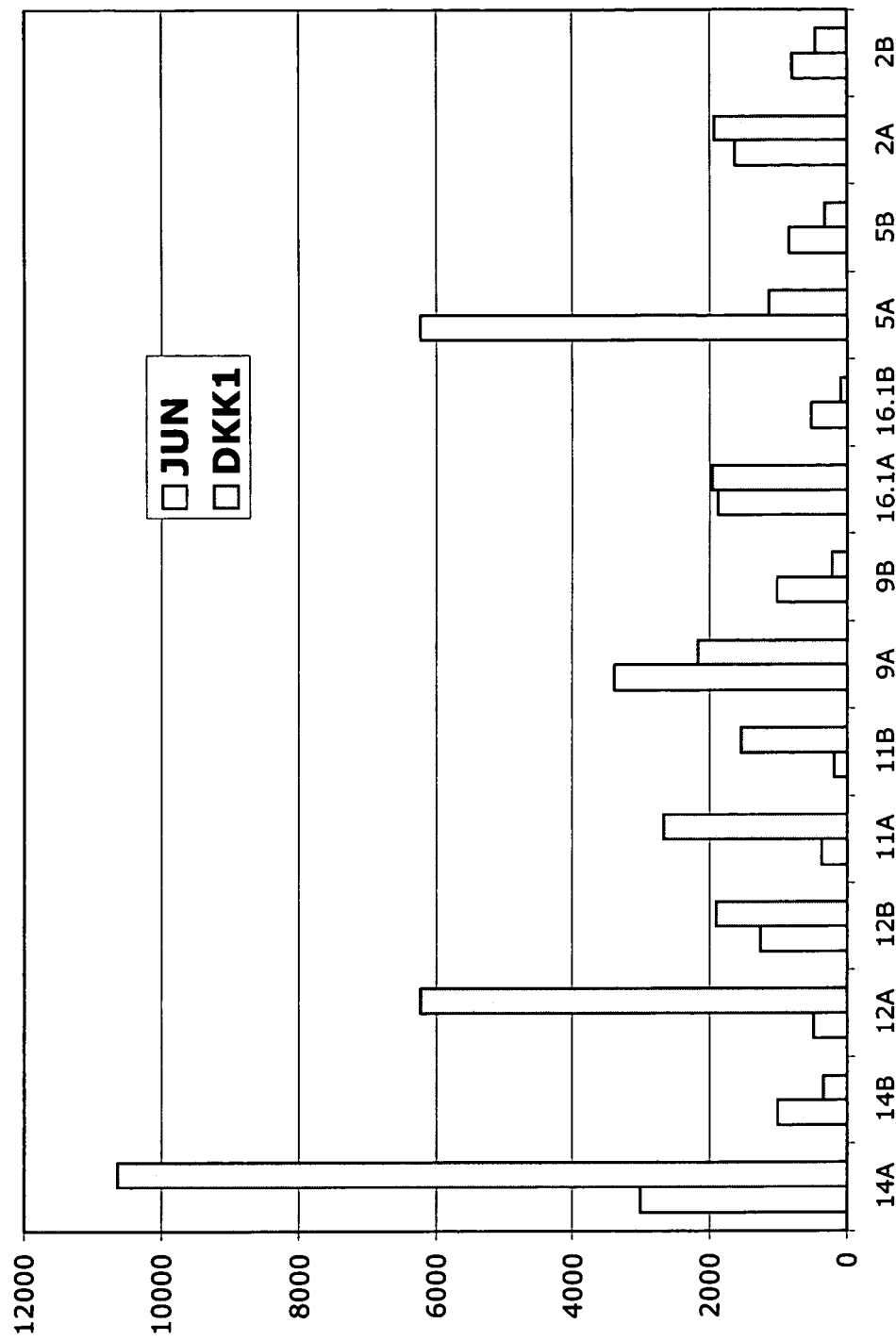
FIG. 37 shows JUN & DKK-1 downregulation in osteoclast co-culture.
Figure 38:
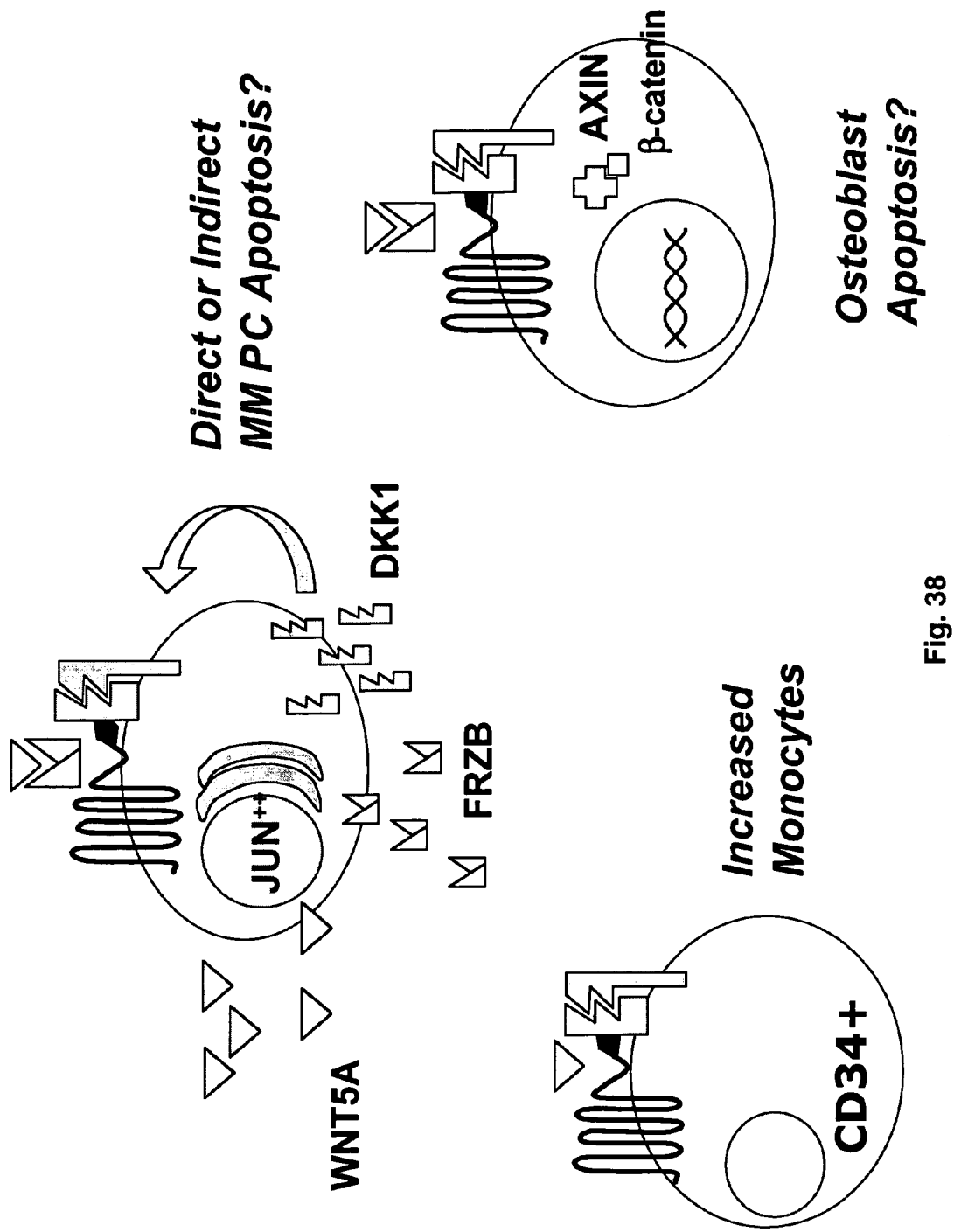
FIG. 38 shows WNT signaling in multiple myeloma bone disease.

It has been shown that DKK-1 expression is massively upregulated by UV irradiation and several other gentoxic stimuli. To see if multiple myeloma plasma cells also upregulate the genes in response to drugs used to treat this disease, gene expression profiling of multiple myeloma plasma cells was performed before and after 48 hour in vivo treatment with thalidomide (FIG. 33), ImiD (FIG. 34), PS-341 (FIG. 32), or dexamethasone (FIG. 35). These data showed that DKK-1 and FRZB expression could be massively upregulated in many cases and thus supporting a direct role of DKK-1 in triggering apoptosis of multiple myeloma plasma cells. It is interesting to note that a newly diagnosed patient who was primary refractory to all agents tested showed low levels of DKK-1 in initial prestudy tests and never showed increased expression of DKK-1 or FRZB after drug treatment, supporting a role for DKK-1 expression in promoting apoptosis of multiple myeloma plasma cells. In support of this notion, DKK-1 and FRZB were expressed at low to undetectable levels in 30 HMCL and several cases of extramedullary disease (FIG. 15).

EXAMPLE 14

Co-Culture of Multiple Myeloma with Osteoclasts Results in Massive Downregulation of JUN, FOS, and DKK-1

The close relationship between myeloma cells and osteoclasts is expressed clinically by the association of debilitating lytic bone destruction with multiple myeloma. The development of lytic bone lesions is caused by the activation of osteoclasts through direct and indirect interactions with myeloma plasma cells. The critical role of osteoclasts in the survival and growth of myeloma cells and in sustaining the disease process has been gleaned clinically and demonstrated in vivo in experimental models such as the SCID-hu model for primary human myeloma.

In order to investigate the molecular consequences of multiple myeloma plasma cell/osteoclast interactions, an ex vivo system was developed in which CD138-enriched multiple myeloma plasma cells were co-cultured with osteoclasts derived from multiple myeloma peripheral blood stem cells or PBSCs and MNC from healthy donors. CD138-enriched multiple myeloma plasma cells co-cultured with human osteoclasts derived from peripheral blood stem cells from normal donors or multiple myeloma patients maintained their viability and proliferative activity as indicated by annexin V flow cytometry, BrdU labeling index and [$^3$H]TdR incorporation for as long as 50 days. Purity level of plasma cells before and after co-cultures was greater than 95% as determined by CD38/CD45 flow cytometry.

Microarray analyses of the expression of ~12,000 genes in 12 multiple myeloma plasma cells were performed before and after 4 day co-culture. Heirarchical cluster analysis of the 12 multiple myeloma plasma cells pairs and 150 newly diagnosed multiple myeloma plasma cells using 7,913 probes sets (genes) revealed that whereas the pre-co-culture samples were distributed amongst 3 major cluster groups, the post-co-culture samples clustered tightly together in 2 of the major branches. An analysis of the significant gene expression changes after co-culture showed that 95 probe sets (genes) changed 2- to 50-fold (77 up- and 18 down-regulated) in at least 8 of the 12 multiple myeloma plasma cells after co-culture. CD138-enriched plasma cells from 5 healthy donors showed identical shifts in many of the same genes, suggesting that multiple myeloma plasma cells do not exhibit altered responses to osteoclasts. However, normal plasma cells as opposed to their malignant counterparts did not survive in long term co-cultures with osteoclasts.

The most striking changes were in the up-regulation of the chemokines GRO1, GRO2, GRO3, SCYA2, SCYA8, SCYA18, and IL8. Other notable genes included the chemokine receptor CCR1, osteopontin (SPP1), the integrins ITGB2 and ITGB5, matrix metalloproteinase 9 (MMP9), cathepsin K (CTSK) and cathepsin L (CTSL). Surprisingly, a large number of osteoclast-related genes were among the 77 up-regulated genes. The down-regulated genes included cyclin B (CCNB1), the cyclin B specific ubiquitin ligase UBE2C, the TSC-22 homologue DSIPI, and JUN, JUND, FOS, and FOSB.

Gene expression changes were also tested in 10 osteoclast cultured alone and after co-culture with multiple myeloma plasma cells. Twenty-four genes (14 up- and 10 down-regulated) changed 2- to 10-fold in at least 7 of 10 osteoclasts after co-culture. There were no significant differences in gene expression between multiple myeloma plasma cells cultured with osteoclasts derived from multiple myeloma patients or from healthy donors, suggesting that multiple myeloma osteoclasts are not qualitatively different than those derived from normal donors.

No significant changes in gene expression were observed when multiple myeloma plasma cells were cultured in media derived from a co-culture experiment, suggesting that contact is important. Given the low ratio of multiple myeloma plasma cells to osteoclasts in the co-culture experiments (1000:1), it is unlikely that all plasma cells can be in contact with the osteoclasts simultaneously. Thus, it is likely that some intercellular communication between multiple myeloma plasma cells in contact with osteoclasts and those other multiple myeloma plasma cells occurs.

It is known that osteoclasts play a major role in multiple myeloma bone disease as well as providing multiple myeloma with anti-apoptotic signals. Recent studies have shown that JUN directly regulates DKK-1 expression and that JUN and DKK-1 control apoptosis.

To determine if osteoclasts may prevent apoptosis of multiple myeloma plasma cells by modulating JUN and DKK-1, gene expression profiling was performed on purified plasma cells from 12 primary multiple myeloma cases before and after 48 hours of co-culture with in vitro derived osteoclasts. Multiple myeloma plasma cells in the co-culture had significantly higher long-term viability than cells cultured alone. Gene expression profiling of multiple myeloma plasma cells before and after osteoclast co-culture revealed that JUN, FOS, and FOSB were 3 of 40 genes down-regulated more than 2-fold in all cases (n=12/12). Hierarchical cluster analysis of HMCL and primary multiple myeloma cells with 95 genes significantly modulated in multiple myeloma plasma cells after co-culture revealed a striking similarity between HMCL, primary multiple myeloma co-cultured with osteoclasts and a subset of newly diagnosed multiple myeloma in that these cell types had relatively low levels of c-JUN and c-FOS.

Importantly, whereas primary multiple myeloma cells show a high degree of spontaneous apoptosis when cultured alone, multiple myeloma plasma cells cultured in the presence of osteoclasts can survive indefinitely. These data support a link between JUN and DKK-1 and also suggest that loss of JUN and DKK expression in multiple myeloma may be associated with disease progression as extramedulalary diseasse and HMCL, which are invariably derived from extramedullary disease, lack both JUN and DKK. It is interesting to speculate that one of the major influences of osteoclasts on multiple myeloma growth and behavior is to downregulate JUN and DKK-1, which directly affects plasma cells apoptosis. Treatment of HMCL and primary multiple myeloma/osteoclasts co-cultures with DKK-1 is expected to result in apoptosis of multiple myeloma plasma cells. DKK-1 will likely have no effect on the osteoclasts, as these cells do not express the Wnt co-receptor LRP-5. Normal bone marrow derived plasma cells also do not express DKK-1 and may help explain their long-lived nature.

EXAMPLE 15

Synthesis of DKK1 Protein by Plasma Cells

Figure 39:
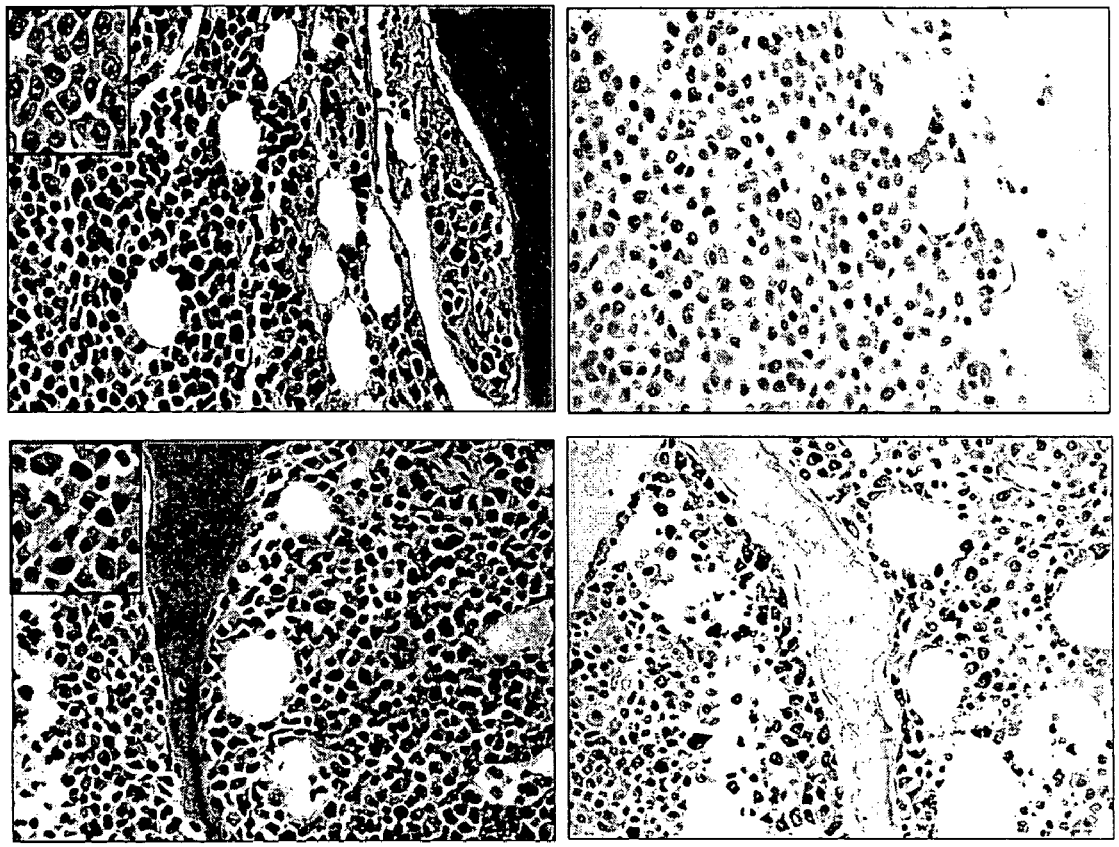
FIG. 39 shows overexpression of DKK1 in low grade myeloma with the loss of expression with disease progression. Expression of DKK1 was examined by immunohistochemistry of myeloma bone marrow biopsies. Serial sections (550× magnification) of bone marrow biopsies from myeloma patients with high (a-b) and low (c-d) DKK1 gene expression are presented. Slides are stained with H&E (a and c) or anti-DKK1 and secondary antibody (b and d). Use of secondary alone failed to stained cells (data not shown). Magnified images (1,200× magnification) are located in the upper left corner of each H&E image. Image a shows a myeloma with an interstitial pattern of involvement with plasma cells exhibiting low grade morphology with abundant cytoplasm and no apparent nucleoli. Image b reveals positive staining of plasma cells in a interstitial pattern with anti-DKK1 antibody that was greatest adjacent to bone. Image c shows a myeloma with nodular or alliterative pattern with plasma cells exhibiting high grade morphology with enlarged nuclei and prominent nucleoli. Image d reveals no positive staining of plasma with anti-DKK1 antibody.

Serial sections from bone marrow biopsies of 65 cases of multiple myeloma were stained for the presence of DKK1. The plasma cells in these cases contained DKK1 in a manner consistent with the gene expression data (FIG. 39). Similar experiments with biopsies from 5 normal donors failed to identify DKK1 in any cell. There was a strong tendency for DKK1 positive myelomas to have low-grade morphology (abundant cytoplasm without apparent nucleoli) with an interstitial growth pattern. This staining was found to be greatest in plasma cells adjacent to bone. DKK1 negative myelomas tend to bear high-grade morphology (enlarged nuclei and prominent nucleoli) with a nodular or obliterative growth pattern. In biospies with an interstitial growth pattern, DKK1 was either present (in varying percentages of cells) or absent. In contrast, myelomas with the more aggressive nodular growth patterns DKK1 was uniformly absent. Importantly, in cases with both interstitial and nodular growth, the interstitial cells were positive and the nodular cells negative.

EXAMPLE 16

DKK1 Protein in Bone Marrow Plasma

Figure 40A:
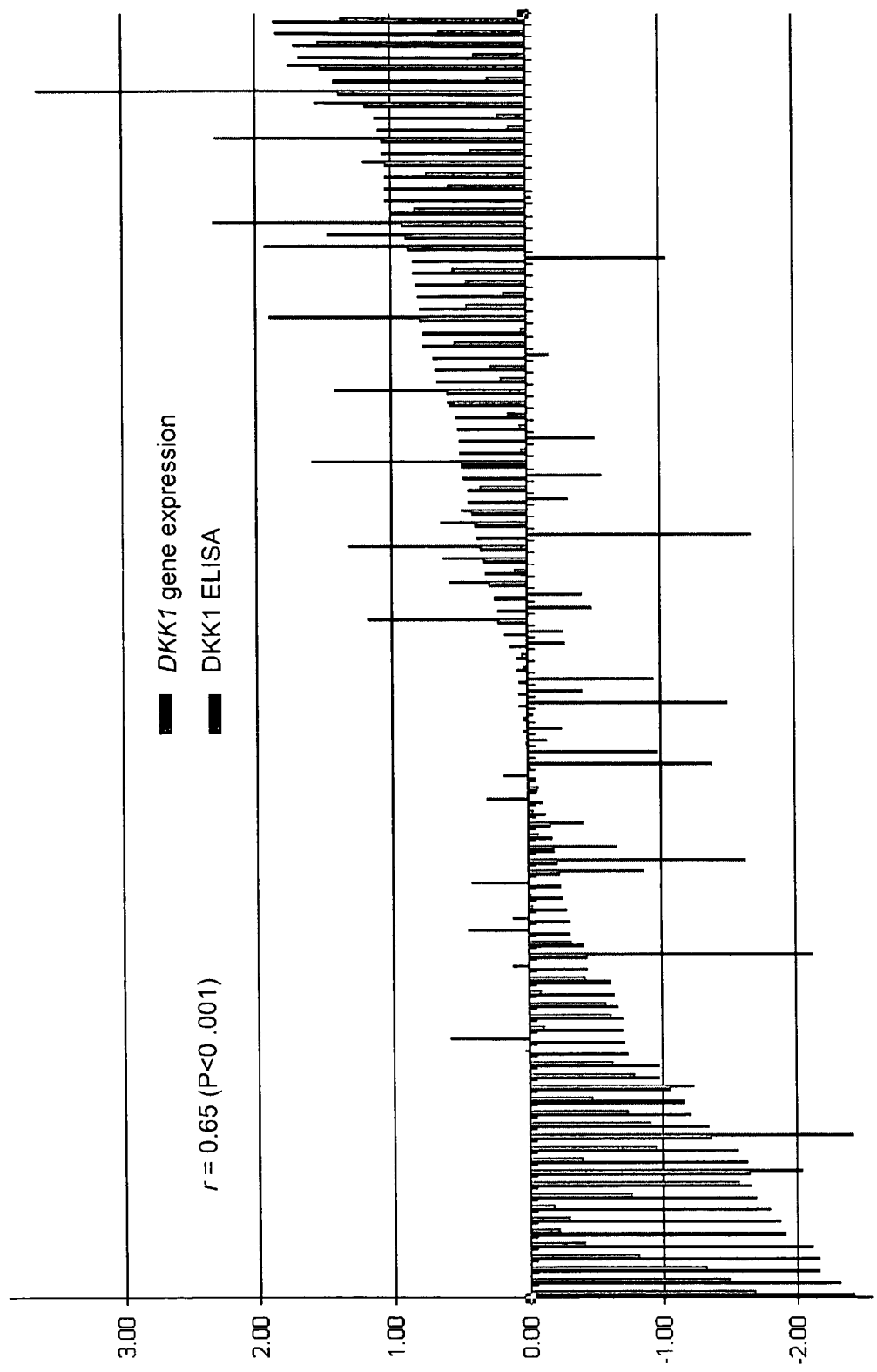
FIGS. 40A and 40B show DKK1 protein in the bone marrow plasma is highly correlated with DKK1 gene expression and the presence of bone lesions.

An enzyme-linked immunosorbent assay (ELISA) showed that the concentration of DKK1 protein in the bone marrow plasma from 107 of the 173 newly diagnosed multiple myeloma patients for which gene expression data was also available, was 24.02 ng/ml (S.D. 49.58). In contrast, DKK1 was 8.9 ng/ml (S.D. 4.2) in 14 normal healthy donors, 7.5 ng/ml (S.D. 4.5) in 14 cases of MGUS, and 5.5 ng/ml (S.D. 2.4) in 9 cases of Waldenström's macroglobulinemia. DKK1 gene expression and the level of DKK1 in the bone marrow plasma were positively correlated (r=0.65, P<0.001) in the 107 cases of myeloma (FIG. 40A). There was also a strong correlation between DKK1 protein levels in bone marrow plasma and peripheral blood plasma in 41 cases of myeloma in which both samples were taken simultaneously (r=0.57, P<0.001).

Figure 40B:
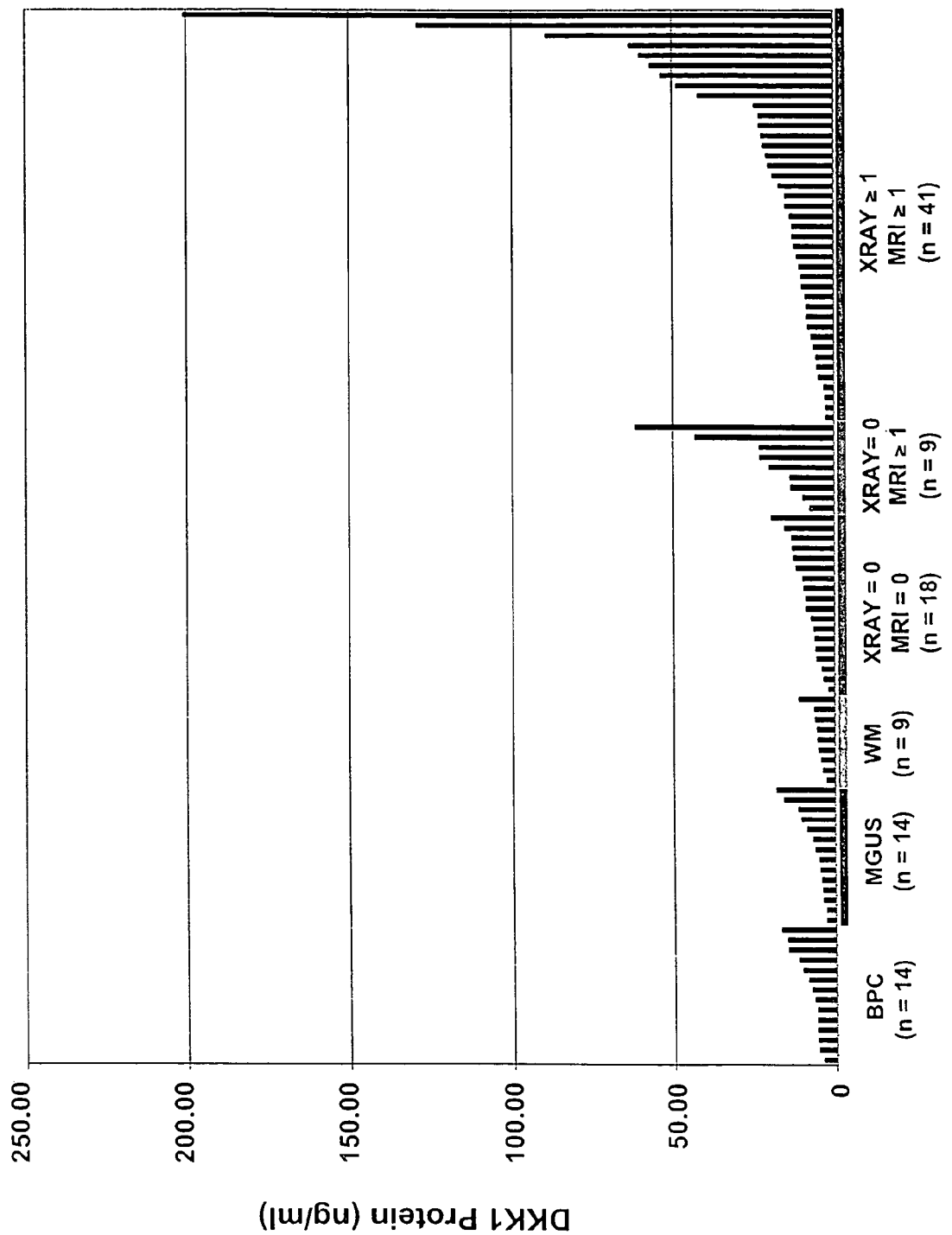

In 68 patients in whom both DKK1 protein levels in the bone marrow plasma and the presence of bone lesions were determined, DKK1 protein in patients with 1+MRI and no x-ray lesions differ significantly compared to patients with no MRI and no x-ray lesions (median level: 20 ng/ml vs. 9 ng/ml; p=0.002), but does not differ significantly compared to patients with 1+MRI and 1+x-ray lesions (median level: 20 ng/ml vs. 14 ng/ml; p=0.36) (FIG. 40B, Table 2).

EXAMPLE 17

Effect of Bone Marrow Serum on Osteoblast Differentiation In Vitro

Figure 41A:
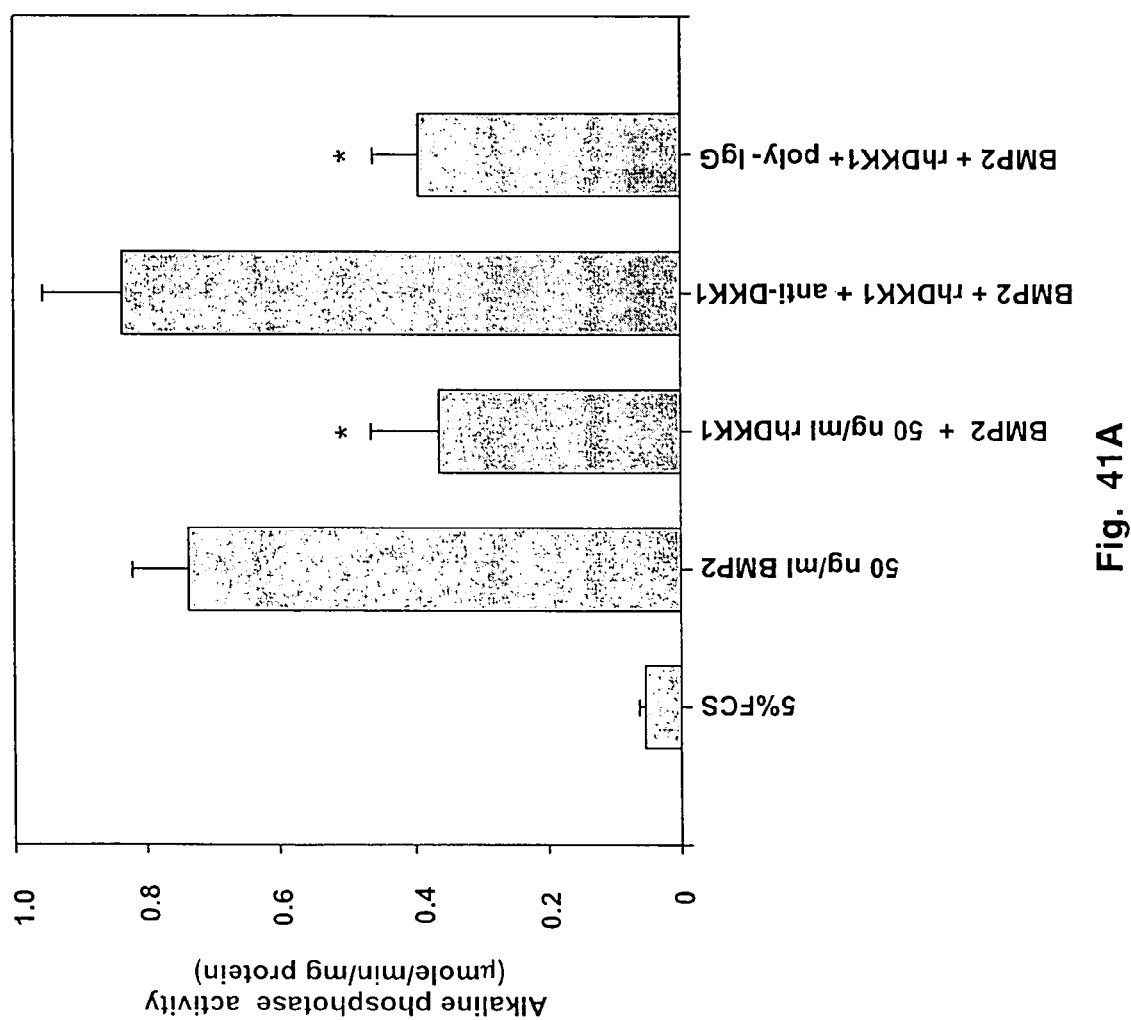
FIGS. 41A and 41B show recombinant DKK1 and MM plasma can block alkaline phosphatase production in BMP-2 treated C2C12 cells in a DKK1-dependent manner.
Figure 41B:
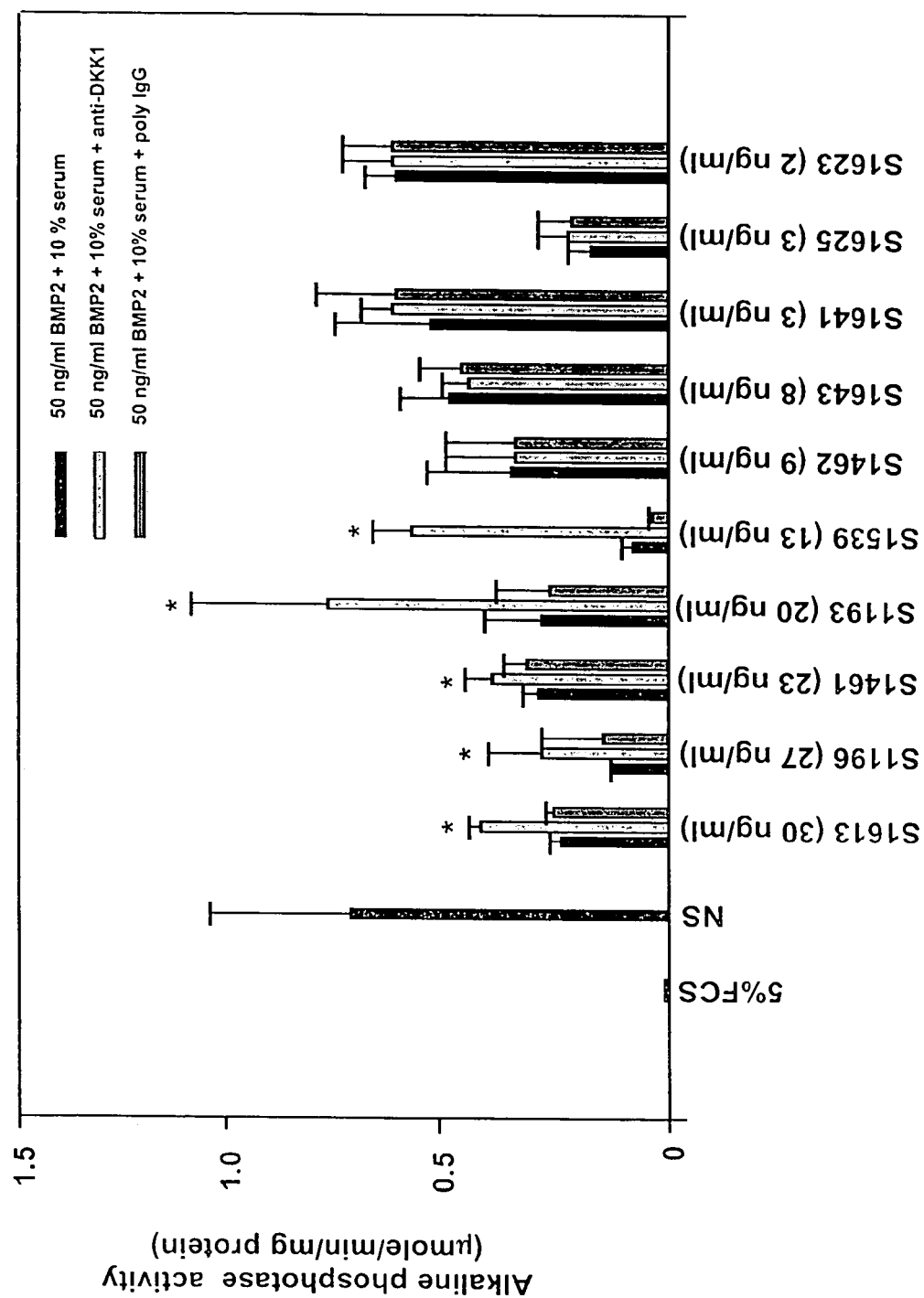

Bone morphogenic protein-2 can induce differentiation of the uncommitted mesenchymal progenitor cell line C2C12 (Katagiri, et al., 1994) into osteoblasts through a mechanism that involves Wnt/b-catenin signaling (Bain, et al., 2003; Roman-Roman, et al., 2002). Alkaline phosphatase, a specific marker of osteoblast differentiation, was undetectable in C2C12 cells grown in 5 percent fetal calf serum for 5 days (FIG. 41A). Treatment of C2C12 cells with 50 ng/ml of BMP-2 for 5 days induced them to produce alkaline phosphatase, whereas alkaline phosphatase was not produced by C2C12 cells that were concomitantly cultured with BMP-2 and 50 ng/ml recombinant human DKK1. This in vitro effect on alkaline phosphatase production was neutralized by a polyclonal anti-DKK1 antibody, but not by a non-specific polyclonal goat IgG. Bone marrow serum with a DKK1 concentration >12 ng/ml from five patients with myeloma inhibited the production of alkaline phosphatase by C2C12 cells treated with BMP-2, and this effect was reversed by the anti-DKK1 antibody, but not by non-specific IgG (FIG. 41B). By contrast, C2C12 cells treated with 50 ng/ml BMP-2 and 10 percent serum from the bone marrow of a normal donor induced the production of alkaline phosphatase by the cells (FIG. 41B).

The following references were cited herein:

Zhan et al., Global gene expression profiling of multiple myeloma, monoclonal gammopathy of undetermined significance, and normal bone marrow plasma cells. Blood 99:1745-1757 (2002).

Zhan et al., Gene expression profiling of human plasma cell differentiation and classification of multiple myeloma based on similarities to distinct stages of late-stage B-cell development. Blood 101:1128-1140 (2003).

Fedi et al. Isolation and biochemical characterization of the human Dkk-1 homologue, a novel inhibitor of mammalian Wnt signaling. J Biol Chem 274:19465-72 (1999).

Gallea et al. Activation of mitogen-activated protein kinase cascades is involved in regulation of bone morphogenetic protein-2-induced osteoblast differentiation in pluripotent C2C12 cells. Bone 28:491-8 (2001).

Spinella-Jaegle et al. Opposite effects of bone morphogenetic protein-2 and transforming growth factor-beta1 on osteoblast differentiation. Bone 29:323-30 (2001).

Westfall and Young. Resampling-based multiple testing: Examples and methods for p-value adjustment. Hoboken, N.J.: Wiley-Interscience, 360 (1993).

Golub et al. Molecular classification of cancer: class discovery and class prediction by gene expression monitoring. Science 286:531-7 (1999).

Katagiri et al. Bone morphogenetic protein-2 converts the differentiation pathway of C2C12 myoblasts into the osteoblast lineage. J Cell Biol 127:1755-66 (1994).

Bain et al. Activated beta-catenin induces osteoblast differentiation of C3H10T1/2 cells and participates in BMP2 mediated signal transduction. Biochem Biophys Res Commun 301:84-91 (2003).

Roman-Roman et al. Wnt-mediated signalling via LRP5 and beta-catenin induce osteoblast differentiation and mediates the effects of BMP2, American Society of Bone Mineral Research, 2002.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of diagnosing lytic bone disease treatable by decreasing DKK-1 expression at the protein level in an individual with multiple myeloma, comprising:
   measuring the expression level of the human homologue of Dickkopf-1 (DKK-1) protein in said individual, wherein an increased expression of said protein compared to that in a healthy individual indicates that said individual has a lytic bone disease treatable by decreasing DKK-1 expression at the protein level.

2. The method of claim 1, wherein said expression level is measured by enzyme-linked immunosorbent assay, immunohistochemistry or flow cytometry.

3. A method of diagnosing DKK1-associated lytic bone disease in an individual having multiple myeloma, comprising:
   measuring the expression level of the human homologue of Dickkopf-1 (DKK-1) protein in said individual, wherein an increased expression of said protein compared to that in a healthy individual indicates that said individual has DKK1-associated lytic bone disease.

4. The method of claim 3, wherein said expression level is measured by enzyme-linked immunosorbent assay, immunohistochemistry or flow cytometry.

* * * * *